(12) United States Patent
Schlom et al.

(10) Patent No.: US 7,247,615 B2
(45) Date of Patent: Jul. 24, 2007

(54) PEPTIDE AGONISTS OF PROSTATE-SPECIFIC ANTIGEN AND USES THEREFOR

(75) Inventors: Jeffrey Schlom, Potomac, MD (US); Kwong-yok Tsang, Bethesda, MD (US)

(73) Assignee: United States of America, represented by the Secretary, Department of Health and Human Services, Washington, DC (US)

( * ) Notice: Subject to any disclaimer, the term of this patent is extended or adjusted under 35 U.S.C. 154(b) by 319 days.

(21) Appl. No.: 10/497,003

(22) PCT Filed: Nov. 26, 2002

(86) PCT No.: PCT/US02/37805
§ 371 (c)(1), (2), (4) Date: Aug. 24, 2004

(87) PCT Pub. No.: WO03/047506
PCT Pub. Date: Jun. 12, 2003

(65) Prior Publication Data
US 2005/0054575 A1 Mar. 10, 2005

Related U.S. Application Data

(60) Provisional application No. 60/334,669, filed on Nov. 30, 2001, provisional application No. 60/334,575, filed on Nov. 30, 2001.

(51) Int. Cl.
| | |
|---|---|
| *A61K 38/08* | (2006.01) |
| *C12P 21/02* | (2006.01) |
| *C12N 1/21* | (2006.01) |
| *C12N 1/19* | (2006.01) |
| *C12N 15/63* | (2006.01) |
| *C12N 5/10* | (2006.01) |
| *C07K 7/06* | (2006.01) |
| *C07H 21/04* | (2006.01) |

(52) U.S. Cl. .................. 514/15; 435/69.1; 435/235.3; 435/254.11; 435/320.1; 435/325; 530/328; 536/23.5

(58) Field of Classification Search .............. None
See application file for complete search history.

(56) References Cited

U.S. PATENT DOCUMENTS 6,235,486 B1 * 5/2001 Young et al. ............... 435/7.1

FOREIGN PATENT DOCUMENTS

| WO | 97/35021 A2 | 9/1997 |
|---|---|---|
| WO | WO 01/87325 A1 | 11/2001 |

OTHER PUBLICATIONS

Digby et al., "Human prostate specific antigen (PSA) gene: structure and linkage to the kallikrein-like gene, hGK-1," Nucleic Acids Research, 17 (5), 2137, 1989—cited as GenBank locus HAPA4.*
Dias et al., "Shotgun sequencing of the human transcriptome with ORF expressed sequence tags," PNAS 97 (7) 3491-3496, Mar. 2000.*
Digbyet al., "Human prostate specific antigen (PSA) gene: structure and linkage to the kallikrein-like gene, hGK-1," Nucleic Acids Res. 17 (5), 2137 (1989).*
Pierpaolo Correale et al., "Generation of Human Cytolytic T Lymphocyte Lines Directed Against Prostate-Specific Antigen (PSA) Employing a PSA Oligoepitope Peptide", J. Immunol., 1998, pp. 3186-3194, vol. 161.
Pierpaolo Correale et al., "In Vitro Generation of Human Cytotoxic T Lymphocytes Specific for Peptides Derived From Prostate-Specific Antigen", J. Nat Cancer Inst., 1997, pp. 293-300, vol. 19.
Pamela M.J. McLaughlin et al., "Cancer immunotheraphy: insights from transgenic animal models", Critical Reviews in Oncology/Hermatology, 2001, pp. 53-76, vol. 40.
Hiroshi Terasawa et al., "Identification and Characterization of a Human Agonist Cyctotoxic T-Lymphocyte Epitope of Human Prostate-specific Antigen", Clinical Cancer Research, Jan. 2002, pp. 41-53, vol. 8.
Slawin et al., Oct. 22, 1998, Database EMBL [Online] Prostate-specific antigen protein hK3, reprived from EMBL accession No. AAW83213, XP002409862.

* cited by examiner

*Primary Examiner*—Robert A. Wax

(57) ABSTRACT

This invention relates to isolated peptides comprising agonist epitopes of prostate-specific antigen (PSA). In various aspects, the invention relates to peptides comprising agonist epitopes of the PSA-3 cytotoxic T lymphocyte epitope, and nucleic acids encoding peptides that comprise PSA-3 agonist epitopes. Also related are probes, primers, and vectors comprising these nucleic acids, as well as host cells comprising these vectors, and antibodies that bind to the PSA-3 agonist peptides. This invention further relates to diagnostic reagents and methods utilizing the disclosed nucleic acids or antibodies. The invention also relates to pharmaceutical compositions comprising the nucleic acids, host cells, and peptides of the invention, as well as methods of treatment or prevention of prostate cancer employing such compositions, for example, for peptide-mediated, cell-mediated, and vector-mediated immunotherapies.

23 Claims, 9 Drawing Sheets

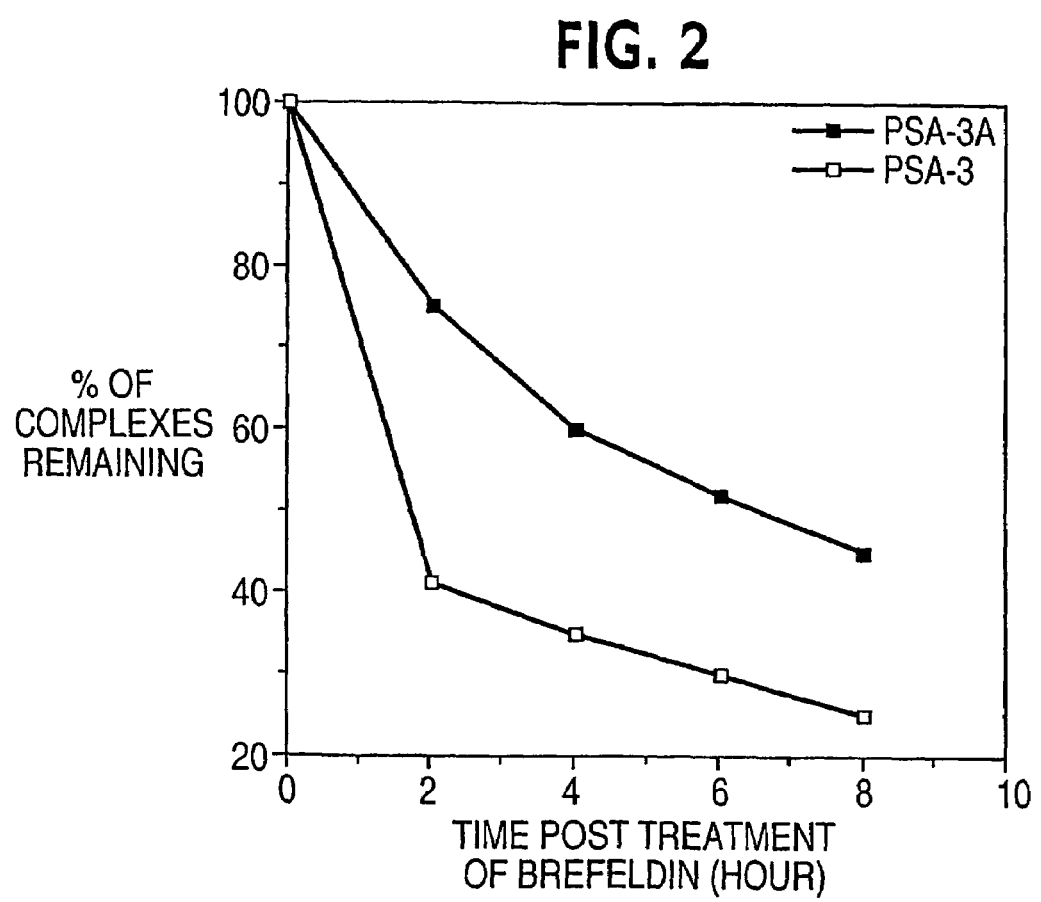

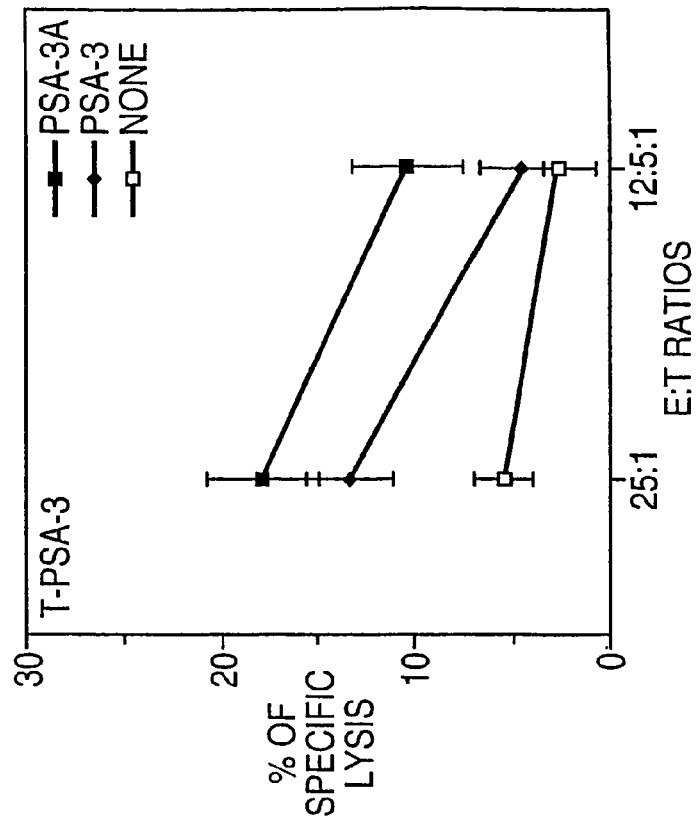
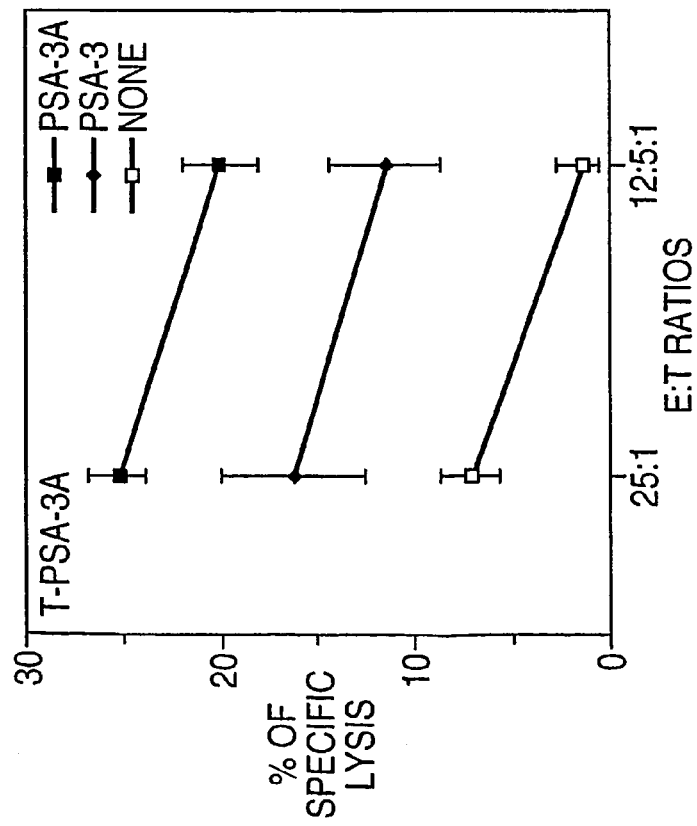

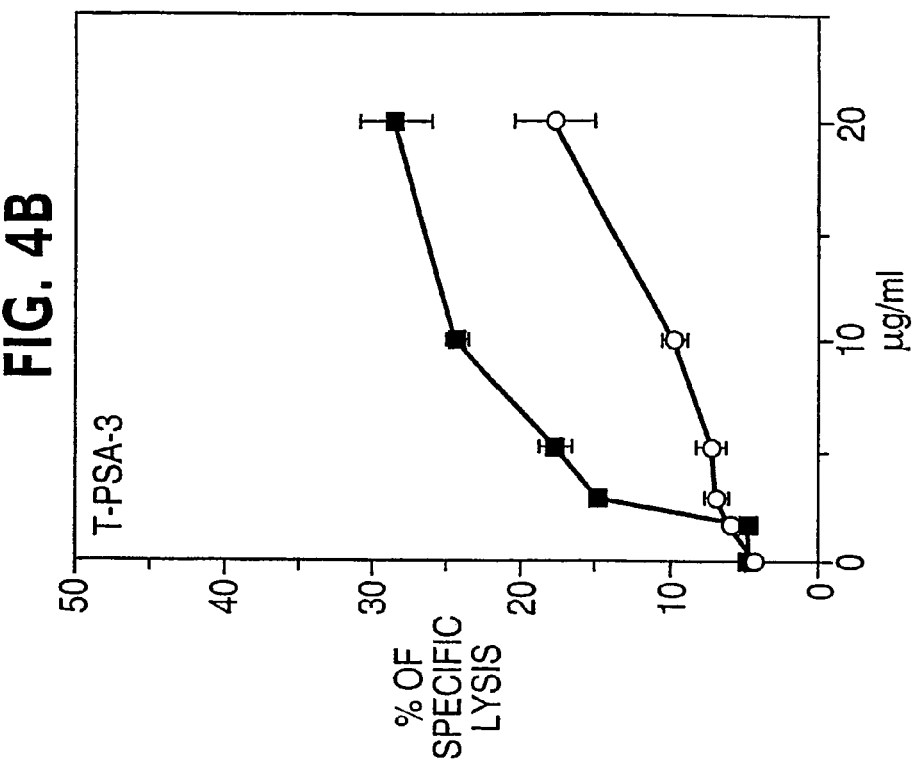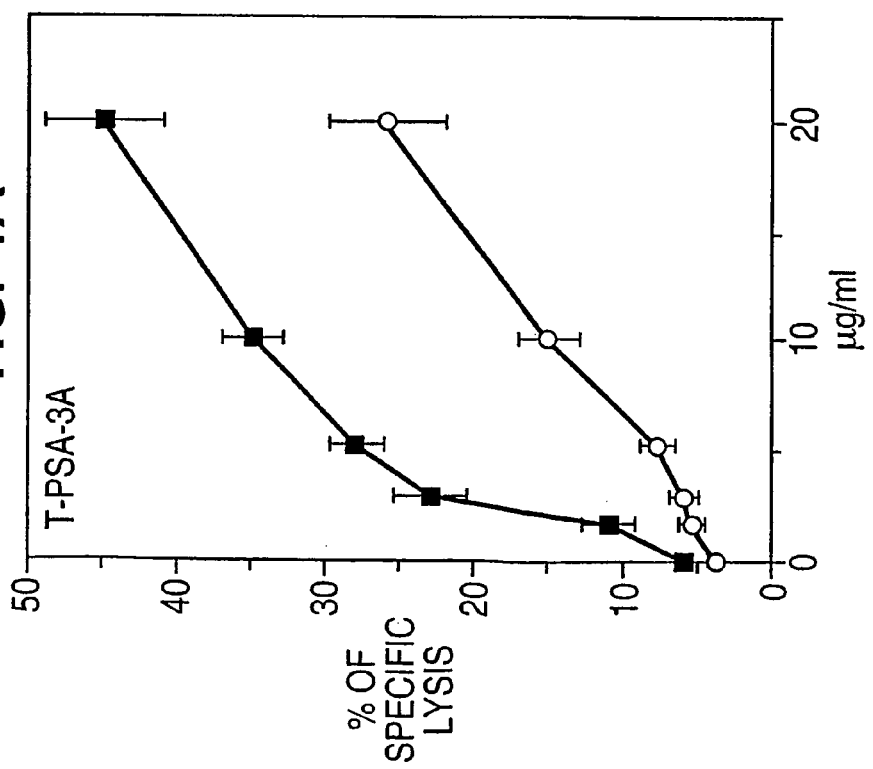

FIG. 7A

```
  1 mwvpvvfltl svtwigaapl ilsrivggwe cekhsqpwqv lvasrgravc ggvlvhpqwv
 61 ltaahcirnk svillgrhsl fhpedtgqvf qvshsfphpl ydmsllknrf lrpgddsshd
121 lmllrlsepa eltdavkvmd lptqepalgt tcyasgwgsi epeefltpkk lqcvdlhvis
181 ndvcagvhpq kvtkfmlcag rwtggkstcs gdsggplvcn gvlggitswg sepcalperp
241 slytkvvhyr kwikdtivan p
```

FIG. 7B

```
  1 ivggwecekh sqpwqvlvas rgravcggvl vhpqwvltaa hcirnksvil lgrhslfhpe
 61 dtgqvfqvsh sfphplydms llknrflrpg ddsshdlmll rlsepaeltd avkvmdlptq
121 epalgttcya sgwgsiepee fltpkklqcv dlhvisndvc agvhpqkvtk fmlcagrwtg
181 gkstcsgdsg gplvcngvlq gitswgsepc alperpslyt kvvhyrkwik dtivanp
```

FIG. 7C

```
  1 mwvpvvfltl svtwigaapl ilsrivggwe cekhsqpwqv lvasrgravc ggvlvhpqwv
 61 ltaahcirnk svillgrhsl fhpedtgqvf qvshsfphpl ydmsllknrf lrpgddsshd
121 lmllrlsepa eltdavkvmd lptqepalgt tcyasgwgsi epeefltpkk lqcvdlhvls
181 ndvcagvhpq kvtkfmlcag rwtggkstcs gdsggplvcn gvlggitswg sepcalperp
241 slytkvvhyr kwikdtivan p
```

FIG. 7D

```
  1 ivggwecekh sqpwqvlvas rgravcggvl vhpqwvltaa hcirnksvil lgrhslfhpe
 61 dtgqvfqvsh sfphplydms llknrflrpg ddsshdlmll rlsepaeltd avkvmdlptq
121 epalgttcya sgwgsiepee fltpkklqcv dlhvlsndvc agvhpqkvtk fmlcagrwtg
181 gkstcsgdsg gplvcngvlq gitswgsepc alperpslyt kvvhyrkwik d

FIG. 7G

```
  1  mwvpvvfltl svtwigaapl ilsrivggwe cekhsqpwqv lvasrgravc ggvlvhpqwv
 61  ltaahcirnk svillgrhsl fhpedtgqvf qvshsfphpl ydmsllknrf lrpgddsshd
121  lmllrlsepa eltdavkvmd lptqepalgt tcyasgwgsi epeefltpkk lqcvdlhyls
181  ndvcagvhpq kvtkfmlcag rwtggkstcs gdsggplvcn gvlqgitswg sepcalperp
241  slytkvvhyr kwikdtivan p
```

FIG. 7H

```
  1  ivggwecekh sqpwqvlvas rgravcggvl vhpqwvltaa hcirnksvil lgrhslfhpe
 61  dtggvfqvsh sfphplydms llknrflrpg ddsshdlmll rlsepaeltd avkvmdlptq
121  epalgttcya sgwgsiepee fltpkklqcv dlhylsndvc agvhpqkvtk fmlcagrwtg
181  gkstcsgdsg gplvcngvlq gitswgsepc alperpslyt kvvhyrkwik dtivanp
```

PEPTIDE AGONISTS OF PROSTATE-SPECIFIC ANTIGEN AND USES THEREFOR

This application claims priority to U.S. provisional application Ser. No. 60/334,669 filed Nov. 30, 2001, and to U.S. provisional application Ser. No. 60/334,575, filed Nov. 30, 2001, the entirety of both of which is hereby incorporated by reference.

This application is a 371 of PCT/US02/37805, filed Nov. 26, 2002, the entirety of which is hereby incorporated by reference.

BACKGROUND OF THE INVENTION

1. Field of the Invention

The present invention relates to isolated peptides comprising agonist epitopes of prostate-specific antigen (PSA). In one aspect, this invention relates to peptides comprising agonist epitopes of the PSA-3 CTL (cytotoxic T lymphocyte) epitope. The invention also relates to nucleic acids (e.g., recombinant viral vectors) encoding peptides that comprise PSA-3 agonist epitopes, as well as host cells comprising these nucleic acids, and antibodies that bind to these peptides. Also related are pharmaceutical compositions comprising the nucleic acids and peptides of the invention, as well as methods of treatment of prostate cancer employing such compositions, e.g., peptide-mediated and vector-mediated immunotherapy.

2. Description of the Background

Current treatment for prostate cancer involves surgery, radiation, chemotherapy, and/or hormonal therapy. In spite of these treatments, over 40,000 men die of prostate cancer each year in the U.S. alone (C. C. Boring et al., 1994, CA Cancer J. Clin. 44:7–26). One promising modality for the treatment of prostate cancer involves vaccine therapy. Prostate-specific antigen (PSA), an antigen expressed on prostate carcinoma, is an important target for vaccine therapy (K. W. Watt et al., 1986, Proc. Natl. Acad. Sci. USA, 83:3166–3170). While PSA is expressed on normal prostatic epithelium, it is not expressed to any appreciable level on other normal adult tissues. However, PSA is a "self-antigen," giving rise to immunotolerance.

Two vaccine clinical trials have been conducted using a recombinant vaccinia virus expressing the PSA gene (rV-PSA) as an immunogen. These studies demonstrated that both anti-PSA antibody responses (M. G. Sanda et al., 1999, Urology 53:260–266) and PSA-specific T cell responses (J. P. Eder et al., 2000, Clin. Cancer Res. 6:1632–1638) could be induced in vaccinated patients. In one trial, T cell responses to a 10-mer PSA peptide was induced in five out of seven prostate cancer patients following vaccination with rV-PSA. These results were achieved using an ELISPOT assay in which PBMCs of patients were incubated overnight with peptidepulsed APCs (antigen presenting cells). The short incubation period was used to prevent artifacts due to prolonged cycles of in vitro peptide stimulation of T cells (J. P. Eder et al., 2000, Clin. Cancer Res. 6:1632–1638). Notably, no PSA-specific T cell responses were observed when PBMCs were used prior to vaccination with rV-PSA.

The peptide used to monitor immune responses in patients receiving rV-PSA was an HLA-A2 binding 10-mer peptide, designated PSA-3 (VISNDVCAQV; SEQ ID NO:1; P. Correale et al., 1997, J. Natl. Cancer Inst. 19:293–300; P. Correale et al., 1998, J. Immunol. 161:3186–3194). The HLA-A2 binding peptide was used to monitor patients who were positive for the HLA-A2 allele. Patients possessing the HLA-A2 allele were chosen for monitoring because it is the most common HLA allele in individuals in North America and is expressed by approximately 50% of the Caucasian population (J. Lee, 1990, "The HLA system: a new approach" Proceedings Of The First Red Cross International Histocompatibility Workshop Springer Verlag, New York, p. 154).

Previous studies also demonstrated that the PSA-3 epitope was naturally processed by tumor cells, and bound to MHC-class I A2 molecules on the surface of prostate cancer cells. This binding rendered prostate cells susceptible to lysis by specific T cells in an MHC-restricted manner (P. Correale et al., 1998, J. Immunol. 161:3186–3194). In addition, prior studies analyzed the amino acid sequence of the PSA molecule using both computer algorithms, and by peptide-binding studies to the HLA-A2 positive T2A2 cell line (K. S. Anderson et al., 1993, J. Immunol. 151:3407–3419). Studies also analyzed the ability of various PSA peptides to generate CTL lines in vitro. This analysis demonstrated that the PSA-3 peptide was optimal for these properties.

The PSA-3 peptide was subsequently used in the ELISPOT assay to monitor immune responses in vaccinated patients (J. P. Eder et al., 2000, Clin. Cancer Res. 6:1632-1638; P. Arlen et al., 2000, Cancer Immuno. Immunother. 49:517–529). The results of these studies indicated that increases in precursor frequencies observed in the ELISPOT assay as a result of vaccination with rV-PSA were relatively modest (i.e., 2- to 4-fold) (J. P. Eder et al., 2000, Clin. Cancer Res. 6:1632–1638). Thus, there is a need in the art for compositions and methods for enhancing the immunogenicity of PSA.

The present invention therefore describes compositions and methods for increasing PSA immunogenicity, as well as treatments employing these compositions and methods. In accordance with this invention, the immunogenicity of PSA peptides was increased by modifying the amino acid residues that interact with HLA molecules. Previous studies have shown that amino acid modification in the anchor residues of peptides may result in enhanced binding to MHC and enhanced T cell activation, while other amino acid modifications will have no effect or act to antagonize T cell activation (H. M. Grey et al., 1995, Cancer Surv. 22:37–49; M. T. De Magistris et al., 1992, Cell 68:625–632; S. C. Jameson et al., 1995, Immunity 2:1–11; S. Zaremba et al., 1997, Cancer Res. 57:4570-4577). Enhancement of T cell activation by modifying HLA-anchor residues has been demonstrated for some human melanoma-associated antigens (D. Valmori et al., 1998., J. Immunol. 160:1750–1758, 1998; Y. Kawakami, Y., Eliyahu et al., 1995, J. Immunol. 154:3961–3968), but has not been demonstrated for antigens associated with most solid tumors, leukemias, or lymphomas.

The experiments of this invention, shown herein below, describe the design and analysis of an agonist of the PSA-3 CTL epitope, designated PSA-3A. These experiments demonstrate that when compared with the native PSA-3 epitope, the PSA-3A epitope exhibited enhanced binding to the MHC-class I A2 allele and resulted in enhanced stability of the peptide MHC complex. As shown herein, T cell lines generated with either the PSA-3 or the PSA-3A peptide showed higher levels of lysis of targets pulsed with the PSA-3A peptide than those targets pulsed with the PSA-3 peptide. This was observed when both concentration of peptide and effector to target cells ratios were titrated.

The experiments of this invention further show that T cells stimulated with dendritic cells (DCs) pulsed with PSA-3A peptide produced higher levels of IFN-γ than DCs pulsed with PSA-3 peptide. However, no increase in apoptosis was observed in T cells stimulated with the PSA-3A agonist as 15 compared with those stimulated with PSA-3. Notably, human T cell lines generated with the PSA-3A agonist had the ability to lyse human prostate carcinoma cells expressing native PSA in an MHC-A2 restricted manner.

In accordance with the present invention, recombinant vaccinia viruses were constructed containing the entire PSA transgene with or without the single amino acid change that constitutes the PSA-3A epitope. DCs infected with the recombinant vector containing the agonist amino acid change within the entire PSA gene (designated rV-PSA-3A) were more effective than the rV-PSA vector in enhancing IFN-γ production by T cells. Additionally, the PSA-3A agonist was shown to induce higher levels of T cell activation, as compared with the PSA-3 peptide, in an in vivo model using HLA-A2.1/Kb transgenic mice (strain reported by A. Vitiello et al., 1991, J. Exp. Med. 173:1007–1015; V. H. Engelhard et al., 1991, J. Immunol.6:1226–1232). Accordingly, the PSA-3A agonist epitope of this invention is useful for both peptide-mediated and vector-mediated immunotherapy protocols for prostate cancer.

SUMMARY OF THE INVENTION

The invention provides isolated PSA-3 agonist peptides (e.g., SEQ ID NO:3–SEQ ID NO:5), as well as polypeptides (e.g., PSA polypeptides) comprising one or more of these peptides, and fragments and variants thereof. Also provided are methods of making these peptides and polypeptides.

The invention also provides isolated nucleic acids (e.g., SEQ ID NO:20–SEQ ID NO:22) encoding PSA-3 agonist peptides, polypeptides (e.g., PSA polypeptides), or fragments or variants thereof. This invention also provides probes, primers, and vectors comprising these nucleotide sequences, as well as host cells comprising these vectors. Also provided are methods of making these nucleic acids, as well as methods for making the probes, primers, vectors, and host cells of the invention.

The invention also provides antibodies and antibody fragments that bind to PSA-3 agonist peptides (e.g., SEQ ID NO:3SEQ ID NO:5), or polypeptides (e.g., PSA polypeptides) comprising these peptides, or variants, or fragments thereof. In particular, the invention provides polyclonal and monoclonal antibodies and antibody fragments that bind to the PSA-3 agonist peptides and polypeptides disclosed herein. The invention also provides methods of making these antibodies and antibody fragments.

The invention also provides methods of identifying test agents that can be used as drugs to further enhance immunoreactivity to PSA-3 agonist peptides. Such agents may act as mimetics of PSA-3 agonist peptides, or may enhance the formation or stability of peptide-HLA complexes.

The invention also provides diagnostic reagents comprising antibodies or antibody fragments that bind to PSA-3 agonist peptides, polypeptides, or fragments or variants thereof. Further provided are diagnostic reagents comprising PSA-3 agonist polynucleotides. Also provided are methods of using these reagents to monitor the vector-based, cell-based, and or peptide-based immunotherapies of the invention.

The invention also provides pharmaceutical compositions comprising one or more PSA-3 agonist peptides, PSA-3 agonist-modified vectors, or PSA-3 agonist-modified host cells. The invention further provides methods of administration of these pharmaceutical compositions for the treatment of prostate cancer. Such treatments include vector-mediated, cell-mediated, and peptide-mediated immunotherapies, and combinations thereof. The treatments of the invention can be used alone, or in conjunction with traditional cancer therapies, e.g., surgery, radiation therapy, and/or chemotherapy.

Additional objects and advantages afforded by this invention will be apparent from the detailed description and exemplification herein below.

BRIEF DESCRIPTION OF THE FIGURES

The appended drawings of the figures are presented to further describe the invention and to assist in its understanding through clarification of its various aspects.

FIG. 2. Comparison of the stability of the complex of the PSA-3 or PSA-3A peptide with HLA-A2. T2A2 cells were incubated with PSA-3 (open squares) or PSA-3A (closed squares) peptide at a concentration of 50 μg/ml overnight and then washed free of unbound peptide and incubated with brefeldin A to block delivery of new class I molecules to cell surface. At indicated times, cells were stained for the presence of surface peptide-HLA-A2 complexes. Results are expressed in relative % binding as compared to 100% binding at time zero.

FIGS. 3A–3B. Cytotoxicity of the T-PSA-3A T cell line derived by pulsing PBMCs with the PSA-3A peptide (FIG. 3A), and the T-PSA-3 T cell line derived by pulsing PBMCs with the PSA-3 peptide (FIG. 3B). Target cells were C1 R-A2 cells pulsed with either PSA-3A (solid squares) or PSA-3 (solid circles) peptide at a concentration of 25 μg/ml for in vitro stimulation (IVS-3) at various E:T (Effector: target) ratios. C1 R-A2 cells with no peptide (open squares) were also tested. Cytotoxic T lymphocyte (CTL) activity was determined in an 18-h $^{111}$In release assay.

FIGS. 4A–4B. Cytotoxicity of the T-PSA-3A T cell line (FIG. 4A), and the T-PSA-3 T cell line FIG. 4B), against C1 R-A2 cells pulsed with increasing concentration of PSA-3A (solid squares), or PSA-3 (open circles) peptide at IVS-3. E:T ratios=25:1. CTL activity was determined in an 18-h $^{111}$In release assay.

FIG. 5A: T-PSA-3 cells stimulated with B cells with no peptide; FIG. 5B: T-PSA-3 cells stimulated with B cells pulsed with PSA-3 peptide; FIG. 5C: T-PSA-3 cells stimulated with B cells pulsed with PSA-3A peptide. Numbers in each histogram indicate percent of apoptotic cells (cells above line) as described in the Examples section.

Figure 6A:
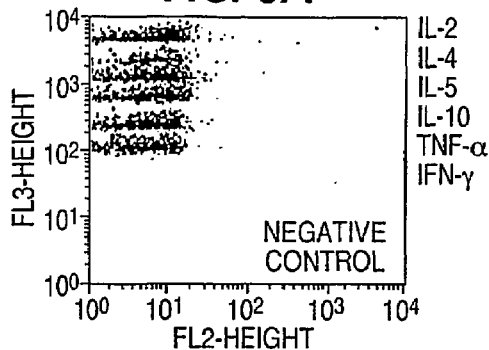
FIGS. 6A–6F. Cytometric Bead Array assay for the production of cytokines by peptide-stimulated T cells. The production of IL-2, IL-4, IL-5, IL-10, TNF-α, and IFN-γ (from top to bottom from each figure) was analyzed. Standards at concentrations of each cytokine at 0 pg/ml (FIG.
Figure 6D:
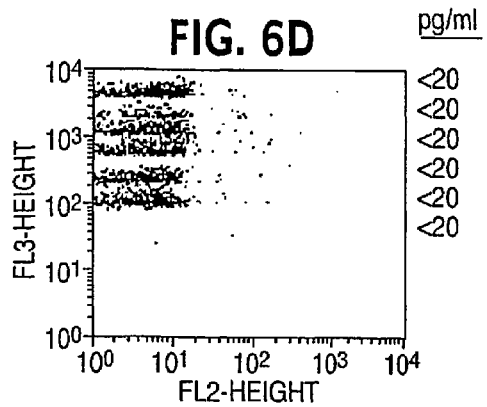
Figure 6B:
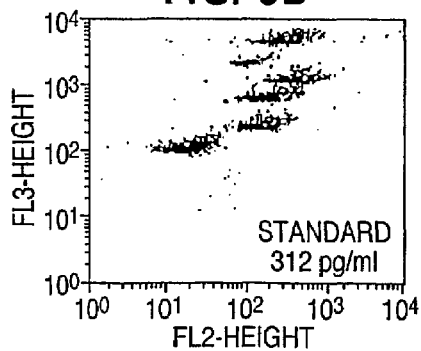
Figure 6E:
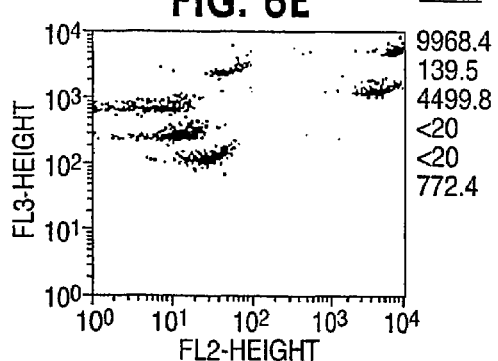
Figure 6C:
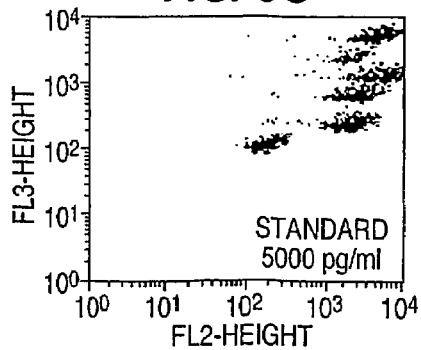
Figure 6F:
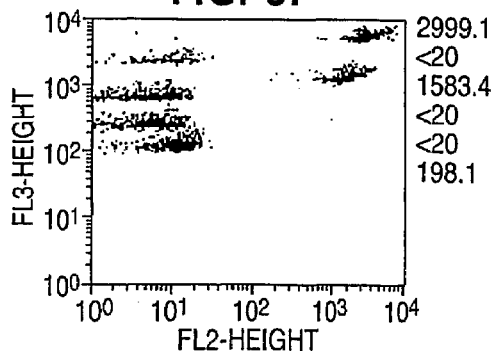

6A), 312 pg/ml (FIG. 6B), and 5000 pg/ml (FIG. 6C) were used to determine the concentrations of these six cytokines in the samples. Supernatant obtained from T-PSA-3 cells+ APC (autologous B cells) with no peptide (FIG. 6D). Supernatant obtained from T-PSA-3+APC+PSA3A (FIG. 6E). Supernatant obtained from T-PSA-3+APC+PSA-3 (FIG. 6F).

FIGS. 7A–7H. PSA polypeptides. FIGS. 7A–7B: precursor (SEQ ID NO:23) and mature (SEQ ID NO:24) PSA sequences. FIGS. 7C–7D: precursor (SEQ ID NO:25) and mature (SEQ ID NO:26) PSA sequences comprising the PSA-3 (1-155) peptide. FIGS. 7E–7F: precursor (SEQ ID NO:27) and mature (SEQ ID NO:28) PSA sequences comprising the PSA-3 (Y154) peptide. FIGS. 7G–7H: precursor (SEQ ID NO:29) and mature (SEQ ID NO:30) PSA sequences comprising the PSA-3 (L155/Y154) peptide. PSA-3 and PSA-3 agonist peptide sequences are underlined. Amino acid changes are shown in italics.

DETAILED DESCRIPTION OF THE PREFERRED EMBODIMENTS

Use of the terns "SEQ ID NO:3–SEQ ID NO:5" etc., is intended, for convenience, to refer to each individual SEQ ID NO. individually, and is not intended to refer to the sequences collectively. The invention encompasses each sequence individually, as well as any combination thereof.

"Nucleic acid or "polynucleotide" as used herein refers to purine- and pyrimidine-containing polymers of any length, either polyribonucleotides or polydeoxyribonucleotide or mixed polyribo-polydeoxyribonucleotides. This includes single-and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases. Polynucleotides, e.g., oligonucleotides, include naturally-occurring species or synthetic species formed from naturally-occurring subunits or their close homologs. The term may also refer to moieties that function similarly to polynucleotides, but have normaturally-occurring portions. Thus, polynucleotides may have altered sugar moieties or inter-sugar linkages. Exemplary among these are phosphorothioate and other sulfur containing species which are known in the art.

A "coding sequence" or a "protein-coding sequence" is a polynucleotide sequence capable of being transcribed into mRNA and/or capable of being translated into a polypeptide. The boundaries of the coding sequence are typically determined by a translation start codon at the 5'-terminus and a translation stop codon at the 3'-terminus.

A "complement" or "complementary sequence" of a nucleic acid sequence as used herein refers to the antisense sequence that participates in Watson-Crick base-pairing with the original sequence.

A "probe" or "primer" refers to a nucleic acid or oligonucleotide that forms a hybrid structure with a sequence in a target region due to complementarily of at least one sequence in the probe or primer with a sequence in the target region.

The term "vector" as used herein refers to a nucleic acid molecule capable of replicating another nucleic acid to which it has been linked. A vector, for example, can be a plasmid, recombinant virus or transposon.

"Host" includes prokaryotes and eukaryotes. The term includes an organism or cell that is the recipient of a replicable vector.

"Isolated", as used herein, refers to nucleic or amino acid sequences that are at least 60% free, preferably 75% free, and most preferably 90% free from other components with which they are naturally associated.

As used herein, the terms "protein" and "polypeptide" are synonymous. "Peptides" are defined as fragments or portions of polypeptides, preferably fragments or portions having at least one functional activity (e.g., binding or antigenic activity) as the complete polypeptide sequence. "Amino acid sequences" may correspond to peptides or polypeptides.

The term "antigenic" refers to the ability of a molecule (e.g., a polypeptide or peptide) to bind to its specific antibody, or an antibody fragment, with sufficiently high affinity to form a detectable antigen-antibody complex.

A "sample" as used herein refers to a biological sample, such as, for example, tissue or fluid isolated from an individual (including, without limitation, plasma, serum, cerebrospinal fluid, lymph, tears, saliva, milk, pus, and tissue exudates and secretions) or from in vitro cell culture constituents, as well as samples obtained from, for example, a laboratory procedure.

General descriptions of the foregoing terms and others are known in the art. See, e.g., Roitt et al., 1989, *Immunology*, $2^{nd}$ Edition, C. V. Mosby Company, New York; Male et al., 1991, *Advanced Immunology*, $2^{nd}$ Edition, Grower Medical Publishing, New York.

Nucleic Acids

This invention relates to isolated nucleic acids comprising nucleotide sequences (e.g., SEQ ID NO:20–SEQ ID NO:22) encoding one or more PSA-3 agonist peptides, PSA polypeptides comprising these peptides, or fragments or variants thereof. Such nucleic acids may be single stranded or double stranded, and may include DNA or RNA molecules (e.g., DNA, DNA/DNA, RNA, or RNA/DNA) comprising 15, 18, 21, 24, 30 or more contiguous nucleotides, or complementary sequences thereof. Closely related nucleic acid variants are also included as part of this invention, as well as recombinant nucleic acids encoding a PSA-3 agonist peptide containing one or more substitutions, deletions, or additions as described in detail herein below. Preferably, nucleic acids comprising variant sequences maintain their desired function (e.g., expression, etc.). In a preferred embodiment, this invention is directed to at least 24 contiguous nucleotides of a nucleic acid sequence encoding a PSA-3 agonist peptide.

In accordance with this invention, polynucleotide variations are selected from the group consisting of at least one nucleotide deletion, substitution, including transition and transversion, insertion, or modification (e.g., via RNA or DNA analogs). Variations may occur at the 5' or 3' terminal positions of the reference nucleotide sequence or anywhere between those terminal positions, interspersed either individually among the nucleotides in the reference sequence or in one or more contiguous groups within the reference sequence. Variations of a polynucleotide sequence encoding a PSA-3 agonist peptide may create, nonsense, missense, or frameshift mutations in the coding sequence, and thereby alter the encoded peptide. However, variations may also create silent mutations in the coding sequence and leave the encoded peptide unchanged.

Silent mutations in the coding sequence result from the degeneracy (i.e., redundancy) of the genetic code, whereby more than one codon can encode the same amino acid residue. In particular, for the agonist peptides VLSNDV-CAQV (SEQ ID NO:3), YISNDVCAQV (SEQ ID NO:4), and YLSNDVCAQV (SEQ ID NO:5), valine can be encoded by GTT, GTC, GTA, or GTG; leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA. Tables showing the standard genetic code can be found in various sources (e.g., L. Stryer, 1988, *Biochemistry*, 3$^{rd}$ *Edition, W.H.* Freeman and Co., NY).

Variant nucleic acids, including DNA or RNA, can be detected and isolated by hybridization under high stringency conditions or moderate stringency conditions, for example, which are chosen to prevent hybridization of nucleic acids having non-complementary sequences. "Stringency conditions" for hybridizations is a term of art which refers to the conditions of temperature and buffer concentration which permit hybridization of a particular nucleic acid to another nucleic acid in which the first nucleic acid may be perfectly complementary to the second, or the first and second may share some degree of complementarity which is less than perfect.

For example, certain high stringency conditions can be used which distinguish perfectly complementary nucleic acids from those of less complementarity. High, moderate, and low stringency conditions for nucleic acid hybridizations are explained in F. M. Ausubel et al. (eds), 1995, *Current Protocols in Molecular Biology*, John Wiley and Sons, Inc., New York, N.Y., the teachings of which are hereby incorporated by reference. In particular, see pages 2.10.1–2.10.16 (especially pages 2.10.8–2.10.11) and pages 6.3.1–6.3.6. The exact conditions which determine the stringency of hybridization depend not only on ionic strength, temperature and the concentration of destabilizing agents such as formamide, but also on factors such as the length of the nucleic acid sequence, base composition, percent mismatch between hybridizing sequences and the frequency of occurrence of subsets of that sequence within other non-identical sequences. Thus, high or moderate stringency conditions can be determined empirically.

High stringency hybridization conditions are typically carried out at 65 to 68° C. in 0.1×SSC and 0.1% SDS. Highly stringent conditions allow hybridization of nucleic acid molecules having about 95 to 100% sequence identity. Moderate stringency hybridization conditions are typically carried out at 50 to 65° C. in 1×SSC and 0.1% SDS. Moderate stringency conditions allow hybridization of sequences having at least 80 to 95% nucleotide sequence identity. Low stringency hybridization conditions are typically carried out at 40 to 50° C. in 6×SSC and 0.1% SDS. Low stringency hybridization conditions allow detection of specific hybridization of nucleic acid molecules having at least 50 to 80% nucleotide sequence identity. Examples of high, medium, and low stringency conditions can be found in Sambrook et al., 1989. Exemplary conditions are also described in M. H. Krause and S. A. Aaronson, 1991, *Methods in Enzymology*, 200:546556; Ausubel et al., 1995. It is to be understood that the low, moderate, and high stringency hybridization/washing conditions may be varied using a variety of ingredients, buffers, and temperatures well known to and practiced by the skilled practitioner.

The nucleic acid sequences of this invention may be derived from a variety of sources including genomic DNA, cDNA, synthetic DNA, synthetic RNA, or combinations thereof. The sequences may be obtained in any of several ways. For example, the polymerase chain reaction (PCR) method can be used to produce the nucleic acids of the invention, using either RNA (e.g., mRNA or synthetic RNA) or DNA (e.g., genomic DNA or synthetic DNA) as templates. Primers used for PCR can be synthesized using the sequence information provided herein and can further be designed to introduce appropriate new restriction sites, if desirable, to facilitate incorporation into a given vector for recombinant expression.

The nucleic acids described herein can be used in the methods of this invention for production of proteins or peptides, through incorporation (e.g., tranformation, transfection, or integration) into cells, tissues, or organisms. In one embodiment, DNA containing all or part of the coding sequence for a PSA-3 agonist peptide, or a fragment thereof, is incorporated into a vector for expression of the encoded polypeptide or peptide in suitable host cells. Preferably, the encoded polypeptide or peptide is capable of normal activity, such as antigenic or binding activity.

The nucleic acids of this invention also find use as primers and probes for, e.g., analysis of host cells containing PSA-3A vectors, or monitoring patients undergoing treatment with PSA-3A vectors or PSA-3A-modified host cells. As examples, probes can be used in nucleic acid hybridization experiments, whereas primers can be used in PCR-based experiments. The probes of this invention may be DNA or RNA. The probes and primers of the invention may comprise all or a portion of the nucleotide sequence of the PSA-3 agonist nucleic acids (e.g., SEQ ID NO:20–SEQ ID NO:22), or a complementary sequence thereof, and may include promoter, enhancer elements, and additional PSA coding sequences.

Viral and Non-Viral Vectors

In various embodiments, one or more PSA-3 agonist peptides (e.g., SEQ ID NO:3–SEQ ID NO:5), or PSA polypeptides comprising these peptides (e.g., SEQ ID NO:25–SEQ ID NO:30), may be encoded by a viral or non-viral vector. A number of viral vectors have been constructed, including polyoma, i.e., SV40 (Madzak et al., 1992, *J. Gen. Virol.*, 73:15331536), adenovirus (Berkner, 1992, *Cur. Top. Microbiol. Immunol.*, 158:39–6; Berliner et al., 1988, *Bio Techniques*, 6:616–629; Gorziglia et al., 1992, *J. Virol.*, 66:4407–4412; Quantin et al., 1992, *Proc. Nad. Acad. Sci. USA*, 89:2581–2584; Rosenfeld et al., 1992, *Cell*, 68:143–155; Wilkinson et al., 1992, *Nucl. Acids Res.*, 20:2233–2239; Stratford-Perricaudet et al., 1990, *Hum. Gene Ther.*, 1:241–256), vaccinia virus (Mackett et al., 1992, *Biotechnology*, 24:495–499), adeno-associated virus (Muzyczka, 1992, *Curr. Top. Microbiol. Immunol.*, 158:91–123; ON et al., 1990, Gene, 89:279–282), herpes viruses including HSV and EBV (Margolskee, 1992, *Curr. Top. Microbiol. Immunol.*, 158:67–90; Johnson et al., 1992, *J. Virol.*, 66:29522965; Fink et al., 1992, *Hum. Gene Ther.* 3:11–19; Breakfield et al., 1987, *Mol. Neurobiol.*, 1:337–371; Fresse et al., 1990, *Biochem. Pharmacol.*, 40:2189–2199), Sindbis viruses (H. Herweijer et al., 1995, Human Gene Therapy 6:1161–1167; U.S. Pat. Nos. 5,091,309 and 5,2217,879), alphaviruses (S. Schlesinger, 1993, Trends Biotechnol. 11:18–22; I. Frolov et al., 1996, Proc. Natl. Acad. Sci. USA 93:11371–11377) and retroviruses of avian (Brandyopadhyay et al., 1984, *Mol. Cell Biol.*, 4:749–754; Petropouplos et al., 1992, J. Virol., 66:3391–3397), murine (Miller, 1992, *Curr. Top. Microbiol.* Immunol., 158:1–24; Miller et al., 1985, Mol. Cell Biol., 5:431–437; Sorge et al., 1984, Mol. Cell Biol., 4:1730–1737; Mann et al., 1985, J. Virol., 54:401–407), and human origin (Page et al., 1990, J. Virol., 64:5370–5276; Buchschalcher et al., 1992, J. Virol., 66:2731–2739). Baculovirus (*Autographa californica* multinuclear polyhedrosis virus; AcMNPV) vectors are also known in the art, and may be obtained from commercial sources (e.g., PharMingen, San Diego, Calif.; Protein Sciences Corp., Meriden, Conn.; Stratagene, La Jolla, Calif.). Many human gene therapy protocols have been based on disabled murine retroviruses.

In addition, non-viral vectors can be transferred to hosts or host cells by well established methods, including chemical techniques such as calcium phosphate coprecipitation (Graham et al., 1973, *Virology*, 52:456–467; Pellicer et al., 1980, *Science*, 209:1414–1422), mechanical techniques, for example microinjection (Anderson et al., 1980, *Proc. Natl. Acad. Sci.* USA, 77:5399–5403; Gordon et al., 1980, *Proc. Natl. Acad. Sci.* USA, 77:7380–7384; Brinster et al., 1981, *Cell*, 27:223–231; Constantini et al., 1981, *Nature*, 294: 92–94), membrane fusion-mediated transfer via liposomes (U.S. Pat. No. 5,908,777 to Lee et al.; Felgner et al., 1987, *Proc. Natl. Acad. Sci.* USA, 84:7413–7417; Wang et al., 1989, *Biochemistry*, 28:9508–9514; Kaneda et al., 1989, *J. Biol. Chem.*, 264:12126–12129; Stewart et al., 1992, *Hum. Gene Ther.*, 3:267–275; Nabel et al., 1990, *Science*, 249: 1285–1288; Lim et al., 1992, *Circulation*, 83:2007–2011, and direct DNA uptake and receptor-mediated DNA transfer (Wolff et al., 1990, *Science*, 247:14651468; Wu et al., 1991, *BioTechniques*, 11:474–485; Zenke et al., 1990, *Proc. Nat. Acad. Sci.* USA, 87:3655–3659; Wu et al., 1989, *J. Biol. Chem.*, 264:16985–16987; Wolff et al., 1991, *BioTechniques*, 11:474–485; Wagner et al., 1991, *Proc. Natl. Acad. Sci.* USA, 88:4255–4259; Cotten et al., 1990, *Proc. Nat. Acad. Sci.* USA, 87:4033–4037; Curiel et al., 1991, *Proc. Natl. Acad. Sci.* USA, 88:8850–8854; Curiel et al., 1991, *Hum. Gene Ther.* 3:147154).

Basic techniques for preparing recombinant DNA viruses containing a heterologous DNA sequence encoding the PSA-3 agonist peptide, or a PSA polypeptide comprising this peptide, are known to the skilled artisan. Such techniques involve, for example, homologous recombination between the viral DNA sequences flanking the DNA sequence in a donor plasmid and homologous sequences present in the parental virus (Mackett et al., 1982, *Proc. Natl. Acad. Sci*. USA 79:7415–7419). In particular, recombinant viral vectors such as a poxyiral vector can be used in delivering the gene. The vector can be constructed for example by steps known in the art, e.g. analogous to the methods for creating synthetic recombinants of the fowlpox virus described in U.S. Pat. No. 5,093,258, the disclosure of which is incorporated herein by reference. Other techniques include using a unique restriction endonuclease site that is naturally present or artificially inserted in the parental viral vector to insert the heterologous DNA.

Pox viruses useful in practicing the present invention include orthopox, suipox, avipox, and capripox virus. Orthopox include vaccinia, ectromelia, and raccoon pox. The preferred orthopox is vaccinia. Avipox includes fowlpox, canary pox and pigeon pox. The preferred avipox is fowlpox. Capripox include goatpox and sheeppox. A preferred suipox is swinepox. Examples of pox viral vectors for expression of PSA were provided in, for example, U.S. Pat. No. 6,165,460 to Schlom, et al. Other viral vectors that can be used include other DNA viruses such as herpes virus and adenoviruses, and RNA viruses such as retroviruses and polio. In some cases, vaccinia viral vectors may elicit a strong antibody response. Thus, while numerous boosts with vaccinia vectors are possible, its repeated use may not be preferred in certain instances. However, this sensitivity problem can be minimized by using pox from different genera for boosts. Preferably, when the first or initial pox virus vector is vaccinia, the second and subsequent pox virus vectors are selected from the pox viruses from a different genus such as suipox, avipox, capripox or an orthopox immunogenically distinct from vaccinia.

In general, the DNA donor vector contains the following elements: (i) a prokaryotic origin of replication, so that the vector may be amplified in a prokaryotic host; (ii) a gene encoding a marker which allows selection of prokaryotic host cells that contain the vector (e.g., a gene encoding antibiotic resistance); (iii) at least one DNA sequence encoding the PSA-3 agonist peptide, or a PSA polypeptide comprising this peptide, located adjacent to a transcriptional promoter capable of directing the expression of the sequence; and (iv) DNA sequences homologous to the region of the parent virus genome where the foreign gene(s) will be inserted, flanking the construct of element (iii). Methods for constructing donor plasmids for the introduction of multiple foreign genes into pox virus are described in WO91/19803, the techniques of which are incorporated herein by reference.

Generally, DNA fragments for construction of the donor vector, including fragments containing transcriptional promoters and fragments containing sequences homologous to the region of the parent virus genome into which foreign DNA sequences are to be inserted, can be obtained from genomic DNA or cloned DNA fragments. The donor plasmids can be mono, di-, or multivalent (i.e., can contain one or more inserted foreign DNA sequences). The donor vector preferably contains an additional gene that encodes a marker that will allow identification of recombinant viruses containing inserted foreign DNA. Several types of marker genes can be used to permit the identification and isolation of recombinant viruses. These include genes that encode antibiotic or chemical resistance (e.g., see Spyropoulos et al., 1988, *J. Virol.* 62:1046; Falkner and Moss, 1988, *J. Virol.* 62:1849; Franke et al., 1985, *Mol. Cell. Biol.* 5:1918), as well as genes such as the *E. coli* lacZ gene, that permit identification of recombinant viral plaques by colorimetric assay (Panicali et al., 1986, *Gene* 47:193–199).

In accordance with established methods, the DNA gene sequence to be inserted into the virus can be placed into a donor plasmid, e.g., an *E. coli* plasmid construct, into which DNA homologous to a section of DNA such as that of the insertion site of the poxvirus where the DNA is to be inserted has been inserted. Separately the DNA gene sequence to be inserted is ligated to a promoter. The promoter-gene linkage is positioned in the plasmid construct so that the promoter-gene linkage is flanked on both ends by DNA homologous to a DNA sequence flanking a region of pox DNA that is the desired insertion region. With a parental pox viral vector, a pox promoter is used. The resulting plasmid construct is then amplified by growth within *E. coli* bacteria and isolated. Next, the isolated plasmid containing the DNA gene sequence to be inserted is transfected into a cell culture, e.g., chick embryo fibroblasts, along with the parental virus, e.g., poxvirus. Recombination between homologous pox DNA in the plasmid and the viral genome respectively results in a recombinant poxvirus modified by the presence of the promoter-gene construct in its genome, at a site that does not affect virus viability.

As noted above, the DNA sequence is inserted into a region (insertion region), in the virus that does not affect virus viability of the resultant recombinant virus. The skilled artisan can readily identify such regions in a virus by, for example, randomly testing segments of virus DNA for regions that allow recombinant formation without seriously affecting virus viability of the recombinant. One region that can readily be used and is present in many viruses is the thymidine kinase (TK) gene. The TK gene has been found in all pox virus genomes examined, including leporipoxvirus (Upton et al., 1986, *J. Virology* 60:920); shope fibromavirus; capripoxvirus (Gershon et al., 1989, J. *Gen. Virol.* 70:525) Kenya sheep-1; orthopoxvirus (Weir et al., 1983, *J. Virol.* 46:530) vaccinia (Esposito et al., 1984, *Virology* 135:561); monkeypox and variola virus (Hruby et al., 1983, PNAS 80:3411) vaccinia (Kilpatrick et al., 1985, *Virology* 143: 399); Yaba monkey tumor virus; avipoxvirus (Binns et al., 1988, J. *Gen. Virol.* 69:1275); fowipox; (Boyle et al., 1987, *Virology* 156:355); fowlpox (Schnitzlein et al., 1988, J. *Virological Methods* 20:341); fowlpox, quailpox; entomopox (Lytvyn et al., 1992, J. *Gen. Virol.* 73:3235-3240).

In vaccinia, in addition to the TK region, other insertion regions include, for example, the Hindlll M fragment. In fowlpox, in addition to the TK region, other insertion regions include, for example, the BamHI J fragment (Jenkins et al., 1991, AIDS *Research and Human Retroviruses* 7:991–998) the ECORI-Hindlll fragment, EcoRV-Hindlll fragment, BamHl fragment and the Hindlll fragment set forth in EPO Application No. 0 308220 A1 (see also Calvert et al., 1993, *J. Virol.* 67:3069–3076; Taylor et al., 1988, *Vaccine* 6:497–503; Spehner et al., 1990; Boursnell et al., 1990, J. *Gen. Virol.* 71:621–628).

In swinepox preferred insertion sites include the thymidine kinase gene region. In addition to the requirement that the gene be inserted into an insertion region, successful expression of the inserted gene by the modified poxvirus requires the presence of a promoter operably linked to the desired gene, i.e., in the proper relationship to the inserted gene. The promoter must be placed so that it is located upstream from the gene to be expressed. Promoters are well known in the art and can readily be selected depending on the host and the cell type you wish to target. Preferably, in poxviruses, pox viral promoters are used, such as the vaccinia 7.5K, 40K or fowlpox promoters such as FPV C1A. Enhancer elements can also be used in combination to increase the level of expression. Furthermore, the use of inducible promoters, which are also well known in the art, may be advantageous.

Homologous recombination between donor plasmid DNA and viral DNA in an infected cell results in the formation of recombinant viruses that incorporate the desired elements. Appropriate host cells for in vivo recombination are generally eukaryotic cells that can be infected by the virus and transfected by the plasmid vector. Examples of such cells suitable for use with a pox virus are chick embryo fibroblasts, HuTK143 (human) cells, and CV-1 and BSC-40 (both monkey kidney) cells. Infection of cells with pox virus and transfection of these cells with plasmid vectors is accomplished by techniques standard in the art (Panicali and Paoletti, U.S. Pat. No. 4,603,112, W089/03429).

Following in vivo recombination, recombinant viral progeny can be identified by one of several techniques. For example, if the DNA donor vector is designed to insert foreign genes into the parent virus thymidine kinase (TK) gene, viruses containing integrated DNA will be TK- and can be selected on this basis (Mackett et al., 1982, *Proc. Natl. Acad. Sci. USA* 79:7415). Alternatively, co-integration of a gene encoding a marker or indicator gene with the foreign gene(s) of interest, as described above, can be used to identify recombinant progeny. One preferred indicator gene is the *E. coli* lacZ gene. Recombinant viruses expressing beta-galactosidase can be selected using a chromogenic substrate for the enzyme (Panicali et al., 1986, Gene 47:193). Once a recombinant virus has been identified, a variety of well-known methods can be used to assay the expression of the PSA sequence (e.g., PSA-3A) encoded by the inserted DNA fragment. These methods include black plaque assay (an in situ enzyme immunoassay performed on viral plaques), Western blot analysis, radioimmunoprecipitation (RIPA), and enzyme immunoassay (EIA).

Peptides and Polypeptides

A further aspect of this invention pertains to isolated PSA-3 agonist peptides (e.g., SEQ ID NO:3–SEQ ID NO:5), and PSA polypeptides comprising these peptides (e.g., SEQ ID NO:25–SEQ ID NO:30). The peptides and polypeptides of this invention can be isolated, synthetic, or recombinant. This invention encompasses PSA-3 agonist peptides and PSA polypeptides comprising these peptides, and fragments and functional equivalents thereof. The term "functional equivalent" is intended to include proteins which differ in amino acid sequence from the polypeptides or peptides of the invention, but where such differences result in a modified protein which performs at least one characteristic function of the polypeptide or peptide (e.g., binding or antigenic activity). For example, a functional equivalent of a polypeptide or peptide may have a variation such as a substitution, addition, deletion, or modification (e.g., phosphorylation, labeling, etc.) of an amino acid residue that is not directly involved in the function of the polypeptide or peptide.

It is also possible to vary the structure of a PSA-3 agonist peptide, or a PSA polypeptide comprising this peptide, for such purposes as increasing solubility, enhancing activity, antigenicity, or stability (e.g., shelf life ex vivo and resistance to proteolytic degradation in vivo) of the molecule. Such variants are considered functional equivalents of the polypeptides and peptides as defined herein. Preferably, polypeptides and peptides are modified so that they retain activity. Those residues shown to be essential for activity can be altered by replacing the essential amino acid with another, preferably similar amino acid residue (a conservative substitution) whose presence is shown to enhance, diminish, but not eliminate, or not effect function. In addition, those amino acid residues that are not essential for binding or other activity can be altered by being replaced by another amino acid whose incorporation may enhance, diminish, or not effect reactivity.

Polypeptide and peptide variants include mutants differing by the addition, deletion, or substitution of one or more amino acid residues. Also included are modified polypeptides and peptides in which one or more residues are modified, and mutants comprising one or more modified residues. Useful modifications may include phosphorylation, sulfation, reduction/alkylation (Tarr, 1986, *Methods of Protein Microcharacterization*, J. E. Silver, Ed., Humana Press, Clifton, N.J., pp. 155–194); acylation (Tarr, supra); chemical coupling (Mishell and Shiigi (Eds),1980, *Selected Methods in Cellular Immunology*, W H Freeman, San Francisco, Calif.; U.S. Pat. No. 4,939,239); and mild formalin treatment (Marsh, 1971, *Int. Arch. of Allergy and Appl. Immunol.* 41:199–215). Additionally, D-amino acids, non-natural amino acids, or non-amino acid analogs can be substituted or added to produce a modified polypeptide. Furthermore, the polypeptides disclosed herein can be modified using polyethylene glycol (PEG) according to known methods (S. I. Wie et al., 1981, *Int. Arch. Allergy Appl. Immunol.* 64(1):8499) to produce a protein conjugated with PEG. In addition, PEG can be added during chemical synthesis of the protein. Modifications or sequence variations may occur at the amino- or carboxy-terminal positions of the reference polypeptide sequence or anywhere between those terminal positions, interspersed either individually among the amino acids in the reference sequence or in one or more contiguous groups within the reference sequence.

Polypeptides or peptides may also be modified with a label capable of providing a detectable signal, either directly or indirectly, including, but not limited to, radioisotope, fluorescent, and enzyme labels. Fluorescent labels include, for example, CyTM3, CyTM5, Alexa, BODIPY, fluorescein (e.g., Fluor X, DTAF, and FITC), rhodamine (e.g., TRITC), auramine, Texas Red, AMCA blue, and Lucifer Yellow. Preferred isotope labels include $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re. Preferred enzyme labels include peroxidase, β-glucuronidase, β-D-glucosidase, β-Dgalactosidase, urease, glucose oxidase plus peroxidase, and alkaline phosphatase (see, e.g., U.S. Pat. Nos. 3,654,090; 3,850,752 and 4,016,043). Enzymes can be conjugated by reaction with bridging molecules such as carbodiimides, diisocyanates, glutaraldehyde, and the like. Enzyme labels can be detected visually, or measured by calorimetric, spectrophotometric, fluorospectrophotometric, amperometric, or gasometric techniques. Other labeling systems, such as avidin/biotin, Tyramide Signal Amplification (TSATM), are known in the art, and are commercially available (see, e.g., ABC kit, Vector Laboratories, Inc., Burlingame, Calif.; NEN® Life Science Products, Inc., Boston, Mass.).

In accordance with this invention, polypeptide or peptide sequences may be identical to PSA-3 agonist peptides, or PSA polypeptides comprising these peptides, or may include up to a certain integer number of amino acid alterations. Amino acid alterations are selected from the group consisting of at least one amino acid deletion, substitution, including conservative and non-conservative substitution, or insertion. Thus, polypeptide and peptide variants may have conservative changes, wherein a substituted amino acid has similar structural or chemical properties, e.g., replacement of leucine with isoleucine. More infrequently, a variant may have nonconservative changes, e.g., replacement of a glycine with a tryptophan. Guidance in determining which amino acid residues can be substituted, inserted, or deleted without abolishing biological or immunological activity can be determined using computer programs well known in the art, for example, DNASTAR software (DNASTAR, Inc., Madison, Wis.). As non-limiting examples, conservative substitutions in a PSA-3 agonist amino acid sequence can be made in accordance with the following table:

| Original Residue | Conservative Substitution (s) | Original Residue | Conservative Substitution s |
|---|---|---|---|
| Ala | Ser | Leu | Ile, Val |
| Arg | Lys | Lys | Arg, Gln, Glu |
| Asn | Gln, His | Met | Leu, Ile |
| Asp | Glu | Phe | Met, Leu, Tyr |
| Cys | Ser | Ser | Thr |
| Gln | Asn | Thr | Ser |
| Glu | Asp | Trp | Tyr |
| Gly | Pro | Tyr | Trp, Phe |
| His | Asn, Gln | Val | Ile, Leu |
| Ile | Leu, Val | | |

Preferably, PSA-3 agonist peptides (e.g., SEQ ID NO:3–SEQ ID NO:5) contain V or Y at position 1; L or M at position 2; and V or I at position 10. In preferred embodiments, PSA-3 agonist peptides do not include D, E, or P at position 1; D or E at position 3; R, K, H or A at position 4; P at position 5; R, K or H at position 7; D, E, R, K or H at position 8; R, K or H at position 9; or L at position 10.

Substantial changes in function or immunogenicity can be made by selecting substitutions that are less conservative than those shown in the table, above. For example, non-conservative substitutions can be made which more significantly affect the structure of the polypeptide in the area of the alteration, for example, the alpha-helical, or beta-sheet structure; the charge or hydrophobicity of the molecule at the target site; or the bulk of the side chain. The substitutions which generally are expected to produce the greatest changes in the polypeptide's properties are those where 1) a hydrophilic residue, e.g., seryl or threonyl, is substituted for (or by) a hydrophobic residue, e.g., leucyl, isoleucyl, phenylalanyl, valyl, or alanyl; 2) a cysteine or proline is substituted for (or by) any other residue; 3) a residue having an electropositive side chain, e.g., lysyl, arginyl, or histidyl, is substituted for (or by) an electronegative residue, e.g., glutamyl or aspartyl; or 4) a residue having a bulky side chain, e.g., phenylalanine, is substituted for (or by) a residue that does not have a side chain, e.g., glycine.

Sequence tags (e.g., epitope or protein tags) or amino acids, such as one or more lysines, can be added to the peptide sequences of the invention (e.g., at the N-terminal or C-terminal ends). Non-limiting examples of epitope tags include c-myc, haemagglutinin (HA), polyhistidine (6X-HIS) (SEQ ID NO:16), GLU-GLU, and DYKDDDDK (SEQ ID NO:17; FLAG®) tags. Non-limiting examples of protein tags include glutathione-S-transferase (GST), green fluorescent protein (GFP), and maltose binding protein (MBP). Sequence tags can be used for peptide purification or localization. Lysines can be used to increase peptide solubility or to allow for biotinylation.

The instant invention also provides aptamers of peptides of the instant invention. In a preferred embodiment, the invention provides aptamers of PSA-3 agonist peptides such as SEQ ID NO:3–SEQ ID NO:5. The instant aptamers are peptide or nucleic acid molecules that are capable of binding to a protein or other molecule, or mimic the three dimensional structure of the active portion of the peptides of the invention. Aptamers may be prepared by any known method, including synthetic, recombinant, and purification methods (*Nature* 1996 Apr. 11; 380(6574):548–50).

Production of Peptides and Polypeptides

Many conventional techniques in molecular biology, protein biochemistry, and immunology may be used to produce and isolate the PSA-3 agonist peptides (e.g., SEQ ID NO:3–SEQ ID NO:5), or PSA polypeptides comprising these peptides (e.g., SEQ ID NO:25–SEQ ID NO:30), for use with this invention. To obtain recombinant polypeptides and peptides, coding sequences may be cloned into any suitable vectors for expression in intact host cells or in cell-free translation systems by methods well known in the art (see Sambrook et al., 1989) and described herein. Alternately, peptides may be chemically synthesized by commercially available automated procedures. Following production, the polypeptides and peptides of this invention, including functional equivalents, may be isolated from wild-type or mutant cells (e.g., human cells or cell lines), from heterologous organisms or cells (e.g., bacteria, yeast, insect, plant, and mammalian cells), or from cell-free translation systems (e.g., wheat germ, microsomal membrane, or bacterial extracts) in which a coding sequence has been introduced and expressed. The polypeptides and peptides can also be isolated following synthetic chemistry.

In one aspect of the invention, DNA containing all or part of the coding sequence for PSA-3 agonist peptide (e.g., one or more of SEQ ID NO3–SEQ ID NO:5), or PSA polypeptide comprising this peptide, or variant thereof, is incorporated into a vector for expression of the encoded amino acid sequence in suitable host cells. Preferably, the encoded polypeptides, peptides, or their functional equivalents, are capable of activity (i.e., binding or antigenic activity). A large number of vectors, including bacterial, yeast, and mammalian vectors, have been described for replication and/or expression in various host cells or cell-free systems, and may be used for vector-based therapies as well as for simple cloning or protein expression.

As an example, a vector (e.g., expression vector) can comprise a nucleic acid encoding a PSA-3 agonist peptide, or PSA polypeptide comprising this peptide, as described herein, operably linked to at least one regulatory sequence. Regulatory sequences are known in the art and are selected to direct expression of the desired protein in an appropriate host cell. Accordingly, the term regulatory sequence includes promoters, enhancers and other expression control elements (see, e.g., D. V. Goeddel, 1990, *Methods Enzymol.* 185:3–7). Enhancer and other expression control sequences are described in *Enhancers and Eukaryotic Gene Expression,* 1983, Cold Spring Harbor Press, Cold Spring Harbor, N.Y. It should be understood that the design of the vector may depend on such factors as the choice of the host cell to be transfected and/or the type of polypeptide or peptide to be expressed.

Several regulatory elements (e.g., promoters) have been isolated and shown to be effective in the transcription and translation of heterologous proteins in the various hosts. Such regulatory regions, methods of isolation, manner of manipulation, etc. are known in the art. Non-limiting examples of bacterial promoters include the β-lactamase (penicillinase) promoter; lactose promoter; tryptophan (trp) promoter; araBAD (arabinose) operon promoter; lambda-derived $P_1$ promoter and N gene ribosome binding site; and the hybrid tac promoter derived from sequences of the trp and lac UV5 promoters. Non-limiting examples of yeast promoters include the 3phosphoglycerate kinase promoter, glyceraldehyde-3-phosphate dehydrogenase (GAPDH) promoter, galactokinase (GAL1) promoter, galactoepimerase promoter, and alcohol dehydrogenase (ADH1) promoter. Suitable promoters for mammalian cells include, without limitation, viral promoters, such as those from Simian Virus 40 (SV40), Rous sarcoma virus (RSV), adenovirus (ADV), and bovine papilloma virus (BPV). Preferred replication and inheritance systems include M 13, ColE1, SV40, baculovirus, lambda, adenovirus, CEN AIRS, 2 µm AIRS and the like. While vectors may replicate autonomously, they may also replicate by being inserted into the genome of the host cell, by methods well known in the art.

DNA sequences can be optimized, if desired, for more efficient expression in a given host organism or expression system. For example, codons can be altered to conform to the preferred codon usage in a given host cell or cell-free translation system using well-established techniques. Codon usage data can be obtained from publicly-available sources, for example, the Codon Usage Database at http://www.kazusa.or.jp/codon/. In addition, computer programs that translate amino acid sequence information into nucleotide sequence information in accordance with codon preferences (i.e., backtranslation programs) are widely available. See, for example, Backtranslate program from Genetics Computer Group (GCG), Accelrys, Inc., Madison, Wis.; and Backtranslation Applet from Entelechon GmbH, Regensburg, Germany. Thus, using the polypeptide and peptide sequences disclosed herein, one of ordinary skill in the art can design nucleic acids to yield optimal expression levels in the translation system or host cell of choice.

To obtain expression in eukaryotic cells, terminator sequences, polyadenylation sequences, and enhancer sequences that modulate gene expression may be required. Sequences that cause amplification of the gene may also be desirable. These sequences are well known in the art. Furthermore, sequences that facilitate secretion of the recombinant product from cells, including, but not limited to, bacteria, yeast, and animal cells, such as secretory signal sequences and/or preprotein or proprotein sequences, may also be included. Such sequences are well described in the art.

Expression and cloning vectors will likely contain a selectable marker, a gene encoding a protein necessary for survival or growth of a host cell transformed with the vector. The presence of this gene ensures growth of only those host cells that express the inserts. Typical selection genes encode proteins that 1) confer resistance to antibiotics or other toxic substances, e.g., ampicillin, neomycin, methotrexate, etc.; 2) complement auxotrophic deficiencies, or 3) supply critical nutrients not available from complex media, e.g., the gene encoding D-alanine racemase for Bacilli. Markers may be an inducible or non-inducible gene and will generally allow for positive selection. Non-limiting examples of markers include the ampicillin resistance marker (i.e., beta-lactamase), tetracycline resistance marker, neomycin/kanamycin resistance marker (i.e., neomycin phosphotransferase), dihydrofolate reductase, glutamine synthetase, and the like. The choice of the proper selectable marker will depend on the host cell, and appropriate markers for different hosts as understood by those of skill in the art.

Suitable vectors for use with this invention include, but are not limited to, pUC, pBluescript (Stratagene), pET (Novagen, Inc., Madison, Wis.), and pREP (Invitrogen) plasmids. Vectors can contain one or more replication and inheritance systems for cloning or expression, one or more markers for selection in the host, e.g., antibiotic resistance, and one or more expression cassettes. The inserted coding sequences can be synthesized by standard methods, isolated from natural sources, or prepared as hybrids. Ligation of the coding sequences to transcriptional regulatory elements (e.g., promoters, enhancers, and/or insulators) and/or to other amino acid encoding sequences can be carried out using established methods. Suitable cell-free expression systems for use with this invention include, without limitation, rabbit reticulocyte lysate, wheat germ extract, canine pancreatic microsomal membranes, *E. coli* S30 extract, and coupled transcription/translation systems (Promega Corp., Madison, Wis.). These systems allow the expression of recombinant polypeptides or peptides upon the addition of cloning vectors, DNA fragments, or RNA sequences containing protein-coding regions and appropriate promoter elements.

Non-limiting examples of suitable host cells include bacteria, archea, insect, fungi (e.g., yeast), plant, and animal cells (e.g., mammalian, especially human). Of particular interest are *Escherichia coli, Bacillus subtilis, Saccharomyces cerevisiae*, SF9 cells, C129 cells, 293 cells, *Neurospora*, and immortalized mammalian myeloid and lymphoid cell lines. Techniques for the propagation of mammalian cells in culture are well-known (see, Jakoby and Pastan (eds), 1979, *Cell Culture. Methods in Enzymology*, volume 58, Academic Press, Inc., Harcourt Brace Jovanovich, N.Y.). Examples of commonly used mammalian host cell lines are VERO and HeLa cells, CHO cells, and WI38, BHK, and COS cell lines, although it will be appreciated by the skilled practitioner that other cell lines may be used, e.g., to provide higher expression desirable glycosylation patterns, or other features.

Host cells can be transformed, transfected, or infected as appropriate by any suitable method including electroporation, calcium chloride-, lithium chloride-, lithium acetate/polyethylene glycol-, calcium phosphate-, DEAEdextran-, liposome-mediated DNA uptake, spheroplasting, injection, microinjection, microprojectile bombardment, phage infection, viral infection, or other established methods. Alternatively, vectors containing the nucleic acids of interest can be transcribed in vitro, and the resulting RNA introduced into the host cell by well-known methods, e.g., by injection (see, Kubo et al., 1988, *FEBS Letts.* 241:119). The cells into which have been introduced nucleic acids described above are meant to also include the progeny of such cells.

Nucleic acids encoding the PSA-3 agonist peptides, polypeptides comprising these peptides, or variants or fragments thereof, can be produced in large quantities by replication in a suitable host cell. Synthetic nucleic acid fragments comprising at least 15 contiguous bases coding for a desired peptide or polypeptide can be incorporated into recombinant nucleic acid constructs, e.g., DNA constructs, capable of introduction into and replication in a prokaryotic or eukaryotic cell. The most commonly used prokaryotic hosts are strains of *Escherichia coli*, although other prokaryotes, such as *Bacillus subtilis* or *Pseudomonas* may also be used. Also useful are mammalian or other eukaryotic host cells, such as those of yeast, filamentous fungi, plant, insect, or amphibian or avian species, may also be useful for isolation of the nucleic acids of the invention. The purification of nucleic acids produced by the methods of this invention is described, for example, in Sambrook et al., 1989; F. M. Ausubel et al., 1992, *Current Protocols in Molecular Biology*, J. Wiley and Sons, New York, N.Y.

The nucleic acids encoding the peptides or polypeptides of this invention can also be produced by chemical synthesis, e.g., by the phosphoramidite method described by Beaucage et al., 1981, *Tetra. Letts.* 22:1859–1862, or the triester method according to Matteucci et al., 1981, *J. Am. Chem. Soc.*, 103:3185, and can performed on commercial, automated oligonucleotide synthesizers. A double-stranded fragment may be obtained from the single-stranded product of chemical synthesis either by synthesizing the complementary strand and annealing the strands together under appropriate conditions or by adding the complementary strand using DNA polymerase with an appropriate primer sequence.

In another aspect of the invention, PSA-3 agonist peptides can be chemically synthesized by commercially available automated procedures, including, without limitation, exclusive solid phase synthesis, partial solid phase methods, fragment condensation, classical solution synthesis. In addition, recombinant and synthetic methods of peptide production can be combined to produce semi-synthetic peptides. The peptides of the invention are preferably prepared by solid phase peptide synthesis as described by Merrifield, 1963, *J. Am. Chem. Soc.* 85:2149; 1997. In one embodiment, synthesis is carried out with amino acids that are protected at the alphamino terminus. Trifunctional amino acids with labile side-chains are also protected with suitable groups to prevent undesired chemical reactions from occurring during the assembly of the peptides. The alpha-amino protecting group is selectively removed to allow subsequent reaction to take place at the amino-terminus. The conditions for the removal of the alpha-amino protecting group do not remove the side-chain protecting groups.

The alpha-amino protecting groups are those known to be useful in the art of stepwise peptide synthesis. Included are acyl type protecting groups, e.g., formyl, trifluoroacetyl, acetyl, aromatic urethane type protecting groups, e.g., benzyloxycarbonyl (Cbz), substituted benzyloxycarbonyl and 9-fluorenylmethyloxycarbonyl (Fmoc), aliphatic urethane protecting groups, e.g., t-butyloxycarbonyl (Boc), isopropyloxycarbonyl, cyclohexyloxycarbonyl, and alkyl type protecting groups, e.g., benzyl, triphenylmethyl. The preferred protecting group is Boc. The side-chain protecting groups for Tyr include tetra hydropyranyl, tert-butyl, trityl, benzyl, Cbz, 4-Br-Cbz and 2,6dichlorobenzyl. The preferred side-chain protecting group for Tyr is 2,6dichlorobenzyl. The side-chain protecting groups for Asp include benzyl, 2,6-dichlorobenzyl, methyl, ethyl, and cyclohexyl. The preferred side-chain protecting group for Asp is cyclohexyl. The side-chain protecting groups for Thr and Ser include acetyl, benzoyl, trityl, tetrahydropyranyl, benzyl, 2,6dichlorobenzyl, and Cbz. The preferred protecting group for Thr and Ser is benzyl. The side-chain protecting groups for Arg include nitro, Tos, Cbz, adamantyloxycarbonyl, and Boc. The preferred protecting group for Arg is Tos. The side-chain amino group of Lys can be protected with Cbz, 2-Cl-Cbz, Tos, or Boc. The 2-Cl-Cbz group is the preferred protecting group for Lys. The side-chain protecting groups selected must remain intact during coupling and not be removed during the deprotection of the amino-terminus protecting group or during coupling conditions. The side-chain protecting groups must also be removable upon the completion of synthesis, using reaction conditions that will not alter the finished peptide.

Solid phase synthesis is usually carried out from the carboxyterminus by coupling the alpha-amino protected (side-chain protected) amino acid to a suitable solid support. An ester linkage is formed when the attachment is made to a chloromethyl or hydroxymethyl resin, and the resulting peptide will have a free carboxyl group at the C-terminus. Alternatively, when a benzhydrylamine or p-methylbenzhydrylamine resin is used, an amide bond is formed and the resulting peptide will have a carboxamide group at the C-terminus. These resins are commercially available, and their preparation has described by Stewart et al., 1984, *Solid Phase Peptide Synthesis* (2nd Edition), Pierce Chemical Co., Rockford, Ill.

The C-terminal amino acid, protected at the side chain if necessary and at the alpha-amino group, is coupled to the benzhydrylamine resin using various activating agents including dicyclohexylcarbodiimide (DCC), N,N'-diisopropyl-carbodiimide and carbonyldiimidazole. Following the attachment to the resin support, the alpha-amino protecting group is removed using trifluoroacetic acid (TFA) or HCl in dioxane at a temperature between 0 and 25° C. Dimethylsulfide is added to the TFA after the introduction of methionine (Met) to suppress possible S-alkylation. After removal of the alpha-amino protecting group, the remaining protected amino acids are coupled stepwise in the required order to obtain the desired sequence.

Various activating agents can be used for the coupling reactions including DCC,N,N'-diisopropyl-carbodiimide, benzotriazol-1-yl-oxy-tris-(dimethylamino) phosphonium hexa-fluorophosphate (BOP) and DCC-hydroxybenzotriazole (HOBt). Each protected amino acid is used in excess (>2.0 equivalents), and the couplings are usually carried out in Nmethylpyrrolidone (NMP) or in DMF, $CH_2Cl_2$ or mixtures thereof. The extent of completion of the coupling reaction is monitored at each stage, e.g., by the ninhydrin reaction as described by Kaiser et al., 1970, *Anal. Biochem.* 34:595. In cases where incomplete coupling is found, the coupling reaction is repeated. The coupling reactions can be performed automatically with commercially available instruments.

After the entire assembly of the desired peptide, the peptide-resin is cleaved with a reagent such as liquid HF for 1–2 hours at 0° C., which cleaves the peptide from the resin and removes all side-chain protecting groups. A scavenger such as anisole is usually used with the liquid HF to prevent cations formed during the cleavage from alkylating the amino acid residues present in the peptide. The peptide-resin can be deprotected with 5 TFA/dithioethane prior to cleavage if desired.

Side-chain to side-chain cyclization on the solid support requires the use of an orthogonal protection scheme which enables selective cleavage of the side-chain functions of acidic amino acids (e.g., Asp) and the basic amino acids (e.g., Lys). The 9-fluorenylmethyl (Fm) protecting group for the side-chain of Asp and the 9-fluorenylmethyloxycarbonyl (Fmoc) protecting group for the side-chain of Lys can be used for this purpose. In these cases, the side-chain protecting groups of the Boc-protected peptide-resin are selectively removed with piperidine in DMF. Cyclization is achieved on the solid support using various activating agents including DCC, DCC/HOBt, or BOP. The HF reaction is carried out on the cyclized peptide-resin as described above.

Methods for polypeptide and peptide purification are well-known in the art, including, without limitation, preparative disc-gel electrophoresis, isoelectric focusing, HPLC, reversed-phase HPLC, gel filtration, ion exchange and partition chromatography, and countercurrent distribution. For some purposes, it is preferable to produce the polypeptide or peptide in a recombinant system in which the protein contains an additional sequence (e.g., epitope or protein) tag that facilitates purification (see above).

In one approach, the coding sequence of a polypeptide or peptide can be cloned into a vector that creates a fusion with a sequence tag of interest. Suitable vectors include, without limitation, pRSET (Invitrogen Corp., San Diego, Calif.), pGEX (Amersham-Pharmacia Biotech, Inc., Piscataway, N.J.), pEGFP (CLONTECH Laboratories, Inc., Palo Alto, Calif.), and pMALTM (New England BioLabs (NEB), Inc., Beverly, Mass.) plasmids. Following expression, the epitope, or protein tagged polypeptide or peptide can be purified from a crude lysate of the translation system or host cell by chromatography on an appropriate solid-phase matrix. In some cases, it may be preferable to remove the epitope or protein tag (i.e., via protease cleavage) following purification. As an alternative approach, antibodies produced against a protein or peptide can be used as purification reagents. Other purification methods are also possible.

Antibodies

Another aspect of the invention pertains to antibodies directed to a PSA-3 agonist peptide (e.g., SEQ ID NO:3–SEQ ID NO:5), a PSA polypeptide comprising this peptide, or fragments or variants thereof. The invention provides polyclonal and monoclonal antibodies. The antibodies may be elicited in an animal host (e.g., rabbit, goat, mouse, or other nonhuman mammal) by immunization with disorder-associated immunogenic components. Antibodies may also be elicited by in vitro immunization (sensitization) of immune cells. The immunogenic components used to elicit the production of antibodies may be isolated from cells or chemically synthesized. The antibodies may also be produced in recombinant systems programmed with appropriate antibody-encoding DNA. Alternatively, the antibodies may be constructed by biochemical reconstitution of purified heavy and light chains. The antibodies include hybrid antibodies, chimeric antibodies, and univalent antibodies. Also included are Fab fragments, including Fab' and Fab(ab)$^2$ fragments of antibodies.

An isolated PSA-3 agonist peptide, a PSA polypeptide comprising this peptide, or fragment or variant thereof, can be used as an immunogen to generate antibodies using standard techniques for polyclonal and monoclonal antibody preparation. Full-length PSA polypeptides can be used or, alternatively, the invention provides antigenic peptide portions of these polypeptides for use as immunogens. An antigenic peptide of the invention comprises a sufficient number of contiguous amino acid residues of the amino acid sequence, or a variant thereof, to encompass an epitope of a PSA polypeptide such that an antibody raised against the peptide forms a specific immune complex with the peptide or polypeptide. Typically, at least 5 contiguous amino acids are sufficient to define an epitope. In one embodiment, a PSA-3 agonist epitope may comprise at least 8 contiguous amino acids.

An appropriate immunogenic preparation can contain, for example, 1) recombinantly produced PSA-3 agonist peptides, or PSA polypeptides comprising these peptides; 2) chemically synthesized PSA-3 agonist peptides or PSA polypeptides comprising these peptides, or 3) fragments or variants of (1)–(2). The preparation can further include an adjuvant, such as Freund's complete or incomplete adjuvant, or similar immunostimulatory agent. A number of adjuvants are known and used by those skilled in the art. Non-limiting examples of adjuvants include incomplete Freund's adjuvant, and surface-active substances such as lysolecithin, pluronic polyols, polyanions, peptides, oil emulsions, keyhole limpet hemocyanin, and dinitrophenol. Further examples of adjuvants include stearyl tyrosine (A. Nixon-George et al., 1990, *J. Immunol.* 144:4798–4802; Paoletti, et al., 1997, J. Infect. *Diseases* 175:1237–9; U.S. Pat. No. 4,258,029 to Moloney et al.; U.S. Pat. No. 5,683,699 to Jennings, et al.), N-acetyl-muramyl-Lthreonyl-D-isoglutamine (thr-MDP), N-acetyl-nor-muramyl-L-alanyl-Disoglutamine (CGP 11637, referred to as nor-MDP), and N-acetylmuramylLalanyl-D-isoglutaminyl-L-alanine-2-(1'-2'-dipalmitoyl-sn-glycero-3 hydroxyphosphoryl-oxy)-ethylamine (CGP 19835A, referred to as MTP-PE). One particular adjuvant comprises 5% (wt/vol) squalene, 2.5% Pluronic L121 polymer and 0.2% polysorbate in phosphate buffered saline (Kwak et al., 1992, *New Eng. J. Med.* 327:1209–1215). More examples of adjuvants are listed herein below. The effectiveness of an adjuvant may be determined by measuring the amount of antibodies directed against the immunogenic peptide.

The immunogen can be conjugated to a carrier protein, if desired, to increase immunogenicity, particularly, if a small peptide is used. Commonly used carriers that are routinely used chemically coupled to peptides include serum albumins, e.g., bovine, sheep, goat, or fish serum albumin, thyroglobulin, and keyhole limpet hemocyanin. The coupled immunogencarrier is then used to immunize a recipient animal (e.g., mouse, rat, sheep, goat, or rabbit). The antibody titer in the immunized animal can be monitored over time by standard techniques, such as with an enzyme linked immunosorbent assay (ELISA) using immobilized PSA-3 agonist peptide, or a PSA polypeptide comprising this peptide. If desired, the antibody molecules can be isolated from the mammal (e.g., from the blood) and further purified by well-known techniques, such as protein A chromatography to obtain the IgG fraction.

At an appropriate time after immunization, e.g., when the antibody titers are highest, antibody-producing cells can be obtained from the animal subject and used to prepare monoclonal antibodies by standard techniques, such as the hybridoma technique (see Kohler and Milstein, 1975, *Nature* 256:495–497; Brown et al., 1981, *J. Immunol.* 127: 539–46; Brown et al., 1980, *J.Biol. Chem.* 255:4980–83; Yeh et al., 1976, PNAS 76:2927–31; and Yeh et al., 1982, *Int. J Cancer* 29:269–75), the human B cell hybridoma technique (Kozbor et al., 1983, *Immunol. Today* 4:72), the EBV-hybridoma technique (Cole et al., 1985, *Monoclonal Antibodies and Cancer Therapy*, Alan R. Liss, Inc., pp. 77–96) or trioma techniques. The technology for producing hybridomas is well-known (see generally R. H. Kenneth, 1980, *Monoclonal Antibodies: A New Dimension In Biological Analyses*, Plenum Publishing Corp., New York, N.Y.; E. A. Lerner, 1981, *Yale J. Biol. Med.,* 54:387–402; M. L. Gefter et al., 1977, *Somatic Cell Genet.* 3:231–36). In general, an immortal cell line (typically a myeloma) is fused to lymphocytes (typically splenocytes) from a mammal immunized with a PSA-3 agonist immunogen (e.g., peptide or polypeptide) as described above, and the culture supernatants of the resulting hybridoma cells are screened to identify a hybridoma producing a monoclonal antibody that binds a PSA-3 agonist peptide or PSA polypeptide comprising this peptide.

Any of the many well known protocols used for fusing lymphocytes and immortalized cell lines can be applied for the purpose of generating an monoclonal antibody to a PSA-3 agonist peptide or PSA polypeptide comprising this peptide (see, e.g., G. Gafter et al., 1977, Nature 266:55052; Gefter et al., 1977; Lerner, 1981; Kenneth, 1980). Moreover, the ordinarily skilled worker will appreciate that there are many variations of such methods. Typically, the immortal cell line (e.g., a myeloma cell line) is derived from the same mammalian species as the lymphocytes. For example, murine hybridomas can be made by fusing lymphocytes from a mouse immunized with an immunogenic preparation of this invention with an immortalized mouse cell line. Preferred immortal cell lines are mouse myeloma cell lines that are sensitive to culture medium containing hypoxanthine, aminopterin, and thymidine (HAT medium). Any of a number of myeloma cell lines can be used as a fusion partner according to standard techniques, e.g., the P3-NS1/1-Ago-1, P3-x63-Ag8.653, or Sp2/O-Ag14 myeloma lines. These myeloma lines are available from ATCC (American Type Culture Collection, Manassas, Va.). Typically, HAT-sensitive mouse myeloma cells are fused to mouse splenocytes using polyethylene glycol (PEG). Hybridoma cells resulting from the fusion arc then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind the PSA-3 agonist peptide, e.g., using a standard ELISA assay.

Alternative to preparing monoclonal antibody-secreting hybridomas, a monoclonal antibody can be identified and isolated by screening a recombinant combinatorial immunoglobulin library (e.g., an antibody phage display library) with the corresponding PSA-3 agonist peptide to thereby isolate immunoglobulin library members that bind these molecules. Kits for generating and screening phage display libraries are commercially available (e.g., the Pharmacia Recombinant Phage Antibody System, Catalog No. 279400-01; and the Stratagene SurfZAPTM Phage Display Kit, Catalog No. 240612). Examples of methods and reagents particularly amenable for use in generating and screening antibody display library can be found in, for example, A. Blume U.S. Pat. No. 6,010,861, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. Internatinal Publication No. WO 92/01047; Garrard et al. International Publication No. WO 92/09690; Ladner et al. International Publication No. WO 90/02809; Fuchs et al., 1991, *Bio/Technology* 9:1370–1372; Hay et al., 1992, Hum. *Antibod. Hybridomas* 3:81–85; Huse et al., 1989, *Science* 246:1275–1281; Griffiths et al., 1993, *EMBO J* 12:725–734; Hawkins et al., 1992, *J. Mol.* Biol. 226:889–896; Clarkson et al., 1991, *Nature* 352:624–628; Gram et al., 1992, PNAS 89:3576–3580; Garrad et al., 1991, *BiolTechnology* 9:1373–1377; Hoogenboom et al., 1991, Nuc. *Acid Res.* 19:4133–4137; Barbas et al., 1991, PNAS 88:7978–7982; and McCafferty et al., 1990, *Nature* 348:552–55.

Additionally, recombinant antibodies to a PSA-3 agonist peptide, or PSA polypeptide comprising this peptide, can be made using standard recombinant DNA techniques. For example, chimeric and humanized monoclonal antibodies that comprise both human and non-human portions can be produced. Exemplary methods for producing chimeric and humanized monoclonal antibodies are described in, for example, Robinson et al. International Application No. PCT/US86/02269; Akira, et al. European Patent Application 184,187; Taniguchi, M., European Patent Application 171, 496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al., 1988, *Science* 240:1041–1043; Liu et al., 1987, PNAS 84:3439–3443; Liu et al., 1987, *J. Immunol.* 139:3521–3526; Sun et al., 1987, PNAS 84:214–218; Nishimura et al., 1987, *Canc. Res.* 47:999–1005; Wood et al., 1985, *Nature* 314:446–449; and Shaw et al., 1988, *J. Nat/. Cancer Inst.* 80:1553–1559; S. L. Morrison, 1985, *Science* 229:1202–1207; Oi et al., 1986, *BioTechniques* 4:214; Winter U.S. Pat. No. 5,225,539; Jones et al., 1986, *Nature* 321:552–525; Verhoeyan et al., 1988, *Science* 239:1534; and Bcidler et al., 1988, *J. Immunol.* 141:4053–4060.

An antibody against a PSA-3 agonist peptide or a PSA polypeptide comprising this peptide (e.g., monoclonal antibody) can be used to isolate the corresponding molecule by standard techniques, such as affinity chromatography or immunoprecipitation. For example, antibodies can facilitate the purification of recombinantly produced PSA polypeptides or PSA-3 agonist peptides from host cells. In addition, an antibody that binds to a PSA-3 agonist peptide can be used to detect the corresponding peptide or a PSA polypeptide comprising this peptide (e.g., in a cellular lysate or cell supernatant) in order to evaluate patterns or levels of protein expression. Such antibodies can also be used as diagnostics to monitor PSA polypeptide or PSA-3 agonist peptide levels in tissue as part of a clinical testing procedure, e.g., to, for example, determine the efficacy of a given treatment regimens as described in detail herein.

Drug Screening and Design

This invention provides methods of screening for drugs using PSA-3 agonist peptides (e.g., SEQ ID NO:3–SEQ ID NO:5), polypeptides comprising these peptides (e.g., SEQ ID NO:25–SEQ ID NO:30), or fragments or variants thereof, in competitive binding assays, according to methods well-known in the art. For example, competitive drug screening assays can be employed using complexes comprising PSA-3 agonist peptides and HLA-A2 molecules, and screening for test agents that disrupt, enhance, or otherwise alter the peptide-HLA complex. Agents that disrupt the peptide-HLA complex may serve as analogs that minic the function of the PSA-3 agonist peptide (i.e., mimetics). Agents that enhance the formation or stability of the peptide-HLA complex may serve to increase immunoreactivity of the PSA-3 agonist peptide.

Test agents may encompass numerous chemical classes, though typically they are organic molecules, e.g., small molecules. Preferably, test agents have a molecular weight of less than 5000 daltons, more preferably, test agents have a molecular weight of more than 50 and less than 2,500 daltons. Such test agents can comprise functional groups necessary for structural interaction with proteins, particularly hydrogen bonding, and typically include at least an amine, carbonyl, hydroxyl or carboxyl group, preferably at least two of the functional chemical groups. Useful test agents often comprise cyclical carbon or heterocyclic structures and/or aromatic or polyaromatic structures substituted with one or more of the above functional groups. Such test agents can also comprise biomolecules including peptides, saccharides, fatty acids, steroids, purines, pyrimidines, derivatives, structural analogs, or combinations thereof.

Test agents may include, for example, 1) peptides such as soluble peptides, including Ig-tailed fusion peptides and members of random peptide libraries (see, e.g., Lam et al., 1991, *Nature* 354:82–84; Houghten et al., 1991, *Nature* 354:84–86) and combinatorial chemistry-derived molecular 5 libraries made of D- and/or L-configuration amino acids; 2) phosphopeptides (e.g., members of random and partially degenerate, directed phosphopeptide libraries, see, e.g., Songyang et al, 1993, *Cell* 72:767–778); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules.

Test agents can be obtained from a wide variety of sources including libraries of synthetic or natural compounds. Synthetic compound libraries are commercially available from, for example, Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich Chemical Company, Inc. (Milwaukee, Wis.). Natural compound libraries comprising bacterial, fungal, plant or animal extracts are available from, for example, Pan Laboratories (Bothell, Wash.). In addition, numerous means are available for random and directed synthesis of a wide variety of organic compounds and biomolecules, including expression of randomized oligonucleotides.

Alternatively, libraries of natural compounds in the form of bacterial, fungal, plant and animal extracts can be readily produced. Methods for the synthesis of molecular libraries are readily available (see, e.g., DeWitt et al., 1993, *Proc. Natl. Acad. Sci. USA* 90:6909; Erb et al., 1994, *Proc. Natl. Acad. Sci. USA* 91:11422; Zuckermann et al., 1994, *J. Med. Chem.* 37:2678; Cho et al., 1993, *Science* 261:1303; Carell et al., 1994, *Angew. Chem. Int. Ed. Engl.* 33:2059; Carell et al., 1994, *Angew. Chem. Int. Ed. Engl.* 33:2061; and in Gallop et al., 1994, *J. Med. Chem.* 37:1233). In addition, natural or synthetic compound libraries and compounds can be readily modified through conventional chemical, physical and biochemical means (see, e.g., Blondelle et al., 1996, *Trends in Biotech.* 14:60), and may be used to produce combinatorial libraries. In another approach, previously identified pharmacological agents can be subjected to directed or random chemical modifications, such as acylation, alkylation, esterification, amidification, and the analogs can be screened for further enhancement of immunoreactivity to PSA-3 agonist peptides.

Numerous methods for producing combinatorial libraries are known in the art, including those involving biological libraries; spatially addressable parallel solid phase or solution phase libraries; synthetic library methods requiring deconvolution; the 'one-bead one-compound' library method; and synthetic library methods using affinity chromatography selection. The biological library approach is limited to polypeptide libraries, while the other four approaches are applicable to polypeptide, non-peptide oligomer, or small molecule libraries of compounds (K. S. Lam, 1997, *Anticancer Drug Des.* 12:145).

Non-limiting examples of small molecules, small molecule libraries, combinatorial libraries, and screening methods are described in B. Seligmann, 1995, "Synthesis, Screening, Identification of Positive Compounds and Optimization of Leads from Combinatorial Libraries: Validation of Success" p. 69–70. *Symposium: Exploiting Molecular Diversity: Small Molecule Libraries for Drug Discovery*, La Jolla, Calif., Jan. 23–25, 1995 (conference summary available from Wendy Warr & Associates, 6 Berwick Court, Cheshire, UK CW4 7 HZ); E. Martin et al., 1995, *J. Med. Chem.* 38:1431–1436; E. Martin et al., 1995, "Measuring diversity: Experimental design of combinatorial libraries for drug discovery" *Abstract, ACS Meeting*, Anaheim, Calif., COMP 32; and E. Martin, 1995, "Measuring Chemical Diversity: Random Screening or Rationale Library Design" p. 27–30, *Symposium: Exploiting Molecular Diversity: Small Molecule Libraries for Drug Discovery*, La Jolla, Calif. Jan. 23–25, 1995 (conference summary available from Wendy Warr & Associates, 6 Berwick Court, Cheshire, UK CW4 7 HZ).

Libraries may be screened in solution (e.g., Houghten, 1992, *Biotechniques* 13:412–421), or on beads (Lam, 1991, *Nature* 354:82–84), chips (Fodor, 1993, *Nature* 364:555–556), bacteria or spores (Ladner U.S. Pat. No. 5,223,409), plasmids (Cull et al., 1992, *Proc. Natl. Acad. Sci. USA* 89:1865–1869), or on phage (Scoff and Smith, 1990, *Science* 249:386–390; Devlin, 1990, *Science* 249:404–406; Cwirla et al., 1990, *Proc. Natl. Acad. Sci. USA* 97:6378–6382; Felici, 1991, *J. Mol. Biol.* 222:301–310; Ladner, supra).

Where the screening assay is a binding assay, a PSA-3 agonist peptide, PSA polypeptide comprising this peptide, or variant or fragment thereof, may be joined to a label, where the label can directly or indirectly provide a detectable signal. Various labels include radioisotopes, fluorescers, chemiluminescers, enzymes, specific binding molecules, particles, e.g., magnetic particles, and the like. Specific binding molecules include pairs, such as biotin and streptavidin, digoxin and antidigoxin, etc. For the specific binding members, the complementary member would normally be labeled with a molecule that provides for detection, in accordance with known procedures.

A variety of other reagents may be included in the screening assay. These include reagents like salts, neutral proteins, e.g., albumin, detergents, etc., that are used to facilitate optimal protein-protein binding and/or reduce nonspecific or background interactions. Reagents that improve the efficiency of the assay, such as protease inhibitors, nuclease inhibitors, anti-microbial agents, etc., may be used. The components are added in any order that produces the requisite binding. Incubations are performed at any temperature that facilitates optimal activity, typically between 4 and 40° C. Incubation periods are selected for optimum activity, but may also be optimized to facilitate rapid high-throughput screening. Normally, between 0.1 and 1 hr will be sufficient. In general, a plurality of assay mixtures is run in parallel with different agent concentrations to obtain a differential response to these concentrations. Typically, one of these concentrations serves as a negative control, i.e., at zero concentration or below the level of detection.

To perform cell-free ligand screening assays, it may be desirable to immobilize either a PSA-3 agonist peptide, PSA polypeptide comprising this peptide, or fragment or variant thereof, to a surface to facilitate identification of test agents that bind to these molecules, as well as to accommodate automation of the assay. For example, a fusion protein comprising a PSA-3 agonist peptide and an affinity tag can be produced. In one embodiment, a fusion protein comprising a PSA-3 agonist peptide and FLAGS tag is adsorbed onto anti-FLAG® tag conjugated beads or microtiter plates. Labeled (e.g., radiolabeled) test agents are added to the coated beads under conditions to allow complex formation (e.g., at physiological conditions for salt and pH). Following incubation, the coated beads are washed to remove any unbound test agents, and the amount of immobilized radiolabel is determined. Alternatively, the complex is dissociated and the radiolabel present in the supernatant is determined. In another approach, the beads are analyzed by SIDS-PAGE to identify the bound agents.

The invention further provides methods of rational drug design employing PSA-3 agonist peptides, polypeptides comprising these peptides, antibodies that bind to these peptides, or portions or functional equivalents thereof. The goal of rational drug design is to produce structural analogs, e.g., mimetics, of biologically active polypeptides of interest or of small molecules with which they interact. In turn, these analogs can be used to fashion drugs which are, for example, more active or stable forms of the PSA-3 agonist peptide, or which, e.g., increase immunoreactivity to the peptide in vivo (see, e.g., Hodgson, 1991, *Bio/Technology* 9:19–21). An example of rational drug design is the development of HIV protease inhibitors (Erickson et al., 1990, *Science,* 249: 527–533).

In one approach, the three-dimensional structure of a PSA-3 agonist peptide, or polypeptide comprising this peptide, is determined by x-ray crystallography, computer modeling, or a combination thereof. Useful information regarding the structure of a peptide or polypeptide can also be gained by computer modeling based on the structure of homologous proteins. In addition, PSA-3 agonist peptides, polypeptides comprising these peptides, or fragments thereof, can be analyzed by alanine scans (Wells, 1991, *Methods in Enzymol.,* 202:390–4.11). In this technique, each amino acid residue in a polypeptide or peptide is replaced by alanine, and its effect on the activity of the polypeptide is determined.

In another approach, an antibody specific to a PSA-3 agonist peptide can be isolated, selected by a functional assay, and then analyzed to solve its crystal structure. In principle, this approach can yield a pharmacore upon which subsequent drug design can be based. Alternatively, it is possible to bypass protein crystallography altogether by generating anti-idiotypic antibodies (anti-ids) to a functional, pharmacologically active antibody. As a mirror image of a mirror image, the binding site of the anti-ids is predicted to be an analog of the corresponding PSA-3 agonist peptide. The anti-id can then be used to identify and isolate peptides from banks of chemically or biologically produced banks of peptides. Selected peptides can subsequently be used as pharmacores.

Non-limiting examples of methods and computer tools for drug design are described in R. Cramer et al., 1974, *J. Med. Chem.* 17:533; H. Kubinyi (ed) 1993, *3D QSAR in Drug Design, Theory, Methods, and Applications,* ESCOM, Leiden, Holland; P. Dean (ed) 1995, *Molecular Similarity in Drug Design,* K. Kim "Comparative molecular field analysis (ComFA)" p. 291–324, Chapman & Hill, London, UK; Y. et al., 1993, *J. Comp.-Aid. Mol. Des.* 7:83102; G. Lauri and P. A. Bartlett, 1994, *J. Comp.-Aid. Mol. Des.* 8:51–66; P. J. Gane and P. M. Dean, 2000, *Curr. Opin. Struct. Biol.* 10(4):401–4; H. O. Kim and M. Kahn, 2000, *Comb. Chem. High Throughput Screen.* 3(3):167–83; G. K. Farber, 1999, *Pharmacol Ther.* 84(3):327–32; and H. van de Waterbeemd (Ed.) 1996, *Structure-Property Correlations in Ding Research,* Academic Press, San Diego, Calif.

In another aspect of this invention, cells and animals that carry PSA3 agonist peptides, PSA polypeptides comprising these peptides, or fragments or variants thereof, can be used as model systems to study and test for agents that have potential as therapeutic compounds. After a test agent is administered to animals or applied to the cells, the phenotype of the animals/cells can be determined. For example, cytotoxic T cells can be used to screen for compounds that enhance the ability of the PSA-3 agonist peptide to create a cytotoxic T cell response. In this type of screen, cytotoxic T cells are incubated with a selected epitope, for example, in a microtiter plate. The agent to be tested, e.g. a drug, is then added to the well and the growth of the T cells is measured. T cell expansion indicates that the test agent enhances the T cell response. Test agents that enhanced T cell response are then subjected to further evaluation.

In accordance with these methods, one may design drugs that result in, for example, enhanced immunoreactivity to PSA. By virtue of the availability of nucleotide sequences encoding PSA-3 agonist peptides, sufficient amounts of these peptides, or polypeptides comprising these peptides, may be produced to perform such analytical studies as x-ray crystallography. In addition, the knowledge of the PSA-3 agonist peptide sequences will guide those employing computer-modeling techniques in place of, or in addition to x-ray crystallography.

Antibody-Based Diagnostics

In one embodiment of this invention, antibodies which specifically bind to a PSA-3 agonist peptide (e.g., SEQ ID NO:3–SEQ ID NO:5), a PSA polypeptide comprising this peptide (e.g., SEQ ID NO:25-–EQ ID NO:30), or variants or fragments thereof, may be used in assays to monitor subjects being treated with the vector-, cell-, or peptide-based therapeutics described herein. The antibodies useful for diagnostic purposes may be prepared in the same manner as those disclosed above. Antibodies may be raised to a full-length PSA-3 agonist peptide, or a PSA polypeptide comprising this peptide. Alternatively, the antibodies may be raised to portions or variants of this peptide or polypeptide.

Diagnostic assays for PSA-3 agonist peptides, or PSA polypeptides comprising these peptides, include methods that utilize the antibody and a label to detect the peptides or polypeptides in biological samples (e.g., human body fluids, cells, tissues, or extracts of cells or tissues). The antibodies may be used with or without modification, and may be labeled by joining them, either covalently or non-covalently, with a reporter molecule. A wide variety of reporter molecules that are known in the art may be used, several of which are described herein.

Many immunoassay formats are known in the art, and the particular format used is determined by the desired application. An immunoassay can use, for example, a monoclonal antibody directed against a single disease-associated epitope, a combination of monoclonal antibodies directed against different epitopes of a single disease-associated antigenic component, monoclonal antibodies directed towards epitopes of different disease-associated antigens, polyclonal antibodies directed towards the same disease-associated antigen, or polyclonal antibodies directed towards different disease-associated antigens. Protocols can also, for example, use solid supports, or may involve immunoprecipitation. Typically, immunoassays use either a labeled antibody or a labeled antigenic component (i.e., to compete with the antigen in the sample for binding to the antibody). Exemplary labels are described in the sections shown above.

In accordance with this invention, "competitive" (U.S. Pat. Nos. 3,654,090 and 3,850,752), "sandwich" (U.S. Pat. No. 4,016,043), and "double antibody," or "DASP" assays may be used. Several procedures for measuring the amount of a PSA-3 agonist peptide, or PSA polypeptide comprising this peptide, in a sample (e.g., ELISA, RIA, and FACS) are known in the art and provide a basis for diagnostics. Negative control values for a polypeptide or polypeptide complex are established by incubating biological samples taken from pre-treatment subjects, preferably human, with antibody to a polypeptide or peptide under conditions suitable for association. The amount of antibody-antigen association may be quantified by various methods; photometric means are preferred. Levels of the polypeptide or peptide in the post-treatment sample and in the pretreatment (negative control) sample are compared. The difference between pre-treatment and post-treatment values establishes the parameters for monitoring levels during treatment protocols.

Kits suitable for antibody-based diagnostic applications typically include one or more of the following components:

(1) Antibodies: The antibodies may be pre-labeled. Alternatively, the antibody may be unlabeled and the ingredients for labeling may be included in the kit in separate containers, or a secondary, labeled antibody is provided. Antibodies may be monoclonal or polyclonal, and may be directed to PSA-3 agonist peptides, or PSA polypeptides comprising these peptides, or variants or fragments thereof;

(2) Reaction components: The kit may also contain other suitably packaged reagents and materials needed for the particular immunoassay protocol, including solid-phase matrices, if applicable, and standards.

The kits referred to above may include instructions for conducting the test. Furthermore, in preferred embodiments, the diagnostic kits are adaptable to high-throughput and/or automated operation.

Nucleic Acid-Based Diagnostics

In another embodiment of this invention, PSA-3 agonist nucleic acids (e.g., SEQ ID NO:20–SEQ ID NO:22), or variants or fragments thereof, may be used in assays to monitor subjects being treated with the vector- or cellbased therapeutics described herein. The invention therefore provides methods for detecting levels or sequences of PSA-3 agonist nucleic acids in a sample, such as in a biological sample (e.g., human body fluids, cells, tissues, or extracts of cells or tissues). For example, the presence of PSA-3 agonist polynucleotide sequences can be detected by DNA-DNA or DNARNA hybridization, or by amplification, using probes or primers comprising at least a portion of a disclosed polynucleotide, or a sequence complementary thereto.

In specific aspects, PSA-3 agonist oligonucleotides or oligomers, i.e. primers, can be employed in nucleic acid amplification-based assays (e.g., PCR assays) to detect cells or other biological samples containing PSA-3 agonist DNA or RNA. Alternatively, PSA-3 oligomers, i.e., probes, can be used in nucleic acid hybridization-based assays (e.g., Southern, dot, or slot blots) to detect cells or other biological samples containing PSA-3 agonist DNA or RNA. Preferably, nucleic acids useful as probes or primers in diagnostic methods include oligonucleotides at least 15 contiguous nucleotides in length, more preferably at least 18, 21, 24, or 30, contiguous nucleotides in length, that hybridize specifically with PSA-3 agonist nucleic acids.

Several methods can be used to produce specific probes for PSA-3 agonist polynucleotides. For example, labeled probes can be produced by oligo-labeling, nick translation, end-labeling, or PCR amplification using a labeled nucleotide. Alternatively, PSA-3 agonist polynucleotide sequences, or any portions or fragments thereof, may be cloned into a vector for the production of an mRNA probe. Such vectors are known in the art, are commercially available, and may be used to synthesize RNA probes in vitro by addition of an appropriate RNA polymerase, such as T7, T3, or SP(6) and labeled nucleotides. These procedures may be conducted using a variety of commercially available kits (e.g., from Amersham-Pharmacia; Promega Corp.; and U.S. Biochemical Corp., Cleveland, Ohio). Suitable reporter molecules or labels which may be used include radionucleotides (e.g., 32P, 3H, and 35S), enzymes, fluorescent (e.g., rhodamine, fluorescein, and CyTM3, CyTM5), chemiluminescent, or chromogenic agents, and other labels (e.g., DNP, digoxigenin, and biotin) such as substrates, cofactors, inhibitors, magnetic particles, and the like.

A sample to be analyzed, such as, for example, a tissue sample (e.g., hair or buccal cavity) or body fluid sample (e.g., blood, saliva, or urine), may be contacted directly with the nucleic acid probes. Alternatively, the sample may be treated to extract the nucleic acids contained therein. It will be understood that the particular method used to extract DNA will depend on the nature of the biological sample. The resulting nucleic acid from the sample may be subjected to gel electrophoresis or other size separation techniques, or, the nucleic acid sample may be immobilized on an appropriate solid matrix without size separation.

In accordance with this invention, diagnostic assays may be used to monitor PSA-3 agonist polynucleotide levels during therapeutic treatment or intervention. For example, PSA-3 agonist polynucleotide sequences, or fragments, or complementary sequences thereof, can be used in Southern or Northern analysis, dot blot, or other membrane-based technologies; in PCR technologies; or in dip stick, pin, ELISA or biochip assays utilizing fluids or tissues from patient biopsies to detect the status of, e.g., levels of PSA-3 agonist expression. Such qualitative or quantitative methods are well known in the art (G. H. Keller and M. M. Manak, 1993, *DNA Probes*, 2$^{nd}$ Ed, Macmillan Publishers Ltd., England; D. W. Dieffenbach and G. S. Dveksler, 1995, *PCR Primer. A Laboratory Manual*, Cold Spring Harbor Press, Plainview, N.Y.; B. D. Hames and S. J. Higgins, 1985, *Gene Probes* 1, 2, IRL Press at Oxford University Press, Oxford, England).

Methods suitable for quantifying the expression of PSA-3 agonist nucleic acids include radiolabeling or biotinylating nucleotides, coamplification of a control nucleic acid, and standard curves onto which the experimental results are interpolated (P. C. Melby et al., 1993, J. *Immunol. Methods* 159:235–244; and C. Duplaa et al., 1993, *Anal. Biochem.* 212(1):229–36.). The speed of quantifying multiple samples may be accelerated by running the assay in an ELISA format where the oligomer of interest is presented in various dilutions and a spectrophotometric or colorimetric response gives rapid quantification. In accordance with established methods, microarray formats (i.e., DNA chips or biochips) may also be used (see, e.g., D. A. Rew D A, 2001, *Eur. J. Surg. Oncol.* 27(5):5048; P. J. Planet et al., 2001, *Genome Res.* 11(7):1149–55; J. Quackenbush, 2001, *Nat. Rev. Genet.* 2(6):418–27; O. P. Kallioniemi et al., 2001, *Hum. Mol. Genet.* 10(7):657–62; U.S. Pat. No. 6,015,702 to P. Lal et al.; M. Schena (Ed.), 2000, *Microarray Biochip Technology*, Eaton Publishing).

Kits suitable for nucleic acid-based diagnostic applications typically include the following components:

(1) Probe DNA: The probe DNA may be prelabeled. Alternatively, the probe DNA may be unlabeled and the ingredients for labeling may be included in the kit in separate containers. Probes may hybridize to PSA-3 agonist nucleic acids, or longer PSA nucleic acids comprising PSA-3 agonist nucleic acids; and (2) Hybridization reagents: The kit may also contain other suitably packaged reagents and materials needed for the particular hybridization protocol, including solid-phase matrices, if applicable, and standards.

Vector- and Cell-Based Therapies

In one embodiment of the present invention, one or more PSA-3 agonist peptides (e.g., SEQ ID NO:3–SEQ ID NO:5), or PSA polypeptides comprising these peptide (e.g., SEQ ID NO:25–SEQ ID NO:30), or fragment or variant thereof, are administered to a host via a vector (e.g., plasmid or viral vector). The preferred host is human. A specific immune response for PSA can be generated by administering between about 105–109 pfu of the recombinant pox virus, constructed as discussed above to a host, more preferably 10' pfu can be administered. At least one interval thereafter, which is preferably one to three months later, the immune response is boosted by administering additional antigen to the host. More preferably there is at least a second "boost" preferably one to three months after the first boost.

Optionally, one or more cytokines, e.g., IL-2, IL-6, IL-12, RANTES, GM-CSF, TNF-α, or IFN-γ, growth factors, e.g., GM-CSF or G-CSF; or costimulatory molecules, e.g., ICAM-1, LFA-3, CD72, B7-1, B7-2, or other B7 related molecules; or OX-40L or 41 BBL; or combinations thereof; may be used as biological adjuvants (see, e.g., M. L. Salgaller et al., 1998, *J. Surg. Oncol.* 68(2):122–38; M. T. Lotze et al., 2000, *Cancer J. Sci. Am.* 6(Suppl 1):S61–6; L. Cao et al., 1998, *Stem Cells* 16(Suppl 1):251–60; M. Kuiper et al., 2000, *Adv. Exp. Med. Biol.* 465:381–90) and can be administered systemically to the host, or co-administered via insertion of the genes encoding the molecules into a vector, for example, a recombinant pox vector (see, e.g., U.S. Pat. No. 6,045,802 to Schlom et al.). In various embodiments, these genes' may be cloned into same vector as the PSA-3 agonist coding sequence, or the genes may cloned into one or more separate vectors for co-administration. In addition, nonspecific immunomodulating factors such as Bacillus Cahnette-Guerin (BCG) and levamisole can be co-administered.

In some cases, it may be preferable to administer an adjuvant to further increase the immune response in the subject. A number of adjuvants are known and used by those skilled in the art. Examples of adjuvants suitable for human use include, but are not limited to, alum, aluminum salts, aluminum phosphate, aluminum hydroxide, aluminum silica, Montanide (e.g., ISA 50, ISA 51, ISA 80, ISA 206, ISA 720, ISA 740), and calcium phoshate (e.g., nanoparticles; BioSante Pharmaceuticals, Inc., Lincolnshire, Ill.). A preferred adjuvant is RIBI adjuvant (e.g., Detox®, Corixa Corp., Seattle Wash.). Detox® includes three components extracted from bacteria, monophosphoryl lipid A, trehalose dimycolate and cell wall skeleton (TDM+CWS+MPL®; Corixa Corp.) in a 2% squalene/Tween 80 emulsion. Other preferred adjuvants include BCG, ISCOM® and ISCOMA-TRIX® (CSL Limited, Parkville, Australia) and aluminum hydroxide adjuvant (Superphos, Biosector).

The recombinant vector can be administered using any acceptable route, including, for example, scarification and injection, e.g., intradermal, subcutaneous, intramuscular, intravenous or intraperitoneal administration. For parenteral administration, the recombinant vectors will typically be injected in a sterile aqueous or non-aqueous solution, suspension or emulsion in association with a pharmaceutically-acceptable carrier such as physiological saline.

In another embodiment of the present invention, the PSA-3 agonist peptide is administered to a host via a host cell (e.g., CTLs). Alternatively, the PSA-3 agonist peptide or compositions of the invention can be co-administered with an antigen presenting cell, such as a dendritic cell or a B-cell. Cytotoxic T cells specific for an PSA-3 agonist peptide can be established from peripheral blood mononuclear cells (PBMC) obtained from a host immunized as discussed above. The cytotoxic T cell can be cultured to amplify its number and then injected back into the host by a variety of means. Generally, between $1 \times 10^5$ and $2 \times 10^{11}$ cytotoxic T cells per 5 infusion are administered in, for example, one to three infusions of 200 to 250 ml each over a period of 30 to 60 minutes. After the completion of the infusions, the patient may be treated with recombinant interleukin-2 with a dose of 720,000 IU per kilogram of body weight intravenously every eight hours; some doses can be omitted depending on the patient's tolerance for the drug. In addition, after infusion, additional antigen or fragments containing T cell eliciting epitope(s) may be administered to the patient to further expand the T cell number. The antigen or epitope may be formulated with an adjuvant and/or may be in a liposomal formulation. The cytotoxic T cells can also be modified by introduction of a viral vector containing DNA encoding one or more PSA-3 agonist peptides, polypeptide comprising these peptides, and/or TNF-α. These modified cells can be reintroduced into a host in an effort to enhance the anti-tumor activity of the cells. Other cytokines or modulators can also be used, as described in detail herein.

Peptide-Based Therapies

This invention contemplates compositions comprising one or more PSA-3 agonist peptides (e.g., SEQ ID NO:3–SEQ ID NO:5), or PSA polypeptides comprising these peptides (e.g., SEQ ID NO:25–SEQ ID NO:30), or fragments or variants thereof, and a physiologically acceptable carrier, excipient, or diluent. This invention further contemplates pharmaceutical compositions useful in practicing the therapeutic methods of this invention. Preferably, a pharmaceutical composition includes, in admixture, a pharmaceutically acceptable excipient (carrier) and one or more PSA-3 agonist peptides, PSA polypeptides comprising these peptides, or fragments or variants, as described herein, as active ingredients.

The preparation of pharmaceutical compositions that contain polypeptides or peptides as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients that are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH-buffering agents, which enhance the effectiveness of the active ingredient.

PSA-3 agonist peptides, or PSA polypeptides comprising these peptides, can be formulated into the pharmaceutical composition as neutralized physiologically acceptable salt forms. Suitable salts include the acid addition salts (i.e., formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Pharmaceutical compositions may be produced as neutral or salt forms. Salts can be formed with many acids, including, but not limited to, hydrochloric, sulfuric, acetic, lactic, tartaric, malic and succinic acids. Compositions can take the form of solutions, suspensions, suppositories, tablets, pills, capsules, sustained release compounds, or powders. Such formulations can contain 10%–95% (w/w) of the active ingredient, preferably 25%–70% (w/w). Pharmaceutical preparations and compositions can also contain one or more physiologically acceptable carrier(s), excipient(s), diluent(s), disintegrant(s), lubricant(s), plasticizer(s), filler(s), colorant(s), dosage vehicle(s), absorption enhancer(s), stabilizer(s), or bacteriocide(s). The production and formulation of such compositions and preparations are carried out by methods known and practiced in the art.

Following the preparation of pharmaceutical compositions, they may be placed in appropriate containers and labeled for the treatment of indicated conditions. Such labeling can include amount, frequency, and method of administration. Preparations may be administered systemically by oral or parenteral routes. Non-limiting parenteral routes of administration include subcutaneous, intramuscular, intraperitoneal, intravenous, transdermal, inhalation, intranasal, intra-arterial, intrathecal, enteral, sublingual, or rectal. Intravenous administration, for example, can be performed by injection of a unit dose. The term "unit dose" when used in reference to a pharmaceutical composition of this invention refers to physically discrete units suitable as unitary dosage for humans, each unit containing a predetermined quantity of active material calculated to produce the desired therapeutic effect in association with the required diluent; i.e., carrier, or vehicle.

Pharmaceutical compositions are administered in a manner compatible with the dosage formulation, and in a therapeutically effective amount. The quantity to be administered depends on the subject to be treated, capacity of the subject's immune system to utilize the active ingredient, and degree of immunostimulation desired. Precise amounts of active ingredient required to be administered depend on the judgment of the practitioner and are specific for each individual. However, suitable dosages may range from about 0.1 mg to 20 mg, preferably about 0.5 mg to about 10 mg, and more preferably one milligrams to several milligrams of active ingredient per kilogram body weight of individual per day, depending on the route of administration. Suitable regimes for initial administration and booster shots are also variable, but are typified by an initial administration followed by repeated doses at one or more hour intervals by a subsequent injection or other administration. Alternatively, continuous intravenous infusions sufficient to maintain concentrations of 10 nM to 10 µM in the blood are contemplated.

An exemplary pharmaceutical formulation comprises: PSA-3 agonist peptide (5.0 mg/ml); sodium bisulfite USP (3.2 mg/ml); disodium edetate USP (0.1 mg/ml); and water for injection q.s.a.d. (1.0 ml). Further guidance in preparing pharmaceutical formulations can be found in, e.g., Gilman et al. (eds), 1990, *Goodman and Gilman's: The Pharmacological Basis of Therapeutics,* 8th ed., Pergamon Press; and *Remington's Pharmaceutical Sciences,* 17th ed., 1990, Mack Publishing Co., Easton, Pa.; Avis et al. (eds), 1993, *Pharmaceutical Dosage Forms: Parenteral Medications,* Dekker, N.Y.; Lieberman et al. (eds), 1990, *Pharmaceutical Dosage Forms: Disperse Systems,* Dekker, N.Y.

In some cases, it may be preferable to administer an adjuvant to further increase the immune response in the subject. A number of adjuvants are known and used by those skilled in the art. Examples of adjuvants suitable for human use include, but are not limited to, alum, aluminum salts, aluminum phosphate, aluminum hydroxide, aluminum silica, Montanide ISA 720, and calcium phoshate (e.g., nanoparticles; BioSante Pharmaceuticals, Inc., Lincolnshire, Ill.). A preferred adjuvant is RIBI adjuvant (e.g., Detox®, Corixa Corp., Seattle Wash.) which contains three components extracted from bacteria, monophosphoryl lipid A, trehalose dimycolate and cell wall skeleton (TDM+CWS+MPL®; Corixa Corp.) in a 2% squalene/Tween 80 emulsion. Other preferred adjuvants include BCG, ISCOM® and ISCOMATRIX® (CSL Limited, Parkville, Australia), and aluminum hydroxide adjuvant (Superphos, Biosector).

In various embodiments, one or more cytokines, e.g., IL-2, IL-6, IL-12, RANTES, GM-CSF, TNF-α, or IFN-γ, growth factors, e.g., GM-CSF or G-CSF; or co-stimulatory molecules, e.g., ICAM-1, LFA-3, CD72, B7-1, 1372, or other B7-related molecules; or OX-40L or 41 BBL; or a combination thereof; may be used as biological adjuvants (see, e.g., M. L. Salgaller et al., 1998, *J. Surg. Oncol.* 68(2):122–38; M. T. Lotze et al., 2000, *Cancer J. Sci. Am.* 6(Suppl 1):S61–6; L. Cao et al., 1998, *Stem Cells* 16(Suppl 1):251–60; M. Kuiper et al., 2000, *Adv. Exp. Med. Biol.* 465:381–90) and can be administered systemically to the host, or co-administered via insertion of the genes encoding the molecules into a vector, for example, a recombinant pox vector (see U.S. Pat. No. 6,045,802 to Schlom et al.).

A therapeutically effective amount of a pharmaceutical composition containing one or more PSA-3 peptides, or polypeptides comprising these peptides, is an amount sufficient to reduce, ameliorate, or eliminate prostate cancer. An effective amount can be introduced in one administration or over repeated administrations to an individual being treated. Therapeutic administration can be followed by prophylactic administration, after treatment of the disease. A prophylactically effective amount is an amount effective to prevent disease and will depend upon the specific illness and subject. The therapeutically effective dose may be estimated initially, for example, either in cell culture assays or in animal models, usually mice, rats, rabbits, dogs, sheep, goats, pigs, or non-human primates. The animal model may also be used to determine the maximum tolerated dose and appropriate route of administration. Such information can then be used to determine useful doses and routes for administration in humans.

Notably, the peptide-based, vector-based, and cell-based therapies of the invention can be used individually or in any combination. In addition, these treatments can be used as adjuncts to other treatments for prostate cancer, including, but not limited to, hormone therapy, chemotherapy, surgery (e.g., radical prostatectomy), cryosurgery, radiation therapy (e.g., external beam or seed implant), interstitial brachytherapy, and immunotherapy (e.g., anti-HER2 antibodies; Herceptin®).

EXAMPLES

The examples as described herein are intended to further illustrate the present invention and are not intended to limit the invention in any way.

Example 1

Cell Cultures. The human prostate carcinoma cell line LNCAP (M. G. Sanda et al., 1995, J. Natl. Cancer Inst. 87:280–285) (HLA-A2 positive and PSA positive) and SK-MEL-24 (T. E. Carey et al., 1976, Proc. Natl. Acad. Sci. USA 73:3278–3282), a human melanoma cell line (HLA-A2 positive and PSA negative), were purchased from American Type Culture Collection (Manassas, Va.). The cultures were free of mycoplasma and were maintained in complete medium (RPMI 1640; Life Technologies, Inc., Grand Island, N.Y.) supplemented with 10% fetal bovine serum, 2 mM glutamine, 100 units/ml penicillin, and 100 µg/ml streptomycin (Life Technologies, Inc.).

The C1R cell line is a human plasma leukemia cell line that does not express endogenous HLA-A or B antigens (K. S. Anderson et al., 1993, J. Immunol. 151:3407–3419). C1R-A2 cells are C1R cells that express a transfected genomic clone of HLA-A2.1 (W. J. Storkus et al., 1987, J. Immunol., 138:16571659). These cells were obtained from Dr. William E. Biddison (National Institute of Neurological Disorders and Stroke, NIH, Bethesda, Md.). The 174CEM-T2 cell line (T2) transport deletion mutant (K. T. Hogan et al., 1988, J. Exp. Med. 168:725–736) was provided by Dr. Peter Cresswell (Yale University School of Medicine, New Haven, Conn.). C 1 R-A2 cells and T2 cells were mycoplasma free and were maintained in RPMI 1640 complete medium and in Iscove's modified Dubecco's complete medium (Life Technologies), respectively.

The V8T cell line, a cytotoxic T lymphocyte (CTL) line directed against the carcinoembryonic antigen (CEA) CAP-1 epitope, was established from a patient with metastatic colon carcinoma who was enrolled in a Phase I trial using rV-CEA as immunogen (K. Y. Tsang et al., 1997, Clin. Cancer Res. 3:2439–2449). V8T cells were cultured in RPMI 1640 complete medium containing 10% human AB serum and IL-2 (provided by the National Cancer Institute, Surgery Branch, 20 units/ml).

V8T cells were restimulated with CAP-1 peptide (25 µg/nl) on day 16 after prior restimulation at an effector to APC ratio of 1:3. Irradiated (23,000 rads) autologous EBV transformed B cells were used as APCs.

Example 2

Peptides. A panel of analogs with single or double amino acid substitutions at positions P1, P2 and P10 of PSA peptide PSA-3 (P. Correale et al., 1997, J. Nat. Cancer Inst. 19:293–300) (FIG. 1), and a CEA peptide CAP1–6D (S. Zaremba et al., 1997, Cancer Res. 57:45704577), were greater than 96% pure. Peptides were made by Multiple Peptide Systems (San Diego, Calif.).

Single-color flow cytometric analysis. The method for single-color flow cytometric analysis was described previously (F. Guadagni et al., 1990, Cancer Res. 50:6248–6255). Briefly, cells were washed three times with cold $Ca^{2+}$ and $Mg^{2+}$-free DPBS and then stained for 1 h with mAb against HLA-A2 (A2,69, One Lambda, Inc., Canoga Park, Calif.), using 10 µg of the 1× working dilution per $10^6$ cells. Mineral oil plasmacytoma-104E (Cappel/Organon Teknika Corp., West Chester, Pa.) was used as an isotype control. The cells were washed three times and incubated with a 1:100 dilution of fluorescein isothiocyanate (FITC)-labeled goat anti-mouse immunoglobulin (IgG) (Kirkegaard and Perry Laboratories, Gaithersburg, Md.). The cells were immediately analyzed using a Becton Dickinson FACScan equipped with a blue laser with an excitation of 15 nW at 488 nm. Data were gathered from 10,000 live cells, stored and used to generate results.

Example 3

Dual-color flow cytometric analysis. The procedure for dual-color flow cytometric analysis was similar to that for single-color analysis with the following exceptions. The antibodies used were anti-CD4 FITC/anti-CD8 PE, anti-CD45R0-FITC/anti-CD49d PE, anti-CD28 FITC/anti-CD56 PE, anti-CD86 FITC/anti-CD80 PE, anti-CD58 FITC/anti-CD54 PE, anti-MHC class I FITC/anti-MHC class II PE, and anti-IgG1 FITC/anti-IgG2a PE (isotype controls). Antibodies to CD4, CD8, CD28, CD45R0, CD56, CD49d, CD 54, CD80, CD86, and CD58 were purchased from Becton Dickinson. Antibodies to MBC-class I and MHC-class II were purchased from Serotec, UK. Antibodies to CD14 and CD54 were purchased from Becton Dickinson. Staining was done simultaneously for 1 h, after which cells were washed three times, resuspended as above, and immediately analyzed using a Becton Dickinson FACScan equipped with a blue laser with an excitation of 15 nW at 488 nm with the use of the CELLQuest program (Becton Dickinson, San Jose, Calif.).

Example 4

Peptide Binding to HLA-A2. Binding of PSA-3 analogs to HLA-A2 molecules was evaluated by binding to T2A2 cells as demonstrated by flow cytometry (H. W. Nijman et al., 1993, Eur. J. Immunol. 23:1215–1219). Briefly, $1 \times 10^6$ cells in serum-free Iscove's modified Dulbecco's complete medium were incubated with peptides at a concentration of 50 µg/ml in 24 well culture plates at 37° C. in 5% $CO_2$. Flow cytometry for peptide binding was performed using T2 cells and single-color analysis. After cells were washed three times in DPBS, as described above, they were incubated for 1 h with HLA-A2 specific MAb (One Lambda, Inc.) using 10 µg of a 1× working dilution per $10^6$ cells. UPC-10 (Cappel/Organon Teknika) was used as isotype control. The cells were washed three times and incubated with 1:100 dilution of FITC-labeled anti-mouse IgG (Becton Dickinson). Analysis was conducted with the FACScan, as described above. Cells were maintained on ice during all cell preparation and staining.

Example 5

Culture of DCs from PBMCs. HLA-A2 normal donor PBMCs (peripheral blood mononuclear cells) were obtained from heparinized blood. PBMCs were separated using lymphocyte separation medium gradient (Organon Teknika, Durham, N.C.), as described previously (A. Boyum et al., 1968, *Scand. J. Clin. Lab. Invest. Suppl.* 97:51–76). Dendritic cells (DCs) were prepared using a modification of the procedure described by Sallusto et al. (F. Sallusto et al., 1994, *J. Exp. Med.* 179:1109–1118). PBMCs ($1.5 \times 10^8$) were resuspended in AIM-V medium containing 2 mM glutamine, 50 Ng/ml streptomycin, and 10 µg/ml gentamycin (Life Technologies, Inc.), and allowed to adhere to a T-150 flask (Corning Costar Corp., Cambridge, Mass.). After 2 h at 37° C., the non-adherent cells were removed with a gentle rinse. The adherent cells were cultured for 6–7 days in AIM-V medium containing 100 ng/ml of recombinant human GM-CSF (rhGM-CSF) and 20 ng/ml of recombinant human IL-4 (rhIL-4) and 20 ng/ml of TNF-α. The culture medium was replenished every 3 days.

Example 6

Recombinant Virus and Infection of DCs with Vaccinia Virus Containing PSA (rV-PSA) or PSA-3A (rV-PSA-3A). PSA cDNA was inserted under the control of the vaccinia 40K promoter (L. Gritz et al., 1990, J. Virol. 64:5948–5957) into the HindIII M genomic region of the Wyeth strain of vaccinia virus. The *E. coli* lacZ gene, under the control of the fowlpox C1 promoter (S. Jenkins et al., 1991, AIDS *Res. Hum. Retroviruses* 7:991–998), was included as a calorimetric marker for recombinant viruses. Recombinant virus was identified using a chromogenic assay for the lacZ gene product, as described previously (D. Panicali et al., 1986, *Gene* 47:193–199). For the construction of rV-PSA-3A, codon 155 in the PSA sequence was changed from ATT (isoleucine) to CTG (leucine) by in vitro mutagenesis (G. Mazzara et al., 1993, *Methods Enzymol.* 217: 557–581, K. Smith et al., 1993, *Vaccine* 11:43–53).

The resulting PSA sequence, designated PSA-3A, was inserted under the control of the vaccinia 40K promoter into the HindIII M genomic region of a derivative of the Wyeth strain of vaccinia virus using a hostrange selection system, as described previously (G. Mazzara et al., 1993, *Meth. Enzymol.* 217:557–581; K. Smith et al., 1993, *Vaccine* 11:43–53, 1993). DCs ($1 \times 10^6$) were incubated in 1 ml of Opti-MEM medium (Life Technologies, Inc.) at 37° C. with rV-PSA, rV-PSA-3A or control vaccinia virus vector. Titration experiments indicated that $1 \times 10^7$ plaque-forming units/ml, equal to a multiplicity of infection (MOI) of 10 for 1 h, were able to consistently induce production of PSA. The infected DCs were suspended in 10 ml of fresh, warm RPMI-1640 complete medium containing 100 ng/ml of rhGM-CSF, 20 ng/ml rhIL-4, and 20 ng/ml of TNF-α cultured for 24 h, and then subsequently used as APCs.

Example 7

Generation of T cell Lines. Modification of the protocol described by Tsang et al. (K. Y. Tsang et al., 1997, *Clin. Cancer Res.* 3:2439–2449) was used to generate PSA-specific CTL. DCs were used as APCs and nonadherent cells isolated from PBMCs were used as a source of effector cells. PSA-3 or PSA-3A peptide was added to the DCs at a final concentration of 25 µg/ml. Autologous non-adherent cells were then added to APCs at an APC to effector ratio of 1:10. Cultures were incubated for 3 days at 37° C. in a humidified atmosphere containing 5% $CO_2$. After removal of the peptide containing medium, the cultures were then supplemented with recombinant human IL-2 at a concentration of 20 units/ml for 7 days. The IL-2 containing medium was replenished every 3 days. The 3-day incubation with peptide and 7-day IL-2 supplement constituted one in vitro stimulation (IVS) cycle. Primary cultures were restimulated with PSA peptide (25 µg/ml) on day 11 to begin the next IVS cycle. Irradiated autologous DCs were used as APC for three IVS cycles. Irradiated (23,000 rads) autologous EBV-transformed B cells were used as APC after the third IVS cycle.

Example 8

Cytotoxic Assay. Target cells (C1 R-A2 or tumor cells) were labeled with 50 µCi of $^{111}$Indium-labeled oxyquinoline (Medi-Physics Inc., Arlington, Ill.) for 15 min at room temperature. Target cells ($0.3 \times 10^4$) in 100 µl of RPMI-1640 complete medium were added to each of 96 wells in flat-bottomed assay plates (Corning Costar Corp.). Labeled C1 R-A2 target cells were incubated with peptides at the concentration indicated for 60 min at 37° C. in 5% $CO_2$ before adding effector cells. No peptide was used when carcinoma cell lines were used as targets. Effector cells were suspended in 100 µl of RPMI-1640 complete medium supplemented with 10% pooled human AB serum and added to the target cells. The cells were then incubated at 37° C. in 5% $CO_2$ for 4 or 16 h. Supernatant was harvested for gamma counting with the use of harvester frames (Skatron, Inc., Sterling, Va.). Determinations were carried out in triplicate, and standard deviations were calculated. Specific lysis was calculated with the use of the following formula (all values in cpm):

$$\% \text{ lysis} = \frac{\text{Observed release} - \text{Spontaneous release}}{\text{Total release} - \text{Spontaneous release}} \times 100$$

Spontaneous release was determined from wells where 100 µl of RPMI-1640 complete medium was added. Total releasable radioactivity was obtained after treatment of targets with 2.5% Triton x-100.

Example 9

Apoptosis Assay. T cells were incubated for 48 h in the presence of peptide-pulsed autologous B cells as described in the IVS procedure, above, and replated to 96-well plates for 24 h. Apoptosis was analyzed using the terminal deoxynucleotidyl transferase-mediated nick-end labeling (TUNEL) assay (Y. Gavrieli et al., 1992, J. *Cell Biol.* 119:493–501).

Example 10

Transgenic Mice. HLA-A2.1/$K^b$ transgenic mice were kindly provided by Dr. L. Sherman (Scripps Laboratories, San Diego, Calif.). Transgenic mice express the product of the HLA-A2.1/Kb chimeric gene in which the alpha-3 domain of the heavy chain is replaced by mouse H-2/$K^b$ domain, but the HLA-A2.1 alpha-1 and alpha-2 domains are unaltered (A. Vitiello et al., 1991, *J. Exp. Med.* 173:1007–1015; V. H. Engelhard et al., 1991, J. Immunol. 46:1226–1232).

Example 11

In Vivo Immunization and Murine T cell Cultures. Three groups of HLA-A2.1/K$^b$ transgenic mice (three mice per group) were immunized s.c. (subcutaneously) in the base of the tail with PSA-3 peptide-pulsed HLA-A2.1/K$^b$ DC, PSA-3A peptide-pulsed DCs from HLA-A2.1/K$^b$ transgenic mice, or DCs only. Peptides were used at a concentration of 50 µg/ml and DCs were used at 1×10$^6$ cell/mouse/injection. A total of three injections were given to each animal, 2 weeks apart. Mice injected with DCs only were used as controls. Mice were sacrificed 7 days after the last injection, and spleen cells were restimulated in vitro with 25 µg/ml of PSA-3 or PSA3A peptide with irradiated syngeneic spleen cell for 6 days. The cytokine production of these bulk cultures was tested. Peptide-pulsed Jurkat A2 (JA2 K$^b$) cells were used as stimulator cells. Jurkat 0201 K$^b$ cells are stable transfectants of the human T cell leukemia line, Jurkat, which express the product of HLA-A0201K$^b$ climeric gene (L. A. Sherman et al., 1992, Science 258:815–818).

Example 12

Detection of Cytokines. Supernatant of T cells exposed for 24 h to peptide-pulsed infected DC, rV-PSA infected DC, or rV-PSA-3A infected DC, in IL-2-free medium at various responder: stimulator ratios, were screened for secretion of IFN-γ using an ELISA kit (R & D Systems, Minneapolis, Minn.). The results were calculated as pg/ml. A Cytometric Bead Array (CBA) system (BD PharMingen, San Diego, Calif.) was also used to determine the secretion of multiple cytokines by specific T cell lines. The CBA system uses the fluorescence detection by flow cytometry to measure soluble analytes in a particle-based immunoassay. The BD human Th1/Th2 cytokine CBA Kit was employed to measure IL-2, IL-4, IL-5, IL-10, TNF-α, and IFN-γ protein levels in a single sample. The cytokine capture beads were mixed with PE-conjugated detection antibodies and then incubated with recombinant cytokine standards or test samples to form sandwich complexes. The samples results were generated in graphical and tabular format using BD CBA analysis software. The results were calculated as pg/ml.

Statistical Analysis. Statistical analysis of differences between means was done using a two-tailed paired t test (Stat View statistical software, Abacus Concepts, Berkeley, Calif.).

Results

Analysis of the primary and secondary HLA-A2 anchor residues at amino acid positions 1, 2, and 10 of the 10-mer PSA-3 peptide revealed that some modifications could enhance binding to HLA-A2. Accordingly, four different analogs of PSA-3 were synthesized (Table 1).

TABLE 1

| AMINO ACID SEQUENCE | DESIGNATION |
|---|---|
| VISNDVCAQV (SEQ ID NO:1) | PSA-3 |
| VISNDVCAQL (SEQ ID NO:2) | PSA-3 (L-163) |
| VLSNDVCAQV (SEQ ID NO:3) | PSA-3 (L-155) also called PSA-3A |
| YISNDVCAQV (SEQ ID NO:4) | PSA-3 (Y-154) |
| YLSNDVCAQV (SEQ ID NO:5) | PSA-3 (Y-154/L-155) |

Table 1: PSA analogs. Parental nonamer PSA-3 peptide (amino acid position 154–163 of PSA) and analog nonamers. Amino acids are shown by the single-letter code. Substitution amino acids are indicated in bold font.

The corresponding nucleotide sequences are shown in the table, below. Substitution codons are indicated in bold font.

| DESIGNATION | NUCLEOTIDE SEQUENCE |
|---|---|
| PSA-3 | GTT ATT TCC AAT GAC GTG TGT GCG CAA GTT (SEQ ID NO:18) |
| PSA-3 (L-163) | GTT ATT TCC AAT GAC GTG TGT GCG CAA CTG (SEQ ID NO:19) |
| PSA-3 (L-155; PSA-3A) | GTT CTG TCC AAT GAC GTG TGT GCG CAA GTT (SEQ ID NO:20) |
| PSA-3 (Y-154) | TAC ATT TCC AAT GAC GTG TGT GCG CAA GTT (SEQ ID NO:21) |
| PSA-3 (Y-154/L-155) | TAC CTG TCC AAT GAC GTG TGT GCG CAA GTT (SEQ ID NO:22) |

The four analogs were then tested for binding to the HLA-A2 positive T2A2 cells as described in the Examples section. The NCA peptide was previously shown to not bind to HLA-A2, and was used as a negative 5 control. Peptides were added to T2A2 cells at concentrations of 0 to 50 µg/ml. FIG. 1A shows that three of the four analogs bound to HLA-A2. Two analogs (L-155 and Y154) bound to HLA-A2 at higher levels than PSA-3 at the various peptide concentrations. Peptide analog 1–163 exhibited no binding to HLA-A2 (FIG. 1A).

Figure 1B:
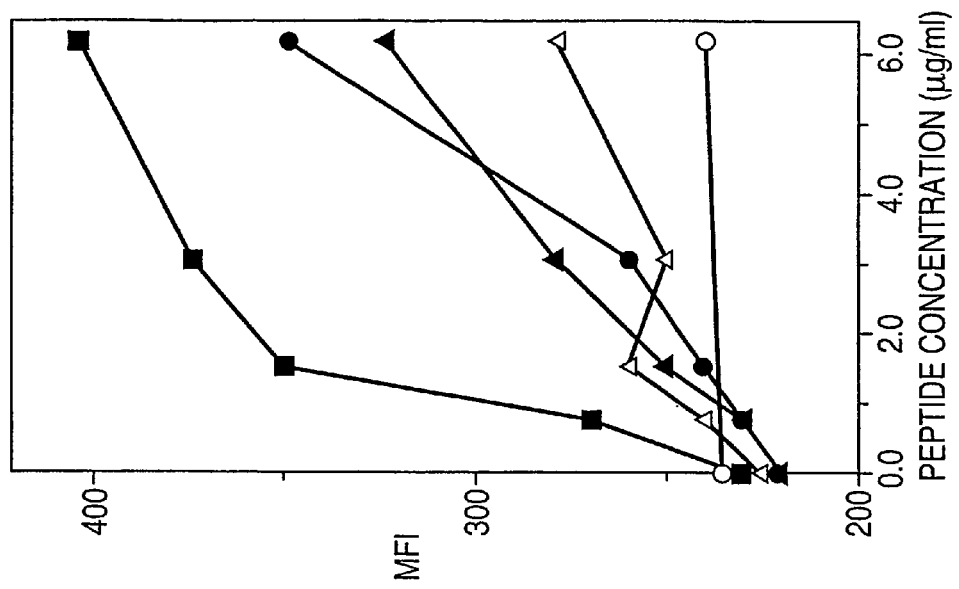
FIGS. 1A–1B. Binding of PSA peptides to HLA-A2. Peptides were analyzed for binding to the T2A2 cell line as described in the Examples section. Peptides were used at concentrations of 0 to 50 μg/ml (FIG. 1A) and lower concentrations (FIG. 1B). PSA-3 is the parental PSA peptide (open triangles). PSA-3 (L-155; also called PSA-3A) (solid squares), PSA-3 (Y154) (solid circles), PSA-3 (Y154/L155) (solid triangles) and PSA-3 (L163) (open squares) are PSA-3 agonist peptides. NCA peptide (open circles) is a negative control. Results are expressed in relative fluorescence values (MFI).
Figure 1A:
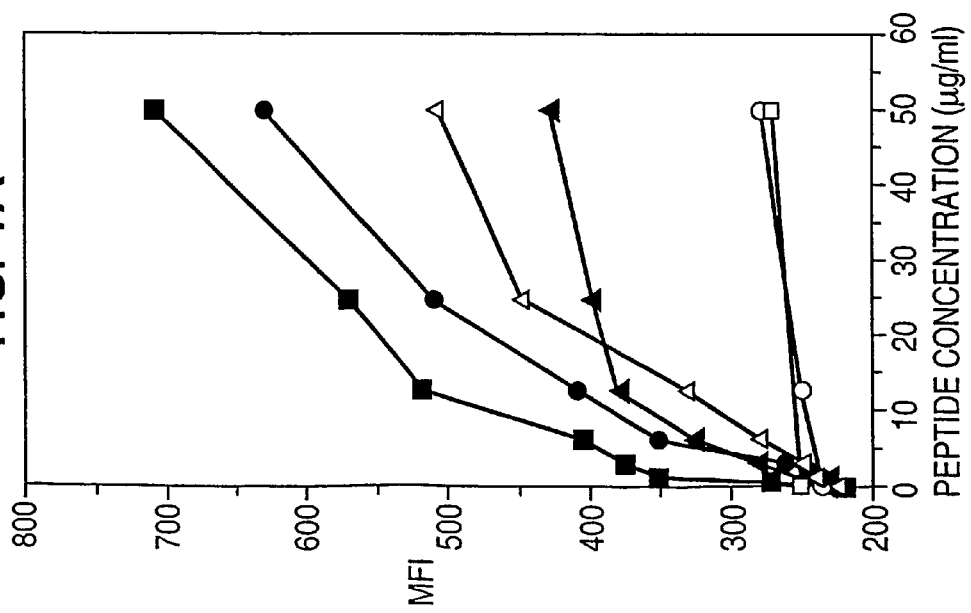

An analysis of peptide binding to HLA-A2 at lower peptide concentrations revealed that analog 1–155 clearly bound higher levels of HLA-A2 than PSA-3 (FIG. 1 B). The data indicated that the 1–155 peptide with a modification in primary anchor position 2 (position 155 of the PSA molecule) was a potential agonist of peptide PSA-3, and was given the designation PSA-3A. The PSA-3A peptide was thus chosen for further comparative studies with the native PSA-3 peptide. It should be noted that a peptide containing the identical change at position 155 (as found in PSA3A) as well as an additional change at the secondary anchor residue (position 154) actually bound at lower levels to HLA-A2 than the native PSA-3 peptide (FIGS. 1A–1B).

Studies were then undertaken to examine the stability of the peptideMHC complex for peptides PSA-3 and PSA-3A. Peptides were incubated with T2A2 cells overnight, washed free of unbound peptide and incubated with brefeldin-A to block delivery of new class I molecules to the cell surface. At various time points, cells were analyzed for the presence of peptide-HLA-A2 complexes. FIG. 2 shows that PSA-3A-HLA-A2 complexes were more stable than PSA-3 complexes over the 8-h observation period. Thus, both the ability of the peptide to bind MHC (FIGS. 1A–1B) and the stability (FIG. 2), i.e., avidity of the peptide-MHC complex, are greater for the PSA-3A peptide than the native PSA-3 peptide.

Studies were then conducted to establish and compare human T cell lines using APCs pulsed with the PSA-3 peptides and PSA-3A peptides. DCs from an apparently healthy donor were pulsed with either peptide as APCs, and autologous PBMCs were used as a source of effector cells. T cell cultures were established by pulsing with each peptide in the presence of IL-2 as described in the Examples section. At IVS cycle 3 (IVS-3), T cells were analyzed for the ability to lyse peptide-pulsed targets. The line established with peptide PSA-3A, designated T-PSA-3A, was shown to lyse C1R-A2 cells pulsed with peptide PSA-3A to a greater extent than cells pulsed with the PSA-3 peptide (FIG. 3A). T cells established using the PSA-3 peptide, however, also lysed target cells pulsed with the PSA-3A peptide to a greater extent than those pulsed with the PSA-3A peptide (FIG. 3B). This was seen at two different effector to target cell ratios.

To further analyze this phenomenon, C1R-A2 cells were then pulsed with different concentrations of the native and agonist peptides and used as targets for the two T cell lines. T cells generated with the PSA-3A peptide showed a greater percent lysis of target cells pulsed with the PSA-3A peptide than cells pulsed with the PSA-3 peptide at each peptide concentration; approximately 8-fold less PSA-3A peptide than PSA-3 peptide was necessary for lysis (FIG. 4A). Moreover, this phenomenon was also observed using T cells established with the native PSA-3 peptide. Thus, these T cells lysed C1R-A2 target cells pulsed with the PSA-3A peptide to greater levels at each peptide concentration than target cells pulsed with the PSA-3 peptide; approximately 8-fold less PSA-3A peptide was required to achieve similar levels of lysis. These studies provided the first indication that a T cell line derived from the PSA-3A peptide could recognize the native PSA-3 peptide MHC complex and lyse such cells presenting this complex.

Figure 5A:
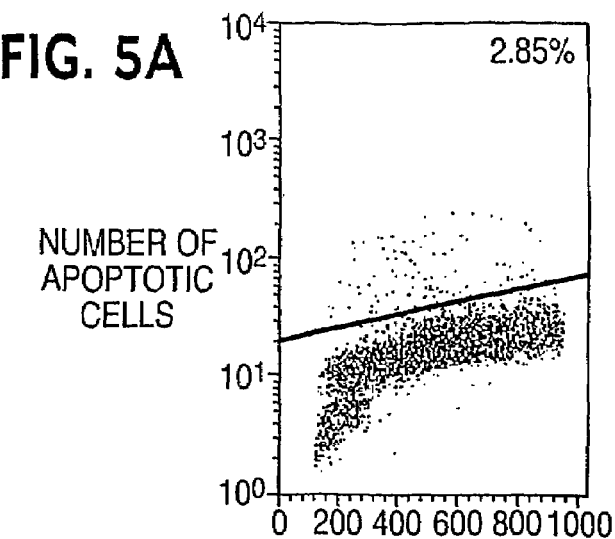
FIGS. 5A–5C. DNA fragmentation in peptide stimulated T cells using the TUNEL assay. Apoptosis of CD8$^+$ cells activated by PSA peptide pulsed autologous B cells.
Figure 5B:
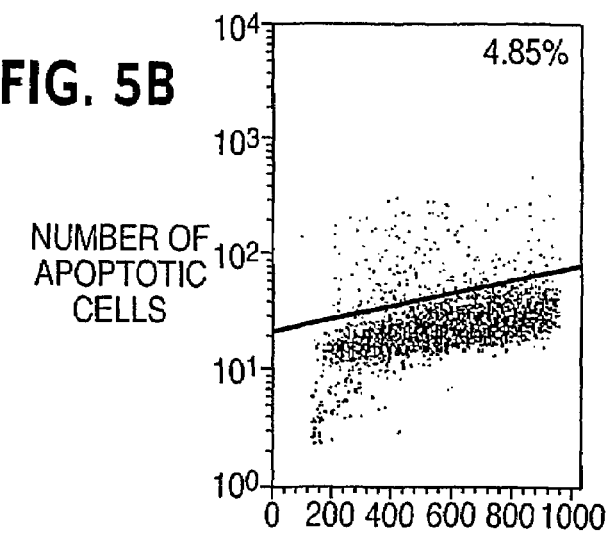
Figure 5C:
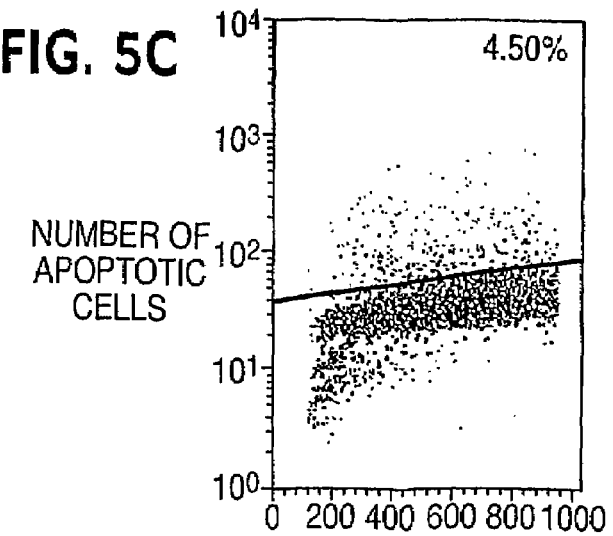

The T cell lines established with peptide PSA-3 (designated T-PSA-3) and peptide PSA-3A (designated T-PSA-3A) were both shown to be >95% positive for CD49d, >67% positive for $CD8^+$, <3.0% positive for $CD56^+$, and >88% positive for $CD45R0^+$ cells. T cells stimulated with autologous B cells pulsed with either peptide were analyzed at IVS-5 for DNA fragmentation by the TUNEL assay. FIG. 5 shows that 2.9% apoptotic $CD8^+$ cells were observed in the absence of peptide (FIG. 5A), 4.9% apoptotic $CD8^+$ cells were observed in cells stimulated with PSA-3 peptide (FIG. 5B), and 4.5% apoptotic $CD8^+$ cells were observed when cells were stimulated with PSA-3 peptide (FIG. 5C). Thus, no difference in apoptosis was seen in $CD8^+$ T cells stimulated with the agonist peptide as compared to the native peptide.

The cytokine profile of T cells stimulated with APCs pulsed with either the PSA-3 or the PSA-3A peptide was then analyzed. The T cell line derived using the PSA-3 peptide was used in these studies, and the APCs used were autologous B cells. A Cytometric Bead Array (CBA) assay was used for analysis (see Examples section) using supernatant fluids obtained 24 h after stimulation. FIGS. 6A–6C illustrate four of the 10 internal standards used for the calibration of the results obtained in this assay. FIGS. 6D–6F show the levels of each of six cytokines produced by T cells stimulated with APCs pulsed with no peptide, PSA-3A peptide, and PSA-3 peptide, respectively. These results demonstrate greater production of the type I cytokines IL-2 and IFN-γ by T cells stimulated with the PSA-3A peptide than the PSA-3 peptide. Low or undetectable levels of type 2 cytokines IL-4 and IL-10 were seen using either peptide. No TNF-α could be detected in supernatants at the 24-h time point. The results obtained for IL-5 will be discussed below (Conclusions section).

Studies were also conducted to determine the level of IFN-γ production by T cells, originally generated with the PSA-3A peptide, when stimulated with DCs that were pulsed with the PSA-3 and PSA-3A peptides. Table 2, below, shows that T cells stimulated with DCs pulsed with the PSA-3A peptide produce more IFN-γ than those stimulated with DCs pulsed with the PSA-3 peptide. Cultures devoid of peptide, DCs, or T cells demonstrated the specificity of the IFN-γ production (Table 2), and the lack of non-specific anti-allogeneic reactivity.

TABLE 2

| APC | PEPTIDE | T CELL | PRODUCTION OF IFN-γ (pg/ml) |
|---|---|---|---|
| DCs | PSA-3 | + | 280 |
| DCs | PSA-3 | None | <15 |
| None | PSA-3 | + | <15 |
| DCs | PSA-3A | + | 566 |
| DCs | PSA-3A | None | <15 |
| None | PSA-3A | + | <15 |
| DCs | None | + | <15 |

Table 2: Production of IFN-γ by a T cell line stimulated with PSA-3 or agonist PSA-3A peptides. The PSA-specific T cell line T-PSA-3A was used as effector cells at IVS-3. T-PSA-3A cells were stimulated with irradiated HLA-A2 positive allogeneic DCs either pulsed with PSA-3 or PSA-3A peptide at a concentration of 25 µg/ml and an effector-to-APC ratio of 10:1. After 24-h culture supernatants were collected and screened for the secretion of IFN-γ. APC=antigen producing cell.

It has been previously shown that the activation of T cells by peptidepulsed DCs is related to the level of IL-12 production by the DCs. Studies were therefore conducted to determine the levels of IL-12 production by DCs pulsed with PSA-3 and PSA-3A peptides in the presence of T cells. Table 3, below, shows that DCs in the absence of peptide, T cells alone, and peptide-pulsed T cells in the absence of DCs, all failed to produce detectable levels of IL-12. When DCs pulsed with PSA-3 peptide were incubated with either T-PSA-3 or T-PSA-3A T cell lines, DCs were shown to produce IL-12, with more IL-12 being produced by peptide-pulsed DCs cultured with the T-PSA-3A line (Table 3). When DCs pulsed with the PSA3A peptide were incubated with both T cell lines, the DCs incubated with the T-PSA-3A line again produced higher levels of IL-12 than those peptide-pulsed DCs incubated with the T cell line T-PSA-3 (Table 3).

TABLE 3

| APC | PEPTIDE | T CELL LINE | IL-12 PRODUCTION |
|---|---|---|---|
| DC | PSA-3A | T-PSA-3A | 27.5 |
| DC | PSA-3A | T-PSA-3 | 6.0 |
| DC | PSA-3 | T-PSA-3A | 10.5 |
| DC | PSA-3 | T-PSA-3 | 5.0 |
| None | PSA-3A | T-PSA-3A | <0.6 |
| None | PSA-3A | T-PSA-3 | <0.6 |
| None | PSA-3 | T-PSA-3A | <0.6 |
| None | PSA-3 | T-PSA-3 | <0.6 |
| None | None | T-PSA-3A | <0.6 |
| None | None | T-PSA-3 | <0.6 |
| DC | None | T-PSA-3A | <0.6 |
| DC | None | T-PSA-3 | <0.6 |

Table 3: The ability of DCs pulsed with peptides PSA-3 or PSA-3A agonist to produce IL-12. The PSA-specific T cell lines T-PSA-3A (derived by pulsing PBMC with the PSA-3A peptide) and T-PSA-3 (derived by pulsing PBMC with the PSA-3 peptide) were used as effector cells at IVS-4. T cells 15 were stimulated with HLA-A2 positive allogeneic DCs either pulsed with PSA-3 or PSA-3A peptide at a concentration of 25 µg/ml and an effector-to-APC ratio of 10:1. After 24-h culture supernatants were collected and screened for the secretion of IL-12. IL-12 production is expressed as pg/ml/5 × $10^5$ DC.

Studies were then conducted to determine whether T cells generated with the PSA-3A peptide could lyse tumor cells that endogenously express native PSA. Table 4, below, shows that the T-PSA-3A line was capable of lysing the LNCaP human prostate carcinoma cell line that expresses native PSA and was HLA-A2 positive. The HLA-A2 positive SK-mel human melanoma line that does not express PSA showed no lysis. The T-PSA-3 line (generated with the native PSA-3A peptide) also lysed the LNCaP line, but at lower levels than that observed with the T-PSA-3A line at each effector to target cell ratio (Table 4). To determine whether the lysis was MHC restricted, antibody-blocking experiments were carried out. Table 4 shows that the lysis of the LNCaP tine by the T-PSA-3A line was blocked by the anti-HLA-A2 antibody and not by the isotype matched control antibody UPC-10.

TABLE 4

EXPERIMENT 1

| T CELL LINE | TARGET | PSA | HLA-A2 | E:T RATIO | % LYSIS |
|---|---|---|---|---|---|
| T-PSA-3A | LNCaP | + | + | 25:1 | 25.1(2.6*) |
|  |  |  |  | 12.5:1 | 15.2(1.7*) |
| T-PSA-3A | SK-mel | − | + | 25:1 | 3.1(0.6) |
| T-PSA-3 | LNCaP | + | + | 25:1 | 15.2(1.4*) |
|  |  |  |  | 12.5:1 | 8.6(0.8*) |
| T-PSA-3 | SK-mel | − | + | 25:1 | 1.35(3.3) |

EXPERIMENT 2

| T CELL LINE | TARGET | PSA | HLA-A2 | ANTIBODY | % LYSIS |
|---|---|---|---|---|---|
| T-PSA-3A | LNCaP | + | + | None | 16.8(1.4) |
| T-PSA-3A | LNCaP | + | + | Anti-HLA-A2 | 4.7(0.6*) |
| T-PSA-3A | LNCaP | + | + | UPC-10 | 17.1(2.3*) |

Table 4: Ability of T cells generated with agonist peptide (PSA-3A) to lyse prostate cancer cells expressing native PSA. An 18-h $^{111}$In release assay was performed. LNCaP (human prostate carcinoma) cells are PSA positive and HLA-A2 positive. SK-mel (melanoma) cells are PSA negative and HLA-A2 positive. Experiments 1 and 2 were conducted at IVS 3 and 4, respectively. E:T ratio for experiment 2 was 25:1. The number in parentheses is the standard deviation. In experiment 2, LNCaP cells (1 × 10$^6$) were labeled with '"In and incubated for 1 h in the presence of medium containing no antibody, control antibody UPC-10 (10 μg/ml), or anti-HLAA2, 28 antibody (1:100 dilution). Cells were used as targets in an 18-h cytotoxic assay.
*Statistical significant (P < 0.01, two-tailed t test).

The HLA-A2/K$^b$ transgenic mouse has been previously reported to aid in the determination of the immunogenicity of HLA-A2 peptides for humans. This in vivo system was thus employed to further analyze and compare the immunogenicity of the PSA-3A peptide with that of the native PSA-3 peptide. DCs from the HLA-A2/K$^b$ transgenic mice were pulsed with either the PSA-3 or the PSA-3A peptide and used to vaccinate HLA-A2b mice. DCs alone (no peptide) were also used as a control vaccine. After three vaccinations at 2-week intervals, T cells were isolated from splenocytes obtained 2 weeks after the last vaccination. The T cells were then incubated with Jurkat A2/K$^b$ cells pulsed with the PSA-3 peptide, the PSA-3A peptide, or no peptide, and production of INF-γ was measured from supernatants after 24 h.

Table 5, below, shows that the use of DCs alone with no peptide as immunogen resulted in no INF-γ production by T cells. In contrast, T cells obtained from mice vaccinated with DCs pulsed with the PSA-3 peptide did produce INF-γ when APCs were pulsed with either peptide PSA-3 or PSA3A (Table 5). However, much higher levels of INF-γ, were produced from T cells of mice vaccinated with DCs pulsed with the PSA-3A peptide when stimulated with Jurkat A$_2$/K$^b$ cells pulsed with either the native or agonist PSA peptide (Table 5). These studies thereby provide additional evidence that the PSA-3A epitope is more immunogenic than the PSA-3 epitope in the context of the HLA-A2 allele.

TABLE 5

| Mice immunized with | Jurkat A2/K$^b$ Cells Pulsed with Peptide | Production of IFN-γ (pg/ml/10$^6$ cells) |
|---|---|---|
| DCs no peptide) | PSA-3 | <37.0 |
| DCs no peptide) | PSA-3A | <37.0 |
| DCs no peptide) | None | <37.0 |
| DCs pulsed with PSA-3 | PSA-3 | 1,908.0 |
| DCs pulsed with PSA-3 | PSA-3A | 1,969.0 |
| DCs pulsed with PSA-3 | None | <37.0 |
| DCs pulsed with PSA-3A | PSA-3 | 5,094.3 |
| DCs pulsed with PSA-3A | PSA-3A | 6,218.9 |
| DCs pulsed with PSA-3A. | None | <37.0 |

Table 5: Immunogenicity of PSA-3 vs PSA-3A peptides in HLA-A2/K$^b$ transgenic mice. T cells were obtained from mice immunized with DCs only, PSA-3 pulsed DCs, or PSA-3A pulsed DCs. Three mice were used in each group. Three injections (1 × 10$^6$ DC/mouse/injection) were given to each animal at 2-week intervals. Peptides were used at a concentration of 50 μg/ml. T cells obtained from HLA-A2/K$^b$ transgenic mice were stimulated with PSA-3 or PSA-3A peptide (25 μg/ml) pulsed Jurkat A2/K$^b$ cells in the IFN-γ production assay. Twenty-four h culture supernatants were collected and screened for the secretion of IFN-γ.

The experiments of this invention indicate the advantage of the use of the PSA-3A epitope in either a peptide-based vaccine or a peptide-pulsed DC vaccine. Experiments were also performed to construct vectors that contain the entire gene for PSA, but with the altered amino acid sequence of the PSA-3A epitope. Recombinant vaccinia viruses were thus constructed with the entire PSA transgene without and with the amino acid change of isoleucine to leucine at position 155. These recombinant vaccinia viruses were designated rV-PSA and rV-PSA-3A, respectively. Initial studies showed the optimal multiplicity of infection for human DCs for both recombinant vaccinia viruses to be 10 pfu per cell. Human DCs infected with either of the recombinant vectors showed the production of PSA protein at approximately 63 ng/ml as determined by immunoassay of supernatant fluids. Moreover, infection of human DCs with rV-PSA, rV-PSA-3A, and wild-type vaccinia virus did not alter the surface phenotype markers CD80, CD86, CD54, CD58, Class I, and Class II of DCs.

DCs infected with either rV-PSA or rV-PSA-3A were used to stimulate T cells originally derived by pulsing APC with the native PSA-3 peptide. Table 6, below, shows that DCs infected with the rV-PSA-3A recombinant were more effective in activating PSA-specific T cells, as measured by interferon production, than the use of DCs infected with rV-PSA. For comparison, noninfected DCs pulsed with 25 μg of the PSA-3A peptide were also used to activate T-PSA-3 T cells. As a specificity control, no activation of the CEA-specific T cell line (V8T) was observed by the PSA recombinant vectors. As an additional control, DCs infected with wild-type vaccinia vector were used. These studies thereby demonstrate that the altered PSA epitope can also be processed by human DCs and presented for the activation of specific T cells.

TABLE 6

| DCs Infected with | Pulsed with Peptide | Production of IFN-γ (pg/ml) by | | |
|---|---|---|---|---|
| | | T-PSA-3 | V8T | None |
| rV-PSA | None | 195.5 | <13.0 | <13.0 |
| rV-PSA PSA-3A | None | 425.5 | <13.0 | <13.0 |
| V-WT | PSA-3A | 946.6 | <13.0 | <13.0 |
| None | PSA-3A | 915.9 | <13.0 | <13.0 |
| V-WT | CAP1-6D | <13.0 | 787.4 | <13.0 |
| V-WT | None | <13.0 | <13.0 | <13.0 |
| None | None | <13.0 | <13.0 | <13.0 |

Table 6: Ability of DCs infected with vaccinia PSA recombinants to process the PSA-3A agonist epitope to activate PSA-specific T cells. PSA-specific T-PSA-3 cells and CEA-specific V8T cells were stimulated with irradiated allogeneic DCs either uninfected or infected with rV-PSA, rV-PSA (PSA-3A), or V-WT (wild type). For comparison, uninfected DCs or DCs infected with V-WT were pulsed with PSA-3A peptide or the CAP1-6D peptide. Peptides were used at a concentration of 25 µg/ml. Vaccinia virus vector infections were at a MOI of 10 for 1-h. Infected cells were then incubated overnight in completed medium at 37° C. and used as APC. Forty-eight h culture supernatants were collected and screened for the secretion of IFN-γ, The CAP1-6D peptide is a TCR-agonist of the CEA peptide CAP-1.

The results presented here demonstrate that the agonist peptide PSA-3A epitope is superior to the native PSA-3 epitope in terms of affinity of binding to MHC, avidity of the peptide MHC complex, and ability to activate CTL in vitro. The agonist epitope was also more efficient than the native epitope in T cell activation in an in vivo HLA-A2.11K$^b$ transgenic mice model (P. Correale et al., 1998, J. Immmunol. 161:3186–3194). T cells activated by the PSA-3A peptide had the ability to lyse both APCs pulsed with native peptide and human prostate cancer cells expressing native PSA in an MHCrestricted manner. The studies with the vaccinia recombinants demonstrated that the agonist epitope, in the context of a whole PSA molecule, could also be processed and presented by APC for T cell activation. Moreover, T cells stimulated by the agonist peptide, as compared with the native peptide, were shown to produce higher levels of type I cytokines, but were not subject to increased apoptosis.

Analysis of 10-mer HLA-A2.1 ligands has suggested that residues strongly associated with good HLA-A2.1 binding are L and M for primary anchor position 2, and V, L and I for position 10 (J. Ruppert et al., 1993, Cell 74:929–93). Substitution of I with L at position 2 (amino acid position 155) of the PSA-3 peptide improved the efficiency of the peptide binding to the HLA-A2.1 molecule. This observation can be explained by the fact that residue I at position 2 can reduce the peptide binding affinity to HLA-A2.1 as well as the stability of the resulting peptide-MHC complexes (J. Ruppert et al., 1993, Cell 74:929–937; M. Bouvier and D. C. Wiley, 1994, Science 265:398–402). Replacement of T with L or I at the N-terminal anchoring position 2 of gp 100 154–162 resulted in significantly improved binding to HLA-A2 molecule. However, there was no difference in the peptide binding affinity or antigenicity between the substitution with L or I (A. B. H. Bakker et al., 1997, Int. J. Cancer 70:302–309). On the other hand, substitution of A with L at position 2 of the nonapeptide Melan-A 27–35 resulted in increased peptide binding to HLA-A2, but with a greater than 50-fold reduction in antigenic activity (D. Valmori et al., 1998, J. Immunol. 160:1750–1758).

Substitution of V with L at position 10 resulted in a decrease in binding of the PSA-3 peptide to the HLA-A2.1 molecule. This may be explained partially by the fact that L at position 9, instead of V, reduced the peptide-HLA-A2.1 affinity as well as the complexes' stability (J. Ruppert et al., 1993, Cell 74:929–937; D. R. Madden, 1995, Ann. Rev. Immunol. 13:387–622). It has been demonstrated that in the case of Flu A matrix HLA-A2.1 binding peptides 58–66 (GILGFVFTL; SEQ ID NO:6) and 58–68 (GILGFVTLVL; SEQ ID NO:7), no decrease in binding to HLA-A2 was detected when V, instead of L, was at the C-terminal (H. W. Nijman et al., 1993, Eur. J. Immunol. 23:1215–1219). This is in agreement with the report of Chen et al. (J. L. Chen et al., 2000, J. Immunol. 165:948–955) that a 10mer peptide of NY-ESO-157–166 (SLLMWITQCV; SEQ ID NO:8) containing V at the C-terminal recognized HLA-A2 more efficiently than the wild-type peptide (SLLMWITQCF; SEQ ID NO:9) and NY-ESO-157–166 peptide (SLLMWITQAL; SEQ ID NO:10) containing L at the C-terminal. On the other hand, an increase in binding to HLA-A2 was observed when L was at the C-terminal instead of V in Flu A matrix peptides 2–11 (SLLTEVETYV; SEQ ID NO:11) and 2–12 (SLLTE-VETYVL; SEQ ID NO:12) (H. W. Nijman et al., Eur. J. Immunol. 23:1215–1219).

Substitution at position 1 with Y increased the binding of PSA-3 peptide to HLA-A2.1 in our study. This is in agreement with the observation that substitution of an aromatic residue at position 1 favors 10-mer binding to HLA-A2.1 (J. Ruppert et al., 1993, Cell 74:929–937). Similar results have been reported by Valmori et al. (D. Valmori et al., 1998, J. Immunol. 160:1750–1758) with respect to a Melan-A peptide 26–35 (EAAGIGILTV; SEQ ID NO:13), in which substitution of Y for E at position 1 (YAAGIGILTV; SEQ ID NO:14) increased the binding affinity of the peptide. On the other hand, gp100 peptide 280–288 (YLEPGPVTA; SEQ ID NO:15) containing Y at position 1 did not bind well to HLA-A2 molecule (Y. Kawakami et al., 1995, J. Immunol. 154:3961–3968). Residues strongly associated with poor HLA-A2.1 binding at the secondary anchor position are D, E, P at position 1; D, E at position 3; R, K, H, A at position 4; P at position 5; R, K, H at position 7; D, E, R, K, H at position 8; and R, K, H at position 9 (H. G. Rammensee et al., 1995, Immunogenetics 41:178–228). No residue associated with poor HLA-A2.1 binding at the secondary anchor positions is present in PSA-3 peptide.

Interestingly, the analog peptide made by amino acid substitution with L at position 2 (amino acid position 155) and with Y at position 1 (amino acid position 154) was not as efficient in binding to the HLA-A2.1 molecule as the native PSA-3 peptide when assayed by binding to T2A2 cells. This may have resulted from negative effects such as conformational changes, steric hindrances, or repulsive electrostatic interactions. It has been demonstrated that, a gp100 peptide 280–288 (YLEPGPVTA; SEQ ID NO:15) contains the predicted motif residues Y at position 1 µL at position 2, and A at position 9. These residues are predicted to support good binding to the HLA-A2.1 molecule, but the actual binding affinity of this peptide was not high. The lower affinity of the peptide may be due to residues at other positions of the peptide, such as a negatively charged E at position 3 (Y. Kawakami et al., 1995, J. Immunol. 154: 3961–3968; A. L. Cox et al., 1994, Science 264:716–719).

The use of agonist peptides in vaccine therapy has been demonstrated in two recent clinical trials. In one clinical trial, a melanoma gp100 peptide with an altered anchor residue used in combination with IL-2 produced more clinical responses in melanoma patients than a native gp100 peptide used in combination with IL-2 (S. A. Rosenberg et al., 1999, J. Immunol. 163:1690–1695). In another clinical trial, one of the amino acids of the CEA peptide CAP1 that interacts with the T cell receptor (TCR) was modified to generate the CAP1-6D TCR enhancer agonist epitope (S. Zaremba et al., 1997, Cancer Res. 57:4570–4577). DCs pulsed with the CAP1-6D agonist were used as a vaccine in patients with advanced CEA expressing carcinomas (L. H. Fong et al., Amer. Assoc. for Cancer Res. Ann. Mtg. Apr. 1–5, 2000 *Proceedings* #1387, 41:217). In the initial cohort of six vaccinated patients, serum CEA stabilization was seen in a subset of patients and regression of lung metastases was observed. CEA-specific T cell responses were also generated in patients using the agonist epitope (L. H. Fong et al., *Amer. Assoc. for Cancer Res. Ann. Mtg.* Apr. 1–5, 2000 *Proceedings* #1387, 41:217).

Importantly, the agonist PSA-3A peptide described herein is useful either as a peptide vaccine in adjuvant or via peptide-pulsed DCs in vaccine therapy for prostate cancer patients positive for the HLA-A2 allele. Recent studies showing enhanced peptide-pulsed DCs activity using molecules such as Flt-3L (E. Maraskovsky et al., 1996, *J. Exp. Med.* 184:1953–1962; S. D. Lyman, 1995, *Int. J. Hematol.* 62:63–73) or TRICOM vectors, i.e., vectors containing three costimulatory molecules (J. W. Hodge et al., 2000, *J. Natl. Cancer Inst.* 92:1228–1239), allow researchers to successfully pursue DC vaccine protocols.

The results shown herein demonstrate that PSA-specific T cells, generated with the use of either the native PSA-3 epitope or the PSA-3A agonist, produced more IFN-γ in response to the PSA-3A peptide than the PSA-3 peptide. The production of IL-2, IL-4, IL-5, IL-10, TNF-α, and IFN-γ was determined by CBA assay as described in the Examples section. These data show the increase in the production of IL-2, IL-5, and IFN-γ, but not IL-4 and IL-10 from T cells stimulated with PSA-3A as compared to PSA-3 peptide. Increases in the production of IL-5 by the activated T cells may in turn activate eosinophils, basophils, B cells, and thymocytes. IL-5 is a chemotactic and activating factor for eosinophils. IL-5 has also been shown to exhibit a killer-helper factor activity on peanut agglutinin binding thymocytes in the presence of stimulator cells and IL-2. This results in the recruitment of CTL from among the thymocyte population due to the ability of IL-5 to upregulate IL-2 receptors on target thymocytes (K. Takatsu et al., 1987, *Proc. Natl. Acad. Sci. USA* 84:4234–4238; S. C. Bischoff et al., 1990, *J. Exp. Med.*, 172:1577–1582). This suggests that the PSA-3A peptide may also be used in more sensitive immunoassays to monitor immune responses of patients involved in PSA vaccine clinical trials.

Several clinical trials using PSA-based vaccines have been completed or are in progress in patients with prostate cancer. A recent study in patients with advanced prostate cancer demonstrated that an rV-PSA vaccine induced specific T cell responses for the PSA-3 peptide in five of seven HLA-A2.1 patients vaccinated (J. P. Eder et al., 2000, *Clin. Cancer Res.* 6:1632–1638). The rV-PSA vaccine was shown to be safe, and certain patients remained without evidence of clinical progression for at least 21 months (J. P. Eder et al., 2000, *Clin. Cancer Res.* 6:1632–1638). Ongoing clinical trials are employing rV-PSA as a primary vaccination, followed by multiple booster vaccinations with a recombinant fowlpox-PSA vaccine. This diversified prime and boost vaccine strategy has shown to be advantageous in both animal models (J. W. Hodge et al., 1997, *Vaccine* 15:759–768, 1997) and clinical trials (J. L. Marshall et al., 2000, *J. Clin. Oncol.* 18:3964–3973) using recombinant CEA vector vaccines.

The experiments reported here demonstrate that the single amino acid change in the PSA molecule can also be used in recombinant PSA vaccinia or fowlpox vectors, or any DNA vector, to activate T cells more efficiently than the use of the same vector containing the native PSA gene. While the agonist epitope may only benefit patients possessing an HLA-A2 allele, this still constitutes approximately one-half of the Caucasian population, as well as other populations to a lesser extent. In addition, the experiments of the invention support the concept that a single amino acid change in the composition of a CTL epitope of a relatively weak immunogenic self-antigen, such as PSA, can be used to more efficiently activate specific T cell populations capable of lysing tumors expressing the native gene product.

Example 13

Generation of Cytotoxic T cells. PBMC can be separated using Lymphocyte Separation Medium gradient (Organon Telnika, Durham, N.C.) as previously described (Boyum et al., 1968, *Scand. J. Clin. Lab. Invest.* 21:77–80). Washed PBMC are resuspended in a complete medium, for example, RPMI 1640 (GIBCO) supplemented with 10% pool human AB serum (Pel-Freeze Clinical System, Brown Dear, Wis.), 2 nM glutamine, 100 U/ml penicillin and 100 μg/ml of streptomycin (GIBCO). PBMC at a concentration of about $2 \times 10^5$ cells in complete medium in a volume of, for example, 100 μl, are added into each well of a 96-well flat-bottom assay plate (Costar, Cambridge, Mass., USA). The antigen or peptides are added into the cultures in a final concentration of about 50 μg/ml and incubated at 37° C. in a humidified atmosphere containing 5% $CO_2$ for 5 days. After removal of peptide containing media, the cultures are provided with fresh human IL-2 (10 U/ml) after 5 days and replenished with IL-2 containing medium every 3 days. Primary cultures are restimulated with the same peptide (50 μg/ml) on day 16. Following this, $5 \times 10^5$ irradiated (4,000 rad) autologous PBMC are added in a volume of about 50 μl complete medium as antigen-presenting cells (APC). About five days later, the cultures are provided with human 1L-2 containing medium as described previously. Cells are restimulated for 5 days at intervals of 16 days.

All patent applications, patents, texts, and literature references cited in this specification are hereby incorporated herein by reference in their entirety to more fully describe the state of the art to which the present invention pertains.

As various changes can be made in the above methods and compositions without departing from the scope and spirit of the invention as described, it is intended that all subject matter contained in the above description, shown in the accompanying drawings, or set forth in the preceding embodiments be interpreted as illustrative, and not in a limiting sense.

SEQUENCE LISTING

<160> NUMBER OF SEQ ID NOS: 30

<210> SEQ ID NO 1
<211> LENGTH: 10
<212> TYPE: PRT
<213> ORGANISM: Artificial Sequence
<220> FEATURE:
<223> OTHER INFORMATION: Synthetic peptide

```
<400> SEQUENCE: 1

Val Ile Ser Asn Asp Val Cys Ala Gln Val
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic peptide

<400> SEQUENCE: 2

Val Ile Ser Asn Asp Val Cys Ala Gln Leu
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic peptide

<400> SEQUENCE: 3

Val Leu Ser Asn Asp Val Cys Ala Gln Val
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic peptide

<400> SEQUENCE: 4

Tyr Ile Ser Asn Asp Val Cys Ala Gln Val
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic peptide

<400> SEQUENCE: 5

Tyr Leu Ser Asn Asp Val Cys Ala Gln Val
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Synthetic peptide

<400> SEQUENCE: 6

Gly Ile Leu Gly Phe Val Phe Thr Leu
1               5

<210> SEQ ID NO 7
<211> LENGTH: 10
<212> TYPE: PRT
<213> ORGANISM: Artificial Sequence
<220> FEATURE:
<223> OTHER INFORMATION: Synthetic peptide

<400> SEQUENCE: 7
```

```
Gly Ile Leu Gly Phe Val Thr Leu Val Leu
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic peptide

<400> SEQUENCE: 8

Ser Leu Leu Met Trp Ile Thr Gln Cys Val
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic peptide

<400> SEQUENCE: 9

Ser Leu Leu Met Trp Ile Thr Gln Cys Phe
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthetic peptide

<400> SEQUENCE: 10

Ser Leu Leu Met Trp Ile Thr Gln Ala Leu
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetic peptide

<400> SEQUENCE: 11

Ser Leu Leu Thr Glu Val Glu Thr Tyr Val
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic peptide

<400> SEQUENCE: 12

Ser Leu Leu Thr Glu Val Glu Thr Tyr Val Leu
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Synthetic peptide

<400> SEQUENCE: 13
```

```
Glu Ala Ala Gly Ile Gly Ile Leu Thr Val
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthetic peptide

<400> SEQUENCE: 14

Tyr Ala Ala Gly Ile Gly Ile Leu Thr Val
1               5                   10

<210> SEQ ID NO 15
<211> LENGTH: 9
<212> TYPE: PRT
<213> ORGANISM: Artificial Sequence
<220> FEATURE:
<223> OTHER INFORMATION: Synthetic peptide

<400> SEQUENCE: 15

Tyr Leu Glu Pro Gly Pro Val Thr Ala
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic peptide

<400> SEQUENCE: 16

His His His His His His
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic peptide

<400> SEQUENCE: 17

Asp Tyr Lys Asp Asp Asp Asp Lys
1               5

<210> SEQ ID NO 18
<211> LENGTH: 30
<212> TYPE: DNA
<213> ORGANISM: Artificial Sequence
<220> FEATURE:
<223> OTHER INFORMATION: Synthetic polynucleotide sequence

<400> SEQUENCE: 18
gttatttcca atgacgtgtg tgcgcaagtt                                    30

<210> SEQ ID NO 19
<211> LENGTH: 30
<212> TYPE: DNA
<213> ORGANISM: Artificial Sequence
<220> FEATURE:
<223> OTHER INFORMATION: Synthetic polynucleotide sequence

<400> SEQUENCE: 19
gttatttcca atgacgtgtg tgcgcaactg                                    30
```

```
<210> SEQ ID NO 20
<211> LENGTH: 30
<212> TYPE: DNA
<213> ORGANISM: Artificial Sequence
<220> FEATURE:
<223> OTHER INFORMATION: Synthetic polynucleotide sequence

<400> SEQUENCE: 20
gttctgtcca atgacgtgtg tgcgcaagtt                                        30

<210> SEQ ID NO 21
<211> LENGTH: 30
<212> TYPE: DNA
<213> ORGANISM: Artificial Sequence
<220> FEATURE:
<223> OTHER INFORMATION: Synthetic polynucleotide sequence

<400> SEQUENCE: 21
tacatttcca atgacgtgtg tgcgcaagtt                                        30

<210> SEQ ID NO 22
<211> LENGTH: 30
<212> TYPE: DNA
<213> ORGANISM: Artificial Sequence
<220> FEATURE:
<223> OTHER INFORMATION: Synthetic polynucleotide sequence

<400> SEQUENCE: 22
tacctgtcca atgacgtgtg tgcgcaagtt                                        30

<210> SEQ ID NO 23
<211> LENGTH: 261
<212> TYPE: PRT
<213> ORGANISM: Homo sapiens

<400> SEQUENCE: 23
```

Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
            100                 105                 110

Pro Gly Asp Asp Ser Ser His Asp Leu Met Leu Leu Arg Leu Ser Glu
        115                 120                 125

Pro Ala Glu Leu Thr Asp Ala Val Lys Val Met Asp Leu Pro Thr Gln
    130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Ile Ser Asn Asp Val Cys Ala Gln Val His Pro Gln Lys Val
            180                 185                 190

```
Thr Lys Phe Met Leu Cys Ala Gly Arg Trp Thr Gly Gly Lys Ser Thr
            195                 200                 205

Cys Ser Gly Asp Ser Gly Gly Pro Leu Val Cys Asn Gly Val Leu Gln
        210                 215                 220

Gly Ile Thr Ser Trp Gly Ser Glu Pro Cys Ala Leu Pro Glu Arg Pro
225                 230                 235                 240

Ser Leu Tyr Thr Lys Val Val His Tyr Arg Lys Trp Ile Lys Asp Thr
                245                 250                 255

Ile Val Ala Asn Pro
            260

<210> SEQ ID NO 24
<211> LENGTH: 237
<212> TYPE: PRT
<213> ORGANISM: Homo sapiens

<400> SEQUENCE: 24

Ile Val Gly Gly Trp Glu Cys Glu Lys His Ser Gln Pro Trp Gln Val
1               5                   10                  15

Leu Val Ala Ser Arg Gly Arg Ala Val Cys Gly Gly Val Leu Val His
            20                  25                  30

Pro Gln Trp Val Leu Thr Ala Ala His Cys Ile Arg Asn Lys Ser Val
        35                  40                  45

Ile Leu Leu Gly Arg His Ser Leu Phe His Pro Glu Asp Thr Gly Gln
    50                  55                  60

Val Phe Gln Val Ser His Ser Phe Pro His Pro Leu Tyr Asp Met Ser
65                  70                  75                  80

Leu Leu Lys Asn Arg Phe Leu Arg Pro Gly Asp Asp Ser Ser His Asp
                85                  90                  95

Leu Met Leu Leu Arg Leu Ser Glu Pro Ala Glu Leu Thr Asp Ala Val
            100                 105                 110

Lys Val Met Asp Leu Pro Thr Gln Glu Pro Ala Leu Gly Thr Thr Cys
        115                 120                 125

Tyr Ala Ser Gly Trp Gly Ser Ile Glu Pro Glu Glu Phe Leu Thr Pro
    130                 135                 140

Lys Lys Leu Gln Cys Val Asp Leu His Val Ile Ser Asn Asp Val Cys
145                 150                 155                 160

Ala Gln Val His Pro Gln Lys Val Thr Lys Phe Met Leu Cys Ala Gly
                165                 170                 175

Arg Trp Thr Gly Gly Lys Ser Thr Cys Ser Gly Asp Ser Gly Gly Pro
            180                 185                 190

Leu Val Cys Asn Gly Val Leu Gln Gly Ile Thr Ser Trp Gly Ser Glu
        195                 200                 205

Pro Cys Ala Leu Pro Glu Arg Pro Ser Leu Tyr Thr Lys Val Val His
    210                 215                 220

Tyr Arg Lys Trp Ile Lys Asp Thr Ile Val Ala Asn Pro
225                 230                 235

<210> SEQ ID NO 25
<211> LENGTH: 261
<212> TYPE: PRT
<213> ORGANISM: Homo sapiens

<400> SEQUENCE: 25

Met Trp Val Pro Val Val Phe Leu Thr Leu Ser Val Thr Trp Ile Gly
1               5                   10                  15
```

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
            35                  40                  45

Val Cys Gly Gly Val Leu Val His Pro Gln Trp Val Leu Thr Ala Ala
 50                  55                  60

His Cys Ile Arg Asn Lys Ser Val Ile Leu Leu Gly Arg His Ser Leu
65                  70                  75                  80

Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
            100                 105                 110

Pro Gly Asp Asp Ser Ser His Asp Leu Met Leu Leu Arg Leu Ser Glu
            115                 120                 125

Pro Ala Glu Leu Thr Asp Ala Val Lys Val Met Asp Leu Pro Thr Gln
130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Val Leu Ser Asn Asp Val Cys Ala Gln Val His Pro Gln Lys Val
            180                 185                 190

Thr Lys Phe Met Leu Cys Ala Gly Arg Trp Thr Gly Gly Lys Ser Thr
            195                 200                 205

Cys Ser Gly Asp Ser Gly Gly Pro Leu Val Cys Asn Gly Val Leu Gln
    210                 215                 220

Gly Ile Thr Ser Trp Gly Ser Glu Pro Cys Ala Leu Pro Glu Arg Pro
225                 230                 235                 240

Ser Leu Tyr Thr Lys Val Val His Tyr Arg Lys Trp Ile Lys Asp Thr
                245                 250                 255

Ile Val Ala Asn Pro
            260

<210> SEQ ID NO 26
<211> LENGTH: 237
<212> TYPE: PRT
<213> ORGANISM: Homo sapiens

<400> SEQUENCE: 26

Ile Val Gly Gly Trp Glu Cys Glu Lys His Ser Gln Pro Trp Gln Val
1               5                   10                  15

Leu Val Ala Ser Arg Gly Arg Ala Val Cys Gly Gly Val Leu Val His
            20                  25                  30

Pro Gln Trp Val Leu Thr Ala Ala His Cys Ile Arg Asn Lys Ser Val
            35                  40                  45

Ile Leu Leu Gly Arg His Ser Leu Phe His Pro Glu Asp Thr Gly Gln
    50                  55                  60

Val Phe Gln Val Ser His Ser Phe Pro His Pro Leu Tyr Asp Met Ser
65                  70                  75                  80

Leu Leu Lys Asn Arg Phe Leu Arg Pro Gly Asp Asp Ser Ser His Asp
                85                  90                  95

Leu Met Leu Leu Arg Leu Ser Glu Pro Ala Glu Leu Thr Asp Ala Val
            100                 105                 110

Lys Val Met Asp Leu Pro Thr Gln Glu Pro Ala Leu Gly Thr Thr Cys

```
            115                 120                 125
Tyr Ala Ser Gly Trp Gly Ser Ile Glu Pro Glu Phe Leu Thr Pro
    130                 135                 140
Lys Lys Leu Gln Cys Val Asp Leu His Val Leu Ser Asn Asp Val Cys
145                 150                 155                 160
Ala Gln Val His Pro Gln Lys Val Thr Lys Phe Met Leu Cys Ala Gly
                165                 170                 175
Arg Trp Thr Gly Gly Lys Ser Thr Cys Ser Gly Asp Ser Gly Gly Pro
            180                 185                 190
Leu Val Cys Asn Gly Val Leu Gln Gly Ile Thr Ser Trp Gly Ser Glu
        195                 200                 205
Pro Cys Ala Leu Pro Glu Arg Pro Ser Leu Tyr Thr Lys Val Val His
    210                 215                 220
Tyr Arg Lys Trp Ile Lys Asp Thr Ile Val Ala Asn Pro
225                 230                 235

<210> SEQ ID NO 27
<211> LENGTH: 261
<212> TYPE: PRT
<213> ORGANISM: Homo sapiens

<400> SEQUENCE: 27

Met Trp Val Pro Val Phe Leu Thr Leu Ser Val Thr Trp Ile Gly
1               5                   10                  15
Ala Ala Pro Leu Ile Leu Ser Arg Ile Val Gly Gly Trp Glu Cys Glu
                20                  25                  30
Lys His Ser Gln Pro Trp Gln Val Leu Val Ala Ser Arg Gly Arg Ala
            35                  40                  45
Val Cys Gly Gly Val Leu Val His Pro Gln Trp Val Leu Thr Ala Ala
        50                  55                  60
His Cys Ile Arg Asn Lys Ser Val Ile Leu Leu Gly Arg His Ser Leu
65                  70                  75                  80
Phe His Pro Glu Asp Thr Gly Gln Val Phe Gln Val Ser His Ser Phe
                85                  90                  95
Pro His Pro Leu Tyr Asp Met Ser Leu Leu Lys Asn Arg Phe Leu Arg
            100                 105                 110
Pro Gly Asp Asp Ser Ser His Asp Leu Met Leu Leu Arg Leu Ser Glu
        115                 120                 125
Pro Ala Glu Leu Thr Asp Ala Val Lys Val Met Asp Leu Pro Thr Gln
    130                 135                 140
Glu Pro Ala Leu Gly Thr Thr Cys Tyr Ala Ser Gly Trp Gly Ser Ile
145                 150                 155                 160
Glu Pro Glu Glu Phe Leu Thr Pro Lys Lys Leu Gln Cys Val Asp Leu
                165                 170                 175
His Tyr Ile Ser Asn Asp Val Cys Ala Gln Val His Pro Gln Lys Val
            180                 185                 190
Thr Lys Phe Met Leu Cys Ala Gly Arg Trp Thr Gly Gly Lys Ser Thr
        195                 200                 205
Cys Ser Gly Asp Ser Gly Gly Pro Leu Val Cys Asn Gly Val Leu Gln
    210                 215                 220
Gly Ile Thr Ser Trp Gly Ser Glu Pro Cys Ala Leu Pro Glu Arg Pro
225                 230                 235                 240
Ser Leu Tyr Thr Lys Val Val His Tyr Arg Lys Trp Ile Lys Asp Thr
                245                 250                 255
```

Ile Val Ala Asn Pro
            260

<210> SEQ ID NO 28
<211> LENGTH: 237
<212> TYPE: PRT
<213> ORGANISM: Homo sapiens

<400> SEQUENCE: 28

Ile Val Gly Gly Trp Glu Cys Glu Lys His Ser Gln Pro Trp Gln Val
1               5                   10                  15

Leu Val Ala Ser Arg Gly Arg Ala Val Cys Gly Gly Val Leu Val His
            20                  25                  30

Pro Gln Trp Val Leu Thr Ala Ala His Cys Ile Arg Asn Lys Ser Val
        35                  40                  45

Ile Leu Leu Gly Arg His Ser Leu Phe His Pro Glu Asp Thr Gly Gln
    50                  55                  60

Val Phe Gln Val Ser His Ser Phe Pro His Pro Leu Tyr Asp Met Ser
65                  70                  75                  80

Leu Leu Lys Asn Arg Phe Leu Arg Pro Gly Asp Asp Ser Ser His Asp
                85                  90                  95

Leu Met Leu Leu Arg Leu Ser Glu Pro Ala Glu Leu Thr Asp Ala Val
            100                 105                 110

Lys Val Met Asp Leu Pro Thr Gln Glu Pro Ala Leu Gly Thr Thr Cys
        115                 120                 125

Tyr Ala Ser Gly Trp Gly Ser Ile Glu Pro Glu Glu Phe Leu Thr Pro
    130                 135                 140

Lys Lys Leu Gln Cys Val Asp Leu His Tyr Ile Ser Asn Asp Val Cys
145                 150                 155                 160

Ala Gln Val His Pro Gln Lys Val Thr Lys Phe Met Leu Cys Ala Gly
                165                 170                 175

Arg Trp Thr Gly Gly Lys Ser Thr Cys Ser Gly Asp Ser Gly Gly Pro
            180                 185                 190

Leu Val Cys Asn Gly Val Leu Gln Gly Ile Thr Ser Trp Gly Ser Glu
        195                 200                 205

Pro Cys Ala Leu Pro Glu Arg Pro Ser Leu Tyr Thr Lys Val Val His
    210                 215                 220

Tyr Arg Lys Trp Ile Lys Asp Thr Ile Val Ala Asn Pro
225                 230                 235

<210> SEQ ID NO 29
<211> LENGTH: 261
<212> TYPE: PRT
<213> ORGANISM: Homo sapiens

<400> SEQUENCE: 29

Met Trp Val Pro Val Val Phe Leu Thr Leu Ser Val Thr Trp Ile Gly
1               5                   10                  15

Ala Ala Pro Leu Ile Leu Ser Arg Ile Val Gly Gly Trp Glu Cys Glu
            20                  25                  30

Lys His Ser Gln Pro Trp Gln Val Leu Val Ala Ser Arg Gly Arg Ala
        35                  40                  45

Val Cys Gly Gly Val Leu Val His Pro Gln Trp Val Leu Thr Ala Ala
    50                  55                  60

His Cys Ile Arg Asn Lys Ser Val Ile Leu Leu Gly Arg His Ser Leu
65                  70                  75                  80

```
Phe His Pro Glu Asp Thr Gly Gln Val Phe Gln Val Ser His Ser Phe
                85                  90                  95

Pro His Pro Leu Tyr Asp Met Ser Leu Leu Lys Asn Arg Phe Leu Arg
            100                 105                 110

Pro Gly Asp Asp Ser Ser His Asp Leu Met Leu Leu Arg Leu Ser Glu
        115                 120                 125

Pro Ala Glu Leu Thr Asp Ala Val Lys Val Met Asp Leu Pro Thr Gln
    130                 135                 140

Glu Pro Ala Leu Gly Thr Thr Cys Tyr Ala Ser Gly Trp Gly Ser Ile
145                 150                 155                 160

Glu Pro Glu Glu Phe Leu Thr Pro Lys Lys Leu Gln Cys Val Asp Leu
                165                 170                 175

His Tyr Leu Ser Asn Asp Val Cys Ala Gln Val His Pro Gln Lys Val
            180                 185                 190

Thr Lys Phe Met Leu Cys Ala Gly Arg Trp Thr Gly Gly Lys Ser Thr
        195                 200                 205

Cys Ser Gly Asp Ser Gly Gly Pro Leu Val Cys Asn Gly Val Leu Gln
    210                 215                 220

Gly Ile Thr Ser Trp Gly Ser Glu Pro Cys Ala Leu Pro Glu Arg Pro
225                 230                 235                 240

Ser Leu Tyr Thr Lys Val Val His Tyr Arg Lys Trp Ile Lys Asp Thr
                245                 250                 255

Ile Val Ala Asn Pro
            260

<210> SEQ ID NO 30
<211> LENGTH: 237
<212> TYPE: PRT
<213> ORGANISM: Homo sapiens

<400> SEQUENCE: 30

Ile Val Gly Gly Trp Glu Cys Glu Lys His Ser Gln Pro Trp Gln Val
1               5                   10                  15

Leu Val Ala Ser Arg Gly Arg Ala Val Cys Gly Gly Val Leu Val His
            20                  25                  30

Pro Gln Trp Val Leu Thr Ala Ala His Cys Ile Arg Asn Lys Ser Val
        35                  40                  45

Ile Leu Leu Gly Arg His Ser Leu Phe His Pro Glu Asp Thr Gly Gln
    50                  55                  60

Val Phe Gln Val Ser His Ser Phe Pro His Pro Leu Tyr Asp Met Ser
65                  70                  75                  80

Leu Leu Lys Asn Arg Phe Leu Arg Pro Gly Asp Asp Ser Ser His Asp
                85                  90                  95

Leu Met Leu Leu Arg Leu Ser Glu Pro Ala Glu Leu Thr Asp Ala Val
            100                 105                 110

Lys Val Met Asp Leu Pro Thr Gln Glu Pro Ala Leu Gly Thr Thr Cys
        115                 120                 125

Tyr Ala Ser Gly Trp Gly Ser Ile Glu Pro Glu Glu Phe Leu Thr Pro
    130                 135                 140

Lys Lys Leu Gln Cys Val Asp Leu His Tyr Leu Ser Asn Asp Val Cys
145                 150                 155                 160

Ala Gln Val His Pro Gln Lys Val Thr Lys Phe Met Leu Cys Ala Gly
                165                 170                 175

Arg Trp Thr Gly Gly Lys Ser Thr Cys Ser Gly Asp Ser Gly Gly Pro
            180                 185                 190
```

```
Leu Val Cys Asn Gly Val Leu Gln Gly Ile Thr Ser Trp Gly Ser Glu
        195                 200                 205

Pro Cys Ala Leu Pro Glu Arg Pro Ser Leu Tyr Thr Lys Val Val His
    210                 215                 220

Tyr Arg Lys Trp Ile Lys Asp Thr Ile Val Ala Asn Pro
225                 230                 235
```

The invention claimed is:

1. An isolated nucleic acid molecule comprising a nucleic acid sequence selected from the group consisting of:
   (a) a nucleic acid sequence encoding at least one amino acid sequence selected from the group consisting of Val Leu Ser Asn Asp Val Cys Ala Gln Val (SEQ ID No.: 3), Tyr Ile Ser Asn Asp Val Cys Ala Gln Val (SEQ ID No.: 4), and Tyr Leu Ser Asn Asp Val Cys Ala Gln Val (SEQ ID No.: 5);
   (b) a nucleic acid sequence encoding at least one amino acid sequence selected from the group consisting of SEQ ID NO: 26, SEQ ID NO: 28, and SEQ ID NO: 30;
   (c) a nucleic acid sequence selected from the group consisting of SEQ ID NO: 20, SEQ ID NO: 21, and SEQ ID NO: 22; and
   (d) a nucleic acid sequence that is complementary to a nucleotide sequence of one of (a)–(c).

2. A vector comprising a nucleic acid of claim 1.

3. The vector of claim 2, wherein the vector is a viral vector selected from the group consisting of poxvirus retrovirus, adenovirus, herpes virus, polio virus, alphavirus, baculovirus, and Sindbis virus.

4. The vector of claim 3, wherein the vector is a pox virus vector selected from the group consisting of orthopox virus, vaccinia virus, avipox virus, fowlpox virus, capripox virus, and suipox virus.

5. A host cell comprising a vector of claim 2.

6. The host cell of claim 5, wherein the host cell is human.

7. The host cell of claim 5, wherein the host cell is a antigen presenting cell or tumor cell.

8. A primer comprising an isolated nucleic acid molecule of claim 1.

9. A probe comprising an isolated nucleic acid molecule of claim 1.

10. An isolated amino acid sequence comprising at least one sequence selected from the group consisting of Val Leu Ser Asn Asp Val Cys Ala Gln Val (SEQ ID No.: 3), Tyr Ile Ser Asn Asp Val Cys Ala Gln Val (SEQ ID No.: 4), and Tyr Leu Ser Asn Asp Val Cys Ala Gln Val (SEQ ID No.: 5).

11. An isolated amino acid sequence comprising a sequence selected from the group consisting of SEQ ID NO: 26, SEQ ID NO: 28, and SEQ ID NO: 30.

12. A kit for detecting a nucleic acid molecule comprising:
   a) a probe of claim 9; and
   b) at least one component to detect binding of the probe to a nucleic acid.

13. A method for detecting a nucleic acid comprising: a) incubating a probe of claim 9 with a biological sample comprising nucleic acids, thereby forming a hybridization complex; and b) detecting the complex formed in (a), wherein the presence of the complex indicates detection of a nucleic acid.

14. A method for recombinantly producing a protein comprising:
   a) culturing a host cell of claim 5 under conditions suitable for the production of a protein; and
   b) recovering the protein from said host cell or cell culture medium, thereby producing the protein.

15. A pharmaceutical composition comprising a vector of claim 2, and a physiologically acceptable carrier, excipient, or diluent.

16. A pharmaceutical composition comprising a host cell of claim 5, and a physiologically acceptable carrier, excipient, or diluent.

17. A pharmaceutical composition comprising an isolated amino acid of claim 10 and a physiologically acceptable carrier, excipient, or diluent.

18. A pharmaceutical composition comprising an isolated amino acid of claim 11 and a physiologically acceptable carrier, excipient, or diluent.

19. A method of treating prostate cancer comprising:
   administering a pharmaceutical composition of one of claims 17–18 in an amount sufficient to treat the prostate cancer.

20. The method of claim 19, wherein the pharmaceutical composition is co-administered with an adjuvant selected from the group consisting of alum, aluminum salts, aluminum phosphate, aluminum hydroxide, aluminum silica, an oily adjuvant composition of mannide oleate and mineral oil, and calcium phosphate.

21. The method of claim 19, wherein the pharmaceutical composition is co-administered with a biological adjuvant selected from the group consisting of interlukin-2 (IL-2), IL-6, IL-12, the cytokine known as Regulated on Activation, Normal T Expressed and Secreted (RANTES), Granulocyte macrophage colony-stimulating factor (GM-CSF), tumor necrosis factor-α (TNF-α), interferon-.gamma. (IFN-.gamma.), Granulocyte colony-stimulating factor (G-CSF), Intercellular adhesion molecule-1 (ICAM-1), leukocyte function-associated adhesion molecule-3 (LFA-3), CD72, B7-1, B7-2, OX-40L, and 41 BBL.

22. The method of claim 19, wherein the pharmaceutical composition is administered in conjunction with a therapy selected from the group consisting of hormone therapy, chemotherapy, surgery, cryosurgery, radiation therapy, interstitial brachytherapy, and anti-HER2 immunotherapy.

23. An apatamer of an isolated amino acid sequence comprising at least one sequence selected from the group consisting of Val Leu Ser Asn Asp Val Cys Ala Gln Val (SEQ ID No.: 3), Tyr Ile Ser Asn Asp Val Cys Ala Gln Val (SEQ ID No.: 4), and Tyr Leu Ser Asn Asp Val Cys Ala Gln Val (SEQ ID No.: 5).

* * * * *

UNITED STATES PATENT AND TRADEMARK OFFICE
CERTIFICATE OF CORRECTION

PATENT NO. : 7,247,615 B2
APPLICATION NO. : 10/497003
DATED : July 24, 2007
INVENTOR(S) : Jeffrey Schlom et al.

It is certified that error appears in the above-identified patent and that said Letters Patent is hereby corrected as shown below:

Col. 65, in claim 5, "A host cell comprising" should read --An isolated host cell comprising--

Col. 65, in claim 6, "The host cell of claim 5" should read --The isolated host cell of claim 5--

Col. 65, in claim 7, "The host cell of claim 5" should read --The isolated host cell of claim 5--

Col. 66, in claim 19, "A method of treating prostate cancer" should read --A method of treating [or preventing] prostate cancer--

Signed and Sealed this

Twentieth Day of November, 2007

JON W. DUDAS
*Director of the United States Patent and Trademark Office*